United States Patent
Ghetie et al.

(10) Patent No.: US 6,368,596 B1
(45) Date of Patent: Apr. 9, 2002

(54) COMPOSITIONS AND METHODS FOR HOMOCONJUGATES OF ANTIBODIES WHICH INDUCE GROWTH ARREST OR APOPTOSIS OF TUMOR CELLS

(75) Inventors: Maria-Ana Ghetie; Jonathan W. Uhr; Ellen S. Vitetta, all of Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/112,041

(22) Filed: Jul. 8, 1998

Related U.S. Application Data

(60) Provisional application No. 60/052,013, filed on Jul. 8, 1997.

(51) Int. Cl.[7] ............... A61K 39/395; A61K 39/40; A61K 39/42
(52) U.S. Cl. .................. 424/141.1; 424/130.1; 424/133.1; 424/134.1; 424/136.1; 424/138.1; 424/139.1; 424/142.1; 424/152.1; 424/155.1; 424/156.1; 424/172.1
(58) Field of Search ............ 424/136.1, 138.1, 424/155.1, 130.1, 133.1, 134.1, 139.1, 141.1, 142.1, 152.1, 156.1, 172.1

(56) References Cited

U.S. PATENT DOCUMENTS

| | | | |
|---|---|---|---|
| 5,273,743 A | * | 12/1993 | Ahlem et al. ............ 424/85.8 |
| 5,591,828 A | * | 1/1997 | Bosslet et al. ........... 530/387.3 |
| 5,683,694 A | * | 11/1997 | Bagshawe et al. ........ 424/178.1 |
| 5,686,072 A | | 11/1997 | Uhr et al. |

FOREIGN PATENT DOCUMENTS

| | | |
|---|---|---|
| EP | 0404097 | 12/1990 |
| EP | 0453082 | 10/1991 |
| EP | 0468637 | 1/1992 |
| WO | WO 91/03493 | 3/1991 |
| WO | WO 92/04053 | * 3/1992 |

OTHER PUBLICATIONS

Ruddon, R., Cancer Biology, p. 348, 1995.*

Adair, "Engineering antibodies for therapy," *Immunol. Rev.,* 192; 130:5–40, 1992.

(List continued on next page.)

*Primary Examiner*—Anthony C. Caputa
*Assistant Examiner*—Jennifer Hunt
(74) *Attorney, Agent, or Firm*—Fulbright & Jaworski L.L.P.

(57) ABSTRACT

This invention discloses monoclonal antibodies (MAbs) which have little or no signaling activity as monomers become potent anti-tumor agents when they are converted into homoconjugates. The homoconjugates exert anti-growth activity by signaling $G_0/G_1$ arrest or apoptosis, depending upon which cell surface molecule they bind. This activity is specific and does not require an Fc portion. These conjugates are potent, anti-tumor agents.

13 Claims, 17 Drawing Sheets

OTHER PUBLICATIONS

Akiyama et al., "Fibronectin and integrins in invasion and metastasis," *Cancer Metastasis Rev.*, 14:173–189, 1995.

Beckwith et al., "Anti–IgM mediated growth inhibition of a human B–lymphoma cell line is independent of phosphatidylinositol turnover and protein kinase C activation and involves tyrosine phosphorylation," *J. Immunol.*, 147:2411–2418, 1991.

Bridges et al., "Selective in vivo antitumor effect of monoclonal anti–I–A antibody on B cell lymphoma," *J. Immunol.*, 139:4242–4249, 1987.

Brown et al., "Antiidiotype antibody therapy of B–cell lymphoma," *Semin. Oncol.*, 16:199–210, 1989.

Brunner et al., "Cell–autonomous Fas (CD95)/Fas–ligand interaction mediates activation–induced apoptosis in T–cell hybridomas," *Nature*, 373:441–444, 1995.

Cumber et al., "Comparative stabilities in vitro and in vivo of a recombinant mouse antibody FvCys fragment and a bisFvCys conjugate," *J. Immunol.*, 149(1):120–126, 1992.

Denkers et al., "Influence of antibody isotype of passive serotherapy of lymphoma," *J. Immunol.*, 135:2183–2186, 1995.

Dhein et al., "Autocrine T–cell suicide mediated by APO–1/(Fas/CD95)," *Nature*, 373:438–441, 1995.

Dillman, "Antibodies a cytotoxic therapy," *J. Clin. Oncol.*, 12(7):1497–1515, 1994.

Dyer et al., "Effects of CAMPATH–1 antibodies in vivo in patients with lymphoid malignancies: Influence of antibody isotype," *Blood*, 73:1431–1439, 1989.

Edward, "Integrins and other adhesion molecules involved in malanocytic tumor progression," *Curr. Opin. Oncol.*, 7:185–191, 1995.

Funakoshi et al., "Inhibition of human B–cell lymphoma growth by CD40 stimulation," *Blood*, 83:2787–2794, 1994.

Ghetie et al., "The use of immunoconjugates in cancer therapy," *Exp. Opin. Invest. Drugs.*, 5(3):309–321, 1996.

Ghetie et al., "Evaluation of ricin A chain–containing immunotoxins directed against CD19 and CD22 antigens on normal and malignant human B–cells as potential reagents for in vivo therapy," *Cancer Res.*, 48:2610–2617, 1988.

Ghetie et al., "Anti–CD19 inhibits the growth of human B–cell tumor lines in vitro and of Daudi cells in SCID mice by inducing reversible cell cycle arrest," *Blood*, 83:1329–1336, 1994.

Ghetie et al., "Combination immunotoxin treatment and chemotherapy in SCID mice with advanced, disseminated Daudi lymphoma," *Int. J. Cancer*, 68:93–96, 1996.

Ghetie et al., "Disseminated or localized growth of a human B–cell tumor (Daudi) in SCID mice," *Int. J. Cancer*, 45:481–485, 1990.

Ghetie et al., "The GLP large scale preparation of immunotoxins containing deglycosylated ricin A chain and a hindered disulfide bond," *J. Immunol. Methods*, 142:223–230, 1991.

Ghetie et al., "Eradication of minimal disease in severe combined immunodeficient mice with disseminated Daudi lymphoma using chemotherapy and an immunotoxin cocktail," *Blood*, 84:702–707, 1994.

Ghetie et al., "The anti–tumor activity of an anti–CD22–immunotoxin in SCID mice with disseminated Daudi lymphoma is enhanced by either an anti–CD19 antibody or an anti–CD19 immunotoxin," *Blood*, 80:2315–2320, 1992.

Greenwood et al., "Engineering multiple–domain forms of the therapeutic antibody CAMPATH–IH: Effects on complement lysis", *Therap. Immunol.*, 1:247–255, 1994.

Guo et al., "Inhibition of human melanoma growth and metastasis in vivo by anti–CD44 monoclonal antibody," *Cancer Res.*, 54:1561–1565, 1994.

Hale et al., "Therapeutic potential of rat monoclonal antibodies: Isotype specificity of antibody–dependent cell–mediated cytotoxicity with human lymphocytes," *J. Immunol.*, 134:3056–3061, 1985.

Hale et al., "Remission induction in non–Hodgkin lymphoma with reshaped human monoclonal antibody," *Lancet*, 2:1394–1399, 1988.

Hamblin et al., "Preliminary experience in treating lymphocytic leukaemia with antibody to immunoglobulin idiotypes on the cell surfaces," *Br. J. Cancer*, 42:495–502, 1980.

Hamblin et al., "Initial experience in treating human lymphoma with a chimeric univalent derivative of monoclonal anti–idiotype antibody," *Blood*, 69:790–797, 1987.

Hekman et al., "Initial experience with treatment of human B cell lymphoma with anti–CD19 monoclonal antibody," *Cancer Immunol., Immunother.*, 32:364–372, 1991.

Herlyn and Koprowski, "IgG2a monoclonal antibodies inhibit human tumor growth through interaction with effector cells," *Proc. Natl. Acad. Sci. USA*, 79:4761–4765, 1982.

Hooijberg et al., "Enhanced antitumor effects of CD20 over CD19 monoclonal antibodies in a nude mouse xenograft model," *Cancer Res.*, 55(4):840–846, 1995.

Hooijberg et al., "Eradication of large human B cell tumors in nude mice with unconjugated CD20 monoclonal antibodies and interleukin 2," *Cancer Res.*, 55(12):2627–2634, 1995.

Ju et al., "Fas(CD95)/FasL interactions required for programmed cell death after T–cell activation," *Nature*, 373:444–448, 1995.

Kaminski et al., "Importance of antibody isotype in monoclonal anti–idiotype therapy of a murine B–cell lymphoma," *J. Immunol.*, 136:1123–1130, 1986.

Kaminski et al., "Radioimmuno–therapy of B–cell lymphoma with [1311]anti–B1 (anti–CD20) antibody," *N. Engl. J. Med.*, 329:459–465, 1993.

Marches et al., "Tumor dormancy and cell signaling III: Role of hypercrosslinking of IgM and CD40 on the induction of cell cycle arrest and apoptosis in B lymphoma cells," *Therap. Immunol.*, 2:125–136, 1996.

Meeker et al., "A clinical trial of anti–idiotype therapy for B cell malignancy," *Blood*, 65:1349–1363, 1985.

Page and Defranco, "Role of phosphoinositide–derived second messengers in mediated anti–IgM–induced growth arrest of WEHI–231 B lymphoma cells," *J. Immunol.*, 140:3717–26, 1988.

Press et al., "Monoclonal antibody 1 F5 (anti–CD20) serotherapy of human B cell lymphomas," *Blood*, 69:584–591, 1987.

Press et al., "Radiolabeled–antibody therapy of B–cell lymphoma with autologous bone marrow support," *N. Engl. J. Med.*, 329:1 219–1224, 1993.

Qi et al., "Antibody–targeted lymphokine–activated killer cells inhibit liver micrometastases in severe combined immunodeficient mice," *Gastroenterology* 109(6):1950–1957, 1995.

Racila et al., "Tumor dormancy and cell signaling: Anti-μ-induced apoptosis in human B-lymphoma cells is not caused by an APO-1—APO-1 ligand interaction," *Proc. Natl. Acad. Sci., USA*, 93:2165–2168, 1996.

Racila et al., "Tumor dormancy and cell signaling. II. Antibody as an agonist in inducing dormancy of a B cell lymphoma in SCID mice," *J. Exp. Med.*, 181:1539–1550, 1995.

Rankin et al., "Treatment of two patients with B–cell lymphoma with monoclonal anti–idiotype antibodies," *Blood*, 65:1373–1381, 1985.

Riethmüller et al., "Randomised trial of monoclonal antibody for adjuvant therapy of resected Dukes' colorectal carcinoma," *Lancet* 343:1174–1177, 1994.

Schreiber et al., "An unmodified anticarcinoma antibody, BR96, localizes to and inhibits the outgrowth of human tumors in nude mice," *Cancer Res.*, 52:3262–3266, 1992.

Scott et al., "Lymphoma models for B–cell activation and tolerance. II. Growth inhibition by anti–m of WEHI–231 and the selection and properties of resistant mutants", *Cell Immunol.*, 93:124–131, 1985.

Scott et al., "T cells commit suicide, but B cells are murdered," *J. Immunol.*, 156:2352–2356, 1996.

Smith and Morrison, "Recombination polymeric IgG: An approach to engineering more potent antibodies", *Bio/Technol.*, 12:683–688, 1994.

Trauth et al., "Monoclonal antibody–mediated tumor regression by induction of apoptosis," *Science*, 245:301–305, 1989.

Vitetta and Uhr, "Monoclonal antibodies as agonists: an expanded role for their use in cancer therapy," *Cancer Res.*, 54:5301–5309, 1994.

Wolff et al., "Human monoclonal antibody homodimers", *J Immunol.*, 148:2469–2474, 1992.

Wolff et al., "Monoclonal antibody and homoconjugates: Enhanced antitumor activity in nude mice", *Cancer Res.*, 53:2560–2565, 1993.

Yefenof et al., "Cancer dormancy: Isolation and characterization of dormant lymphoma cells," *Proc. Natl. Acad. Sci., USA*, 90:1829–1833, 1993.

Zahalka et al., "Lymph node (but not spleen) invasion by murine lymphoma is both CD44–and hyaluronate–dependent," *J. Immunol.*, 154:5345–5355, 1995.

Hellström et al., "Immunoconjugates and Immunotoxins for Therapy of Carcinomas," *Adv. Pharmacol.*, 33:349–388, 1995.

Levy and Miller, "Therapy of lymphoma directed as idiotypes", *J. Natl. Cancer Inst. Monographs*, 10:61–68, 1990.

Morrison and Oi, "Genetically engineered antibody molecules," *Adv. Immunol.*, 44:65–91, 1989.

Ruiz et al., "Suppression of mouse melanoma metastasis b EA–1, a monoclonal antibody specific for $\alpha_6$ integrins," *Cell Adhes. Commun.*, 1:67–81, 1993.

Waldmann, "Immune receptors: Targets for therapy of leukemia/lymphoma, autoimmune diseases and for the prevention of allograft rejection," *Annu. Rev. Immunol.*, 10:675–704, 1992.

Caron et al., "Engineered humanized dimeric forms of IgG are more effective antibodies," *J. Exp. Med.*, 176:1191–1195, Oct. 1992.

Hudson, "Recombinant antibody constructs in cancer therapy," *BioTechnology*, 12:548–555, Jul. 1994.

Mota et al., "Preparation and some properties of dimeric rabbit IgG antibody," *Mol. Immunol.*, 21(7):641–645, 1984.

Shopes, "A genetically engineered human IgG mutant with enhanced cytolytic activity," *Mol. Immunol.*, 148(9):2918–2922, May 1992.

Shuford et al., "Effect of light chain V region duplication on IgG oligomerization and in vivo efficacy," *Science*, 252(5006):724–7, May 1991.

Smith and Morrison, "Recombinant polymeric IgG: an approach to engineering more potent antibodies," *Bio/Technology*, 12:683–688, Jul. 1994.

Smith et al., "Addition of a μ–tailpiece to IgG results in polymeric antibodies with enhanced effector functions including complement–mediated cytolysis by IgG4," *J. Immunol.*, 154:2226–2236, 1995.

Wolff et al., "Monoclonal antibody homodimers: enhanced antitumor activity in nude mice," *Can. Res.*, 53:2560–2565, Jun. 1993.

Wolff et al., "Human monoclonal antibody homodimers: effect of valency on in vitro and in vivo antibacterial activity," *J. Immunol.*, 148(8):2469–2472, Apr. 1992.

International Search Report dated Jan. 15, 1999 (PCT/US98/14222)(UTFD:521P).

Kita et al., "ERBB receptor activation, cell morphology changes, and apoptosis induced by anti–HER2 monoclonal antibodies," *Biochem. Biophys. Res. Comm.*, 226(1):59–69, 1996.

Wu et al., "Apoptosis induced by an anti–epidermal growth factor receptor monoclonal antiobody in a human colorectal carcinoma cell line and its delay in insulin," *J. Clin. Invest.*, 95(4):1897–1905, 1995.

* cited by examiner

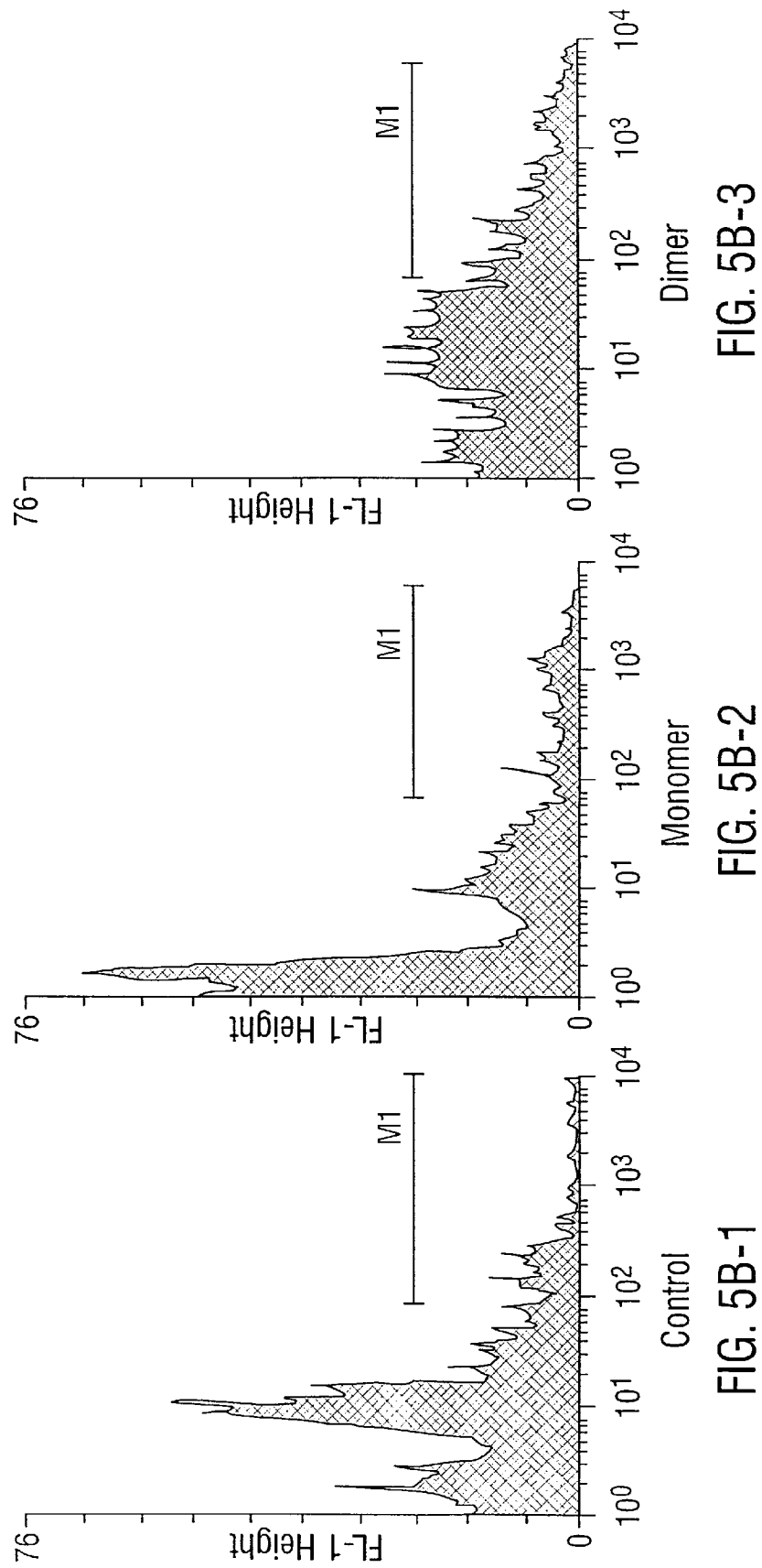

COMPOSITIONS AND METHODS FOR HOMOCONJUGATES OF ANTIBODIES WHICH INDUCE GROWTH ARREST OR APOPTOSIS OF TUMOR CELLS

The present application claims priority to U.S. Ser. No. 60/052,013, filed Jul. 8, 1997.

The government owns rights in the present invention pursuant to grant number CA-28149 from the National Institutes of Health.

BACKGROUND OF THE INVENTION

1. Field of the Invention

The present invention relates generally to the fields of immunology and tumor therapy. More particularly, it concerns homoconjugates of antibodies which arrest cell growth and/or signal apoptosis in the tumor cells. The components of these homoconjugate antibodies can comprise a wide variety of antibodies but often and surprisingly do not require an Fc region to function and importantly activate fewer, or even no, undesired immunological reactions.

2. Description of Related Art

During the past two decades, a variety of monoclonal antibodies (MAbs) have been selected for clinical use based on their effector functions and the most encouraging results have emerged from the treatment of NHL (Hjekman et al., 1991; Press et al., 1987; Meeker et al., 1985; Waldmann, 1992; Hale et al, 1988; Dyer et al., 1989; Hamblin et al., 1987; Brown et al., 1989; Rankin et al., 1985) and, in particular, when radioimmunoconjugates were used (Kaminski et al., 1993; Press et al., 1993). Two examples are the epithelial cell-reactive MAb, 17.1A (Herlyn and Koprowski, 1982; Riethmüller et al., 1994) and the lymphoma reactive MAb, CAMPATH-1 (Dyer et al., 1989; Hale et al., 1988). In this regard, there is considerable experimental (Hooijberg et al., 1995a; Hooijberg et al., 1995b), and some clinical (Riethmüller et al., 1994; Hale et al., 1988) evidence to indicate that effector functions play an important role in the anti-tumor activity of MAbs. Those MAbs which do not fix complement or mediate antibody-dependent cell mediated cytotoxicity (ADCC) have been converted into useful ones by chimerization (Morrison and Oi, 1989; Adair, 1992), by generating switch variants (Hale et al., 1985; Kaminski et al., 1986; Denkers et al., 1995) or by preparing cytotoxic immunoconjugates (Dillman, 1994; Ghetie et al., 1996b; Hellström et al., 1995).

It has been demonstrated that the crosslinking of mIg on human Daudi cells initiates a cascade of signals leading to the induction of both apoptosis and CCA (Racila et al., 1996). Using antisense oligonucleotides, it was shown that the mig-associated Lyn tyrosine kinase was required for anti-Ig mediated CCA but not for the induction of apoptosis (Racila et al., 1995). It was also shown that Lyn was critical for the induction of CA by anti-CD19 (Racila et al., 1995). These results suggest that the signaling pathways leading to CCA and apoptosis might bifurcate at an early stage of BCR crosslinking.

In attempting to further distinguish the different signaling pathways, studies were conducted to understand signal transduction initiated by crosslinking BCRs. Recent evidence supports a mechanism whereby TCR-induced apoptosis is dependent on Fas/Fas ligand interactions. Thus, crosslinking TCRs results in transient upregulation of the Fas ligand in T-lymphoma cells (Dhein et al., 1995; Brunner et al., 1995; Ju et al., 1995). Apoptosis induced by T cell receptor/T cell receptor (TCR) crosslinking is markedly inhibited by either anti-Fas F(ab')$_2$ fragments (which are not cytotoxic) or soluble Fas-Fc (Dhein et al., 1995; Brunner et al., 1995; Ju et al., 1995). These results indicate that in T-lymphoma cells, apoptosis induced by TCR activation results from the induction of the expression of the Fas ligand and its interaction with Fas resulting in the activation of the Fas signaling pathway.

In contrast to T cells, crosslinking of membrane IgM on Daudi cells (which constitutively express Fas) did not induced synthesis of Fas ligand (Racila et al., 1996). Furthermore, a noncytotoxic fragment of anti-Fas that blocked T cell receptor-mediated apoptosis did not block anti-$\mu$ induced apoptosis. Hence, in the B lymphoma cells, Daudi, apoptosis induced by signaling via IgM is not mediated by the Fas ligand. Similar results were obtained using a murine lymphoma (Scott et al., 1996). More recent studies suggest that the signaling is related to TNF$\alpha$ and TNF$\beta$ which are the only members of the TNF family which are upregulated in Daudi cells after crosslinking IgM. These studies suggest that IgM and CD19 may utilize different signaling pathways and that the activation pathways in Daudi cells are different from those induced via TCRs in T lymphoma cells.

Hence, like anti-CD40 (Marches et al., 1996), anti-CD19 enhanced the apoptosis induced by anti-$\mu$. This finding is relevant for clinical strategies because it is obviously more desirable to kill a tumor cell than to induce CCA. The combination of anti-$\mu$ and anti-CD19 was studied in SCID/Daudi mice (where there is no serum IgM). Using multiple titrations of the two agents in the animals with a relatively long read-out period of 150 days. (Anti-$\mu$ will not be useful as a therapeutic agent in normal mice and humans, but is useful as a demonstration model.) In studying several MAbs which react with these molecules, it was found that none signaled as well as the anti-CD19 (HD37). It is postulated that either the target molecules could not readily mediate signals when bound to MAbs and/or that the ability of the MAbs to crosslink their target molecules was poor.

The therapeutic potential of MAbs has not been fully realized because there has been no paradigm for predicting which properties of the MAb are essential and how MAbs interact with other therapeutic modalities. For example, until recently, it was believed that the antitumor activity of a MAb was due solely to its conventional immunological effector mechanisms (i.e., ADCC, C' fixation) (Dyer et al., 1989; Hale et al., 1984). Although this is true in certain instances, there is accumulating evidence that the antitumor activity of many MAbs is due to their ability to signal growth arrest to death (Trauth et al., 1989; Yefenof et al., 1993) or to their ability to inhibit cell traffic (Zahalka et al., 1993), cell-cell interactions (Zahalka et al., 1995; 25) or extravasation (Ruiz et al., 1993; Akiyama et al., 1995).

Recently it has been shown that MAbs can exert antitumor activity in other ways, e.g. by inhibiting metastases (Qi et al., 1995), tumor cell-substrata interactions (Guo et al., 1994), or tumor cell extravasation (Edward, 1995). In addition, it has been reported, that some MAbs can signal growth arrest and/or apoptosis of tumor cells, by acting as agonists ("negative signaling") (Ghetie et al.. 1992; Ghetie et al., 1994; Vitetta and Uhr, 1994; Trauth et al., 1989; Page and Defranco, 1988; Bridges et al., 1987; Funakoshi et al., 1994; Beckwith et al., 1991; Schreiber et al., 1992; Scott et al., 1985). "Negative signaling" is herein defined as the inhibition of cell growth by cell cycle arrest or the induction of apoptosis (programmed cell death). Indeed, in the case of B cell lymphoma, there is compelling evidence that both anti-idiotype (Levy and Miller, 1990; Hamblin et al., 1980)

and anti-CD19 MAbs (Ghetie et al., 1992; Ghetie et al., 1994) exert their anti-tumor activities predominantly, if not exclusively, by signaling growth arrest and apoptosis. Other MAbs which also have signaling properties include anti-Fas (Trauth et al., 1989), anti-CD40 (Funakoshi et al., 1994), anti-Class II MHC (Bridges et al., 1987), anti-Her-2 (Scott et al., 1991), anti-Le$^y$ (Schreiber et al., 1992) and anti-IgM (Vitetta and Uhr, 1994; Page and Defranco, 1988; Beckwith et al., 1991; Scott et al., 1985). Furthermore, negative signaling can sometimes be optimized by hypercrosslinking with secondary antibodies or by using "cocktails" of primary antibodies (Marches et al., 1996).

In the case of anti-CD 19, only a small percentage of MAbs can deliver growth inhibiting signals to neoplastic B cells and these require the addition of very large (i.e. hypersaturating) concentrations of antibody (Ghetie et al., 1994). Unfortunately, these large concentrations of antibody can activate unwanted immune responses which clear the therapeutic antibodies from the system and reduce the efficacy of treatment. Clearly, it is desirable to eliminate these unwanted immune responses in order to increase the efficacy of treatment, but to date, the means to eliminate these responses is not available.

The therapeutic or diagnostic usefulness of a monoclonal antibody (MAb) is dependent upon several factors. The MAb must possess sufficient binding affinity and a relatively high avidity for an antigen. The avidity of a MAb is based on the valency of the antibody (and the antigen) and the quaternary arrangement of the interacting components. The physical size of the molecule is also an important limiting factor. Thus while hundreds of MAbs recognize tumor antigens, few MAbs have proven useful for the diagnosis and treatment of tumors and neoplastic diseases, because they are not specific enough, they fail to have sufficient affinity or avidity or are too large to reach their antigens.

Part of the difficulty in designing antibody conjugates which possess sufficient affinity and avidity for tumor antigens and are of an appropriate isotype or subclass to efficiently initiate cell cycle arrest or apoptosis is that few MAbs possess sufficient affinity and avidity to be useful. For example, IgG molecules are monomers and have low valency; and thus, they have low avidity. IgM molecules have a higher valency but their size limits their ability to penetrate tissue and reach the desired antigenic target.

Homoconjugates of IgG molecules have been designed which possess increased valency and thus have higher avidity and are better able to promote effector function (PCT application WO92/04053; Wolff et al., 1992; 1993; Caron et al., 1992). But these homoconjugates possess two or more Fc regions; and thus, they can still elicit undesired immune responses which reduce successful treatment of a tumor or neoplastic disease. And although increasing their valency results in increased avidity, the physical sizes of the homoconjugates are also increased which may limit or even prevent them from being able to physically reach target epitopes.

There is a clear and present need for therapeutic MAbs with enhanced avidity which do not produce unwanted immune responses and are relatively small molecules which are capable of wide biodistribution. The present invention provides such compositions as conjugates of MAbs which do not possess an Fc region and yet are surprisingly active at signaling cell cycle growth arrest and/or apoptosis. The compositions of the present invention provide the further improvements of being relatively smaller than conventional conjugates of IgG MAbs, and are thus capable of wider biodistribution, and producing fewer unwanted immune responses because they do not signal effector functions.

SUMMARY OF THE INVENTION

The present invention provides conjugates of monoclonal antibodies (MAbs) which can lack Fc regions and yet are as effective, or possibly more effective, at signaling cell cycle arrest and/or apoptosis of tumor cells than comparable MAb conjugates which contain Fc regions. Surprisingly, conjugates of the present invention can be comprised of MAbs which in their monomeric or unconjugated form have little or substantially no anti-tumor activity, indicating that the binding to and crosslinking of cell surface antigens to the conjugates elicits a negative signal. Conjugates of the present invention are relatively smaller and capable of better biodistribution and, because they cannot recognize Fc receptors and stimulate effector function, these novel conjugates do not elicit unwanted immune responses.

The invention provides conjugates of two or more monoclonal antibodies, wherein the conjugates comprise at least one monoclonal antibody that does not comprise an Fc region. Conjugates comprise two, three, four or more monoclonal antibodies. In certain embodiments, no monoclonal antibody, comprised in any conjugate, comprises an Fc region. In further embodiments the conjugate comprises a monoclonal antibody that comprises an Fab or an Fv region or a fragment thereof.

The invention further provides a conjugate that comprises a monoclonal antibody that asserts substantially no antineoplastic activity, or even no anti-neoplastic activity, in an unconjugated form. The anti-neoplastic activity is an antiproliferative activity and preferably is expressed as signaling growth arrest or apoptosis (i.e., programmed cell death, PCD).

In one aspect of the invention the conjugate comprises a monoclonal antibody that is a tumor reactive monoclonal antibody. In one particular illustration of the invention, preferred conjugates comprise a monoclonal antibody that is an IgG, IgA, IgD or IgM monomer and particularly preferred monomers are mammalian monomers, such as murine or human monoclonal antibody monomers. Exemplary monoclonal antibodies include, but are not limited to, an anti-CD19, anti-CD20, anti-CD21, anti-CD22, anti-HER2, (for example, HER66, HER50 and HER164) Mabs which react with breast tumors, ovarian tumors, prostate tumors, and/or lung tumors.

In another aspect of the invention the conjugates comprise antibodies that are conjugated via hypercrosslinking. In further aspects, the antibodies are conjugated via one or more covalent bonds such as disulfide bonds, thioether bonds or other covalent bonds which may function in vivo. These can be genetically engineered bonds as well as chemically engineered or even a combination of genetically engineered recombinant bonds and chemical bonds.

In other embodiments of the invention, the conjugates also comprise other proteins which may also be dimerized either by recombinant, chemical or recombinant and chemical means.

In a preferred embodiment the conjugate has a valence of at least three. In a more preferred embodiment the conjugate has a valence of at least four and sometimes five.

In a particular embodiment of the invention the conjugate is a homoconjugate and in another embodiment the conjugate is a heteroconjugate. As used herein, "homoconjugate" refers to a conjugate comprised of a single species of monoclonal antibody and "heteroconjugate" refers to a conjugate comprising two or more different species of monoclonal antibodies.

The invention further provides a method of making a conjugate of two or more monoclonal antibodies that comprises obtaining a first monoclonal antibody that does not comprise an Fc region; obtaining a second monoclonal antibody; and conjugating the first monoclonal antibody to the second monoclonal antibody.

In a particular embodiment of the invention the first monoclonal antibody is a monoclonal antibody that asserts anti-neoplastic activity in a conjugated form. In a further embodiment of the invention the second monoclonal antibody is a monoclonal antibody that asserts anti-neoplastic activity in a conjugated form. In certain embodiments both the first monoclonal antibody and the second monoclonal antibody are monoclonal antibodies that assert anti-neoplastic activity in a conjugated form.

In one aspect of the invention the first monoclonal antibody is a monoclonal antibody that asserts substantially no anti-neoplastic activity in an unconjugated or monomeric form. In another aspect of the invention the second monoclonal antibody is a monoclonal antibody that asserts substantially no anti-neoplastic activity in an unconjugated or monomeric form. In still another aspect of the invention both the first monoclonal antibody and the second monoclonal antibody are monoclonal antibodies that assert substantially no anti-neoplastic activity in an unconjugated or monomeric form.

In yet another embodiment is provided a method further consisting of obtaining a third, or even a fourth, monoclonal antibody; and conjugating the third, or even fourth, monoclonal antibody to the conjugate.

The invention provides a method of signaling an anti-neoplastic activity that comprises obtaining a conjugate of two or more monoclonal antibodies, wherein the conjugate comprises a monoclonal antibody that does not comprise an Fc region and wherein the conjugate comprises a monoclonal antibody that asserts anti-neoplastic activity in a conjugated form; and contacting a neoplastic cell or tumor with the conjugate.

The invention further provides a method of detecting the presence of a neoplastic disease that comprises contacting a biological sample, that is suspected of comprising a neoplastic antigen, with a conjugate that comprises a monoclonal antibody and screening for an immunological reaction.

In an additional aspect the invention provides a pharmaceutical composition comprising a pharmaceutically acceptable carrier and a conjugate comprising a monoclonal antibody.

An "Fc region" is herein defined as that region of an immunoglobin (Ig) composed of the C-terminal half of the heavy chains including that part of the hinge region containing the inter-heavy chain disulphide bridges; which may be released enzymatically from the Ig molecule; and specifically recognizes and binds to an Fc receptor such that effector function, such as phagocytosis or inflammatory response, is expressed.

Thus it will be readily understood that, herein, a monoclonal antibody that lacks an Fc region comprises an antibody which does not stimulate effector function by binding to an Fc receptor. The hinge regions of Igs vary considerably in length; thus, it is contemplated that a monoclonal antibody lacking an Fc region may contain a fragment of Fc region of almost any intermediate length such that effector function is not expressed in the presence of an Fc receptor.

Alternatively, mutations or alterations to an Fc region may be introduced such that the length of the Fc fragment is about equivalent to the native Fc region but the altered Fc fragment cannot stimulate effector function in the presence of an Fc receptor. In certain embodiments, the preferred length of hinge region is preferably being limited by the ease of preparation and use in the intended conjugation protocol.

It will be readily understood that "intermediate lengths", in these contexts, means any length between the quoted ranges, such as 1, 2, 3, 4, 5, 6, 7, 8, 9, 10, 11, 12, 13, 14, 15, 16, 17, 18, 19, 20, 21 22, 23, 24, 25, 26, 27, 28, 29, 30, 31, 32, 33, 34, etc.; 50, 51, 52, 53, etc.; 70, 71, 72, 73, 74, 75, etc.; 100, 101, 102, 103, etc.; 120, 121, 122, etc.; 140, 141, 142, etc.; including all integers through the 1–150 ranges, and the like.

The antibodies used to prepare the conjugates of the present invention may be obtained by immunizing an animal with a mammalian, preferably a murine, or even more preferably a human protein or peptide that comprises a tumor antigen, and collecting the resultant antibodies. The protein or peptide comprising the tumor antigen may be prepared by obtaining a sample comprising the tumor antigen from any national or international registry which maintains tumor and cancer cell lines, such as the National Cancer Institute Tumor Registry, and using methods well-known to those of skill in the art. The Mabs can be prepared by phage display, cloning of cDNAs or any other molecular biological techniques.

What is meant by a monoclonal antibody having "substantially no anti-neoplastic activity" is that any activity that is detected, as measured by $^3$H-thymidine inhibition as described herein, is not statistically significant (as determined, for example, by the Student t test) when compared to a control. What is meant by a monoclonal antibody having "no anti-neoplastic activity" is that no activity is detected by $^3$H-thymidine inhibition, as described herein.

It will be understood that by "neoplastic" is meant a tumorous condition which may comprise diffuse or well-differentiated tumor cells and affect reproductive tissue, such as ovaries, breast, testes, neural tissue, the alimentary tract, lymph tissue, bone marrow, lung, prostate, liver or any other type of tissue subject to neoplastic diseases.

Those of skill in the art will recognize that a wide variety of epitopes may be expressed by neoplastic or cancer cells as discussed by DeVita et al. In *Cancer: Principles and Practice of Oncology*, Fourth edition, Lipincott, Philadelphia, 1993. It will be further understood that any monoclonal antibody that recognizes such epitopes are useful in the present invention. A listing of many of these monoclonal antibodies may be found in the American Type Culture Collection: Catalogues of Animal Viruses and Antisera, Chlamydiae and Rickettsiae (Rockville, Md., USA), incorporated herein by reference. Additional monoclonal antibodies may be isolated by following the protocols described herein and using a tissue or cell line obtained from any national or international tumor registry, such as the National Cancer Institute Tumor Registry.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2F) and BT474 cells (FIG. 2E and FIG. 2G): (FIG. 2A) HD37 anti-CD19; (FIG. 2B) RFB4 anti-CD22; (FIG. 2C) 3H7 anti-CD20; (FIG. 2D) B-ly4 anti-CD21; (FIG. 2E) HER-50 anti-Her-2; (FIG. 2F and FIG. 2G) 3F12 ($IgG_1$-isotype matched) Daudi cells at $5\times10^4$ cells/100 ml in RPMI 1640 medium containing 10% FCS, glutamine and antibiotics were distributed into triplicate wells of 96-well microtiter plates containing 100 ml of antibodies (monomer or dimer) diluted in the same medium at concentrations ranging from $10^{-8}$–$10^{-6}$ M. The plates were incubated for 24–48 h at 37° C. in 5% $CO_2$ and pulsed for 4 h with 1 mCi[$^3$H]-thymidine (Amersham, Arlington, Va.). Wells were harvested on a Titertek cell harvester (Flow Labs, Rockville, Md.) and the radioactivity retained on Skatron filters was determined in a liquid scintillation spectrometer. BT474 cells at a concentration of $10^4$ cells/100 µl in MEM containing 10% heat-inactivated fetal calf serum (FCS), 2 mM L-glutamine, 100 nM non-essential amino acids, 1 mM sodium pyruvate and 2% vitamins for MEM were plated into triplicate wells of 96-well microtiter plates and allowed to adhere overnight. The cells were then treated with 100 µl antibodies diluted in the same medium in varying concentrations. The plates were incubated for 72 hours at 37° C. in 5% $CO_2$ and pulsed for 6 hours with 1 µCi $^3$H-Thymidine (Amersham). The percent reduction in [$^3$H]-thymidine incorporation, as compared with untreated controls, was used to quantitate killing. Nine wells of untreated cells were included in each study plate as controls. Graphs represent 3–7 studies that were carried out.

FIG. 5A and FIG. 5B—Cell cycle analysis (FACS) of Daudi cells incubated with HD37 monomers or dimers vs. no treatment. (FIG. 5A) $1\times10^6$ Daudi cells, were incubated for 24 hours at 37° C. either with media (control) or with different MAbs, washed twice with 10% FCS-containing RPMI-1640 media and the cell pellet was treated with 50 µL of 400 µmol/L 7-AAD, and incubated on ice for 30 minutes (7-AAD acting as a vital dye). Cells were then fixed (1.0 ml of 0.5% paraformaldehyde in PBS), and simultaneously permeabilized and stained with the Hoechst dye (220 µL of Hoechst at 10 µg/ml in 5% Tween-20) overnight at 4° C. After filtration through a 50 µm nylon mesh, samples were analyzed on a dual laser/pulse processor-equipped FACStar (Becton Dickinson, San Jose, Calif.) ($10^5$ cells/analysis). After gating on single, viable cells (viable cells are 7-ADD-negative and aggregates were excluded using an area-versus-width plot of the Hoechst signal) the percent of cells in each stage of the cell cycle was determined using the Paint-A-Gate plus data analysis program (Becton Dickinson, Immunocytometry Systems). A representative study of three is shown. (FIG. 5B) $1\times10^5$ BT474 cells were plated out in 1 ml media and allowed to adhere overnight at 37° C. The cells were then treated with medium alone, or 50 µl medium containing 10 µg of antibody. Cells were incubated with antibody for 2 hours and then were trypsinized, washed twice in cold PBS, and stained simultaneously with Annexin V-FITC and propidium iodide for 15 minutes at 25° C. The samples were then analyzed for surface expression of phosphotidyl serine and propidium iodide exclusion on a FACScan (Becton Dickinson, San Jose, Calif.). This is a representative study of three carried out as shown.

(FIG. 6A) The dissociation of HD37 monomers (○) and dimers (●) from Daudi cells. Daudi cells ($1\times10^7$/ml) were incubated with a concentration of $^{125}$I-$IgG_1$ (either monomer or dimer, in a volume of ~4 ml of complete RPMI medium at 4° C.) that occupied at least half of the binding sites at equilibrium in a 15-ml tissue culture tube. This amount was sufficient for 10 duplicate time points. A duplicate reaction mixture containing a 200-fold molar excess of unlabeled antibody was also prepared. The reaction mixtures were incubated at 4° C. with slow shaking on a platform shaker until equilibrium was achieved (as determined from the association studies, 2 hrs. was sufficient). To prevent internalization, the cells were maintained at 4° C. After a 2 h incubation the cells were centrifuged in a tabletop centrifuge for 5 min. at 1000×g, 4° C. To initiate the dissociation of antibody from the cell surface, cells were washed at 4° C. with cold complete RPMI medium, resuspended in 4 ml complete medium, and incubated on ice for the final step. At various time points (0, 1, 4, 8, 24, 48, 72, 96, 120 h) duplicate aliquots of the cell suspension were removed, centrifuged through binding-oil columns, and the specific cell-bound radioactivity was determined. The dissociation rate (Kd) was measured by plotting In (B) versus time where B represents bound cpm. The time point at which 50% of the protein bound to the cells was dissociated, was calculated from the curve. This is one of two studies carried out; The internalization of $^{125}$I-radiolabeled HD37 monomers (FIG. 6B) and dimers (FIG. 6C) into Daudi cells. Samples of $10^6$ cells were pelleted by centrifugation at 4° C., supernatants were aspirated and the radioactivity in both the pellet and supernatant were measured. Surface-bound antibody was then removed by a 10 min. incubation in RPMI complete medium acidified with 1 N HCl to pH 2.5. Then cells were sedimented and the supernatant and sediment were measured. After stripping off the surface $^{125}$I-IgG, the radioactivity in the cell pellet represented the internalized ("acid-resistant") radiolabeled antibody. All supernatant fractions collected were then analyzed by TCA precipitation. The fraction of antibody bound to cell membranes and that internalized into the cells were compared; (○) $R_{BC}$-bound to cell; (●) $R_m$-bound to membrane; (▽) $R_I$-internalized; and (▲) $R_R$-released. This is one of two studies carried out.

Ghetie et al., 1988). This is a representative study of three carried out. (See description of FIG. 2 for details).

Figure 8:
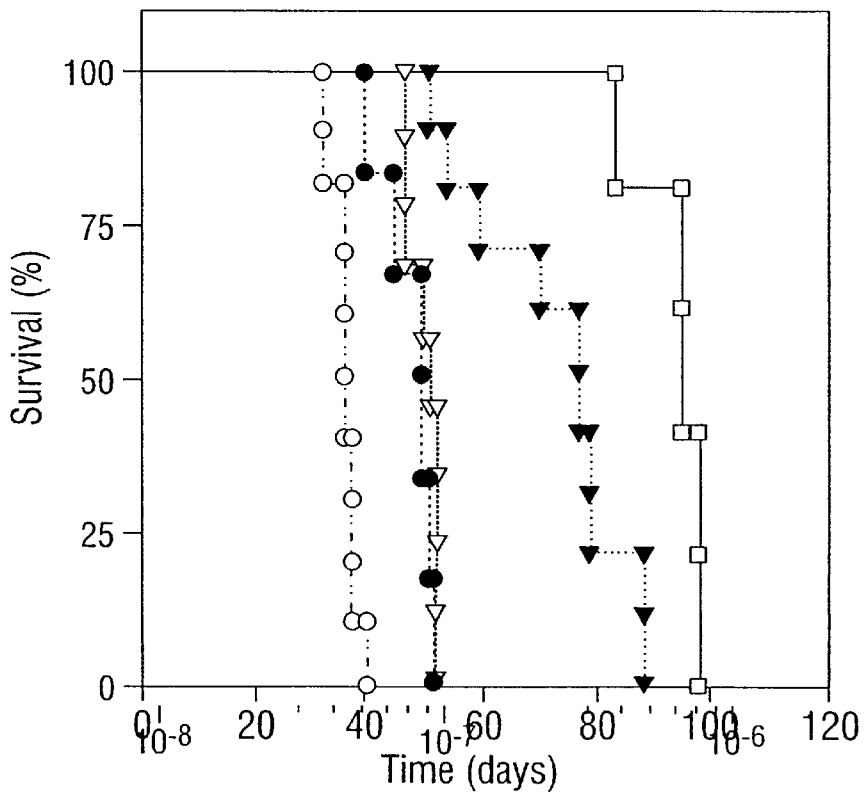

FIG. 8—Survival of SCID/Daudi mice treated with HD37 monomers or dimers±Doxorubicin. SCID mice were inoculated i.v. with 5×10$^6$ Daudi cells. One day after tumor cell inoculation, the following treatments were given to groups of 5–7 mice: Control (injected with saline) (○); mice treated with doxorubicin (80 μg/mouse) (●); mice treated with HD37 monomer (1 mg) (ρ); mice treated with HD37 dimer (1 mg) (θ); mice treated with both, HD37 dimer (1 mg) and doxorubicin (80 μg) (□). Agents were injected i.v. in 4 equal doses on days 1–4 after tumor inoculation. This represents the averages of two studies.

Figure 9:
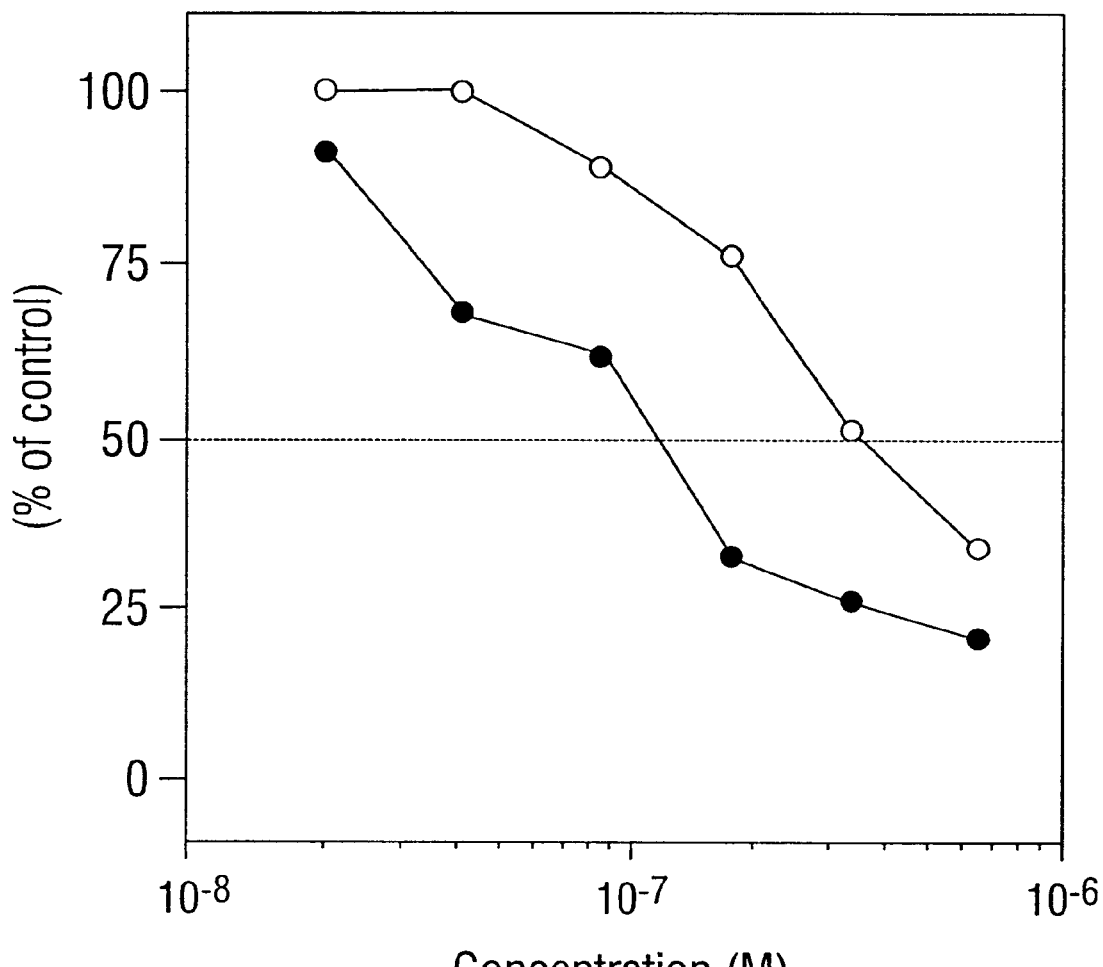

FIG. 9. Direct cytotoxic effect of anti-HER/2 dimers on BT474 cells using a [$^3$H]-thymidine incorporation assay. Anti-HER/2 dimers of IgG, (○), had an IC$_{50}$ of 3.5×10$^{-7}$ M and anti-HER/2 dimers of F(ab')$_2$, (●), had an IC$_{50}$ of 1.1×10$^{-7}$ M. Data presented are the average of two independent studies with limited standard deviations.

Figures 10A, 10B, 10C:
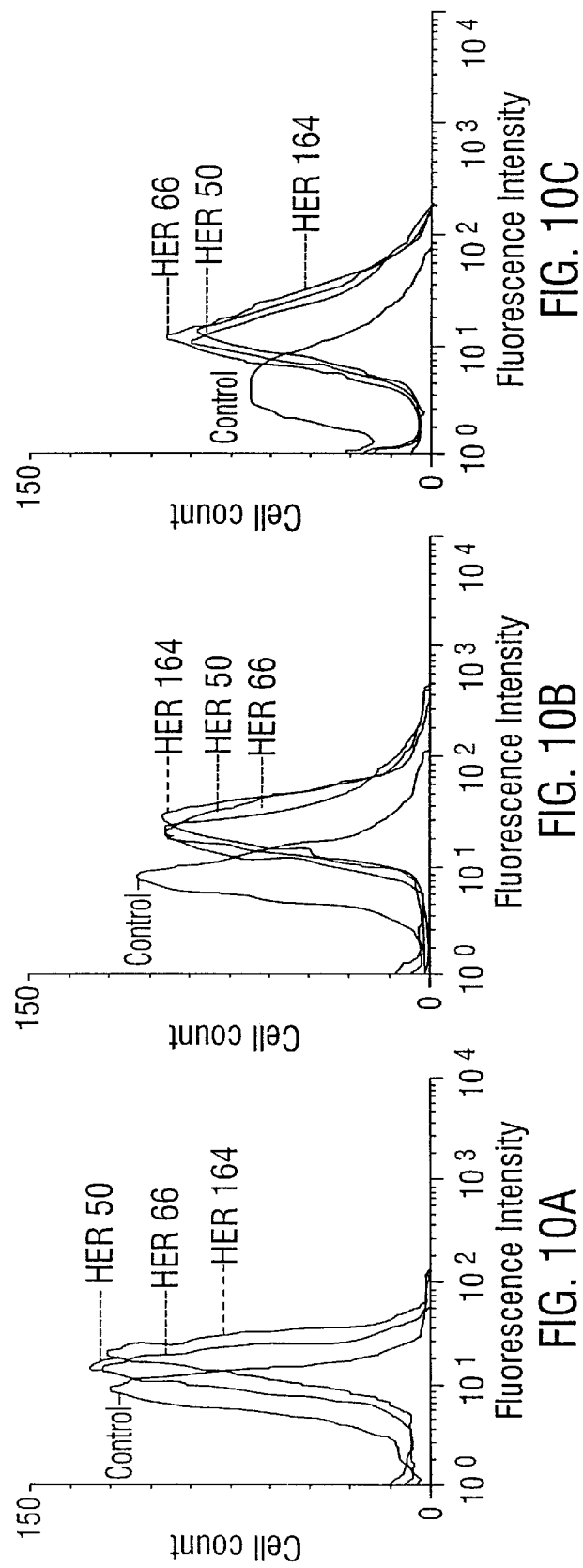
Figure 11B:
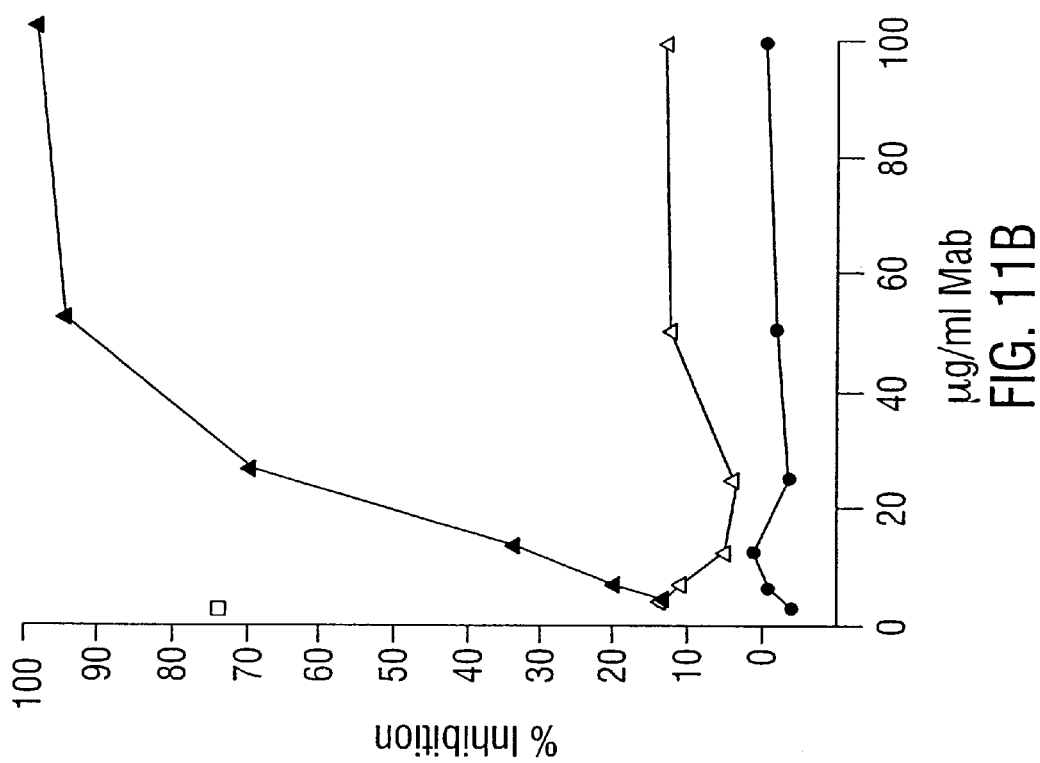
Figure 11A:
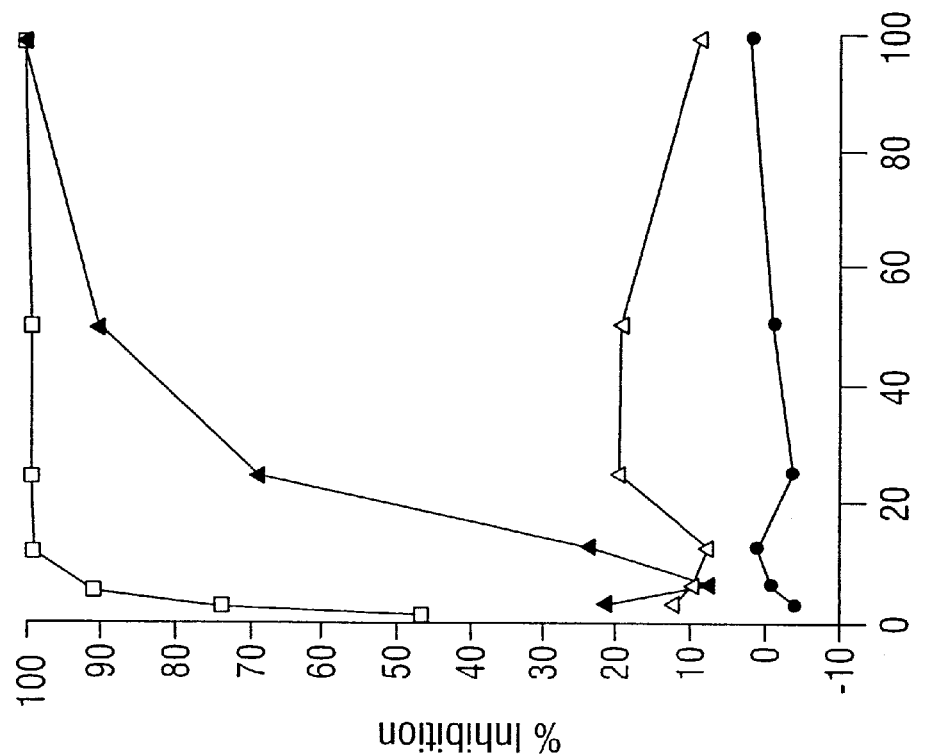

FIG. 10A–FIG. 10C. Expression of Her-2 (as measured using fluorescence to determine cell count) on different prostate carcinoma cell lines. Cell line=PC3 (FIG. 11A); LNCAP (FIG. 11B); Du 145 (FIG. 11C).

FIG. 11A–FIG. 11B. The inhibitory effects of anti-HER2 Mabs, HER-66 (FIG. 10A) or HER-50 (FIG. 10B) monomers and dimers on prostate LNCaP cells. Cells were plated for 16 hours in medium. The Mabs were added for 48 hours and the plates were then pulsed for 4 hours with $^3$H-thymidine. Cells were harvested and the radioactivity determined. The control is an isotype-matched Mab. —△— Mab monomer; —▲— Mab dimer; —●— control dimer; —□— F(ab)'2 dimer.

DESCRIPTION OF ILLUSTRATIVE EMBODIMENTS

The inventors have explored the mechanisms by which antibodies against molecules in the B cell receptor (BCR) complex induce growth arrest in lymphoma cells.

Using MAbs against mIgM and CD19, the roles of epitope recognition, valency and crosslinking in the delivery of negative signals (apoptosis and CCA) to cells has been studied. MAbs which worked optimally were utilized in the SCID/lymphoma model, both alone and in conjunction with chemotherapy and immunotoxins (ITs). The inventors established that combinatorial strategies are essential to cure mice of advanced lymphoma.

The results of these investigations established the following: 1) It appears that those MAbs which can negatively signal the growth of lymphoma cells in vitro have antitumor activity in vivo. Hence, in vitro results are predictive of in vivo results, at least in the SCID/lymphoma model (Ghetie et al., 1992); 2) Even if a MAb induces only CCA, combinations of CCA-inducing antibodies and apoptotic MAbs result in greater apoptosis in vitro (Marches et al., 1996); 3) Hypercrosslinking of cell surface molecules is critical for some MAbs to signal growth arrest in tumor cells (Marches et al., 1996). Importantly, both HD37 (anti-CD19) and RDB4 (anti-CD22) signal as dimers and not as monomers.

The inventors considered dimers of other antibodies (which do not signal optimally as monomers) in order to determine whether increasing their valency/crosslinking would increase their negative signaling. It should be noted that neither the HD37 MAb or the anti-Her2 MAb, HER70 requires an Fc fragment to signal either in vitro or in vivo (Ghetie et al., 1992). Therefore, the inventors considered the possibility that dimers could be digested to eliminate the Fc fragment to avoid Fc receptor binding in vivo or that multimers of recombinant Fvs could be generated once the preference MAbs had been selected.

On the other hand, it is possible that an appropriate isotype of a signaling antibody may enhance significantly its efficacy and that the dissociation rate ($T_{1/2}$) of the antibody in serum may play a major role in its efficacy. For example, there is ample evidence that ADCC can be effective against a variety of tumors (Hale et al., 1985; Chokri et al., 1992). 5) Thus far, anti-μ is the only antibody studied which can induce apoptosis in lymphoma cells (Racila et al., 1995; Scheuermann et al., 1994) and for reasons well known to those skilled in the art, it cannot be used therapeutically in humans who have serum IgM. For this reason, the inventors investigated the strategy of using other B cell receptor-associated (BCR) molecules as targets for MAbs and in particular CD79 (Igα and Igβ) Mabs to induce apoptosis.

The present invention provides significant insight into new and better ways to use MAbs therapeutically, why and how they act, and what strategies can be employed to use them successfully. These strategies will help to guide the design of future clinical trials.

Effect of the Epitope Specificity of Antibodies on CCA and Apoptosis in Daudi Cells.

The ability of polyclonal antibodies (PAbs), in contrast to MAbs, to induce apoptosis must result from different characteristics between the two antibodies. For example, since MAbs recognize only one epitope, their ability to crosslink a molecule on the cell surface is typically less than that achieved with PAbs which can crosslink several epitopes. In addition, PAbs may contain antibodies which recognize those epitopes which allow more effective crosslinking. If so, these postulated "PAb epitopes" may not have been recognized by the MAbs that were used in the aforementioned studies.

In order to distinguish between the mechanisms involving epitope specificity and "extent" of crosslinking, a panel of MAbs recognizing different nonoverlapping epitopes on mIgM were examined for their ability to inhibit growth of the human Burkitt's lymphoma cell line, Daudi.

As shown in Table 1 (Marches et al., 1996), none of the four MAbs alone was able to induce significant CCA or apoptosis. However, when three MAbs specific for three noncrossreactive epitopes (on Cμ1, Cμ2 and Cμ4) were combined, there was increased CCA and apoptosis. It, thus, appears that the extent of crosslinking and not the epitopes recognized per se is important in the antibody-mediated induction of negative signals. This result also has important practical implications since the absence of a negative antitumor effect of a signaling MAb does not exclude its potential when admixed with other MAbs specific for different noncrossreactive epitopes on the same molecule.

TABLE 1

Cell Cycle Status and Viability of Daudi Cells Treated with Anti-IGM Monoclonal Antibodies

| Treatment | % of Viable Cells in S-$G_2$-M | % Apoptotic |
|---|---|---|
| None | 61.0 ± 0.3 | 5.8 ± 1.2 |
| MAHCµ1 | 61.5 ± 0.6 | 5.3 ± 0.1 |
| MAHCµ2 | 57.6 ± 2.5 | 6.9 ± 0.6 |
| MAHCµ4 | 63.9 ± 1.7 | 5.8 ± 0.8 |
| MAHCµ | 59.2 | 7.8 |
| MAHCµ1 + MACHµ2 + MAHCµ4 | 37.0 ± 2.6 | 17.7 ± 3.5 |

$10^6$ Daudi cells per ml were incubated for 24 h with 10 µg of antibodies individually or in a combination at 3.3 µg each.

Effect of Hypercrosslinking IgM on Lymphoma Cells.

Figure 1A:
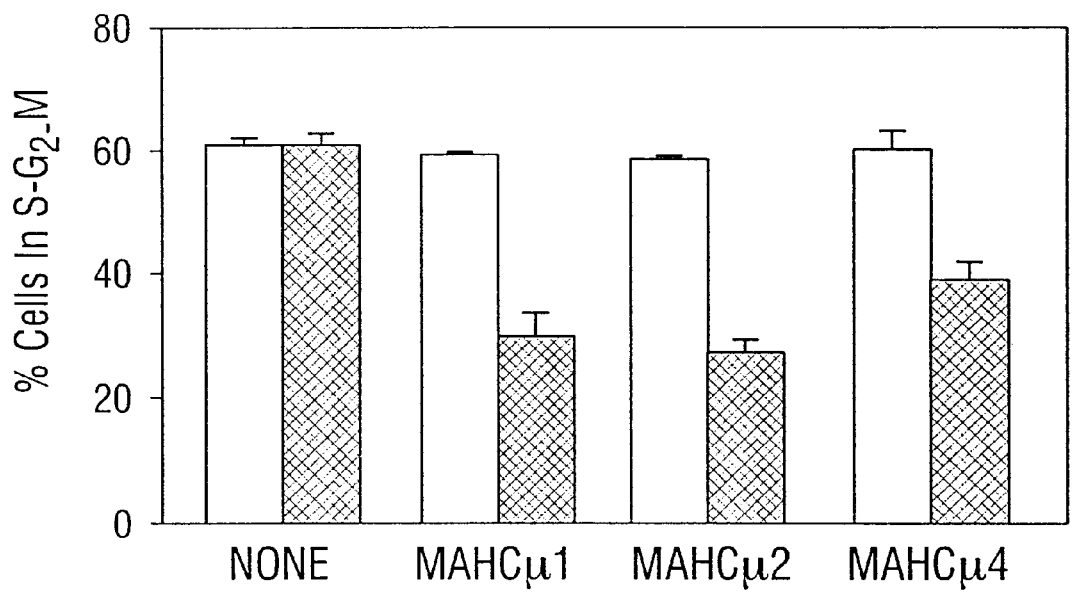
FIG. 1A–FIG. 1B. The effect of hypercrosslinking monoclonal anti-Ig antibodies on Daudi cells. $10^6$ cells/ml were coated with saturating concentrations (10 mg/ml) of antibodies for 15 min. at 4° C., washed and incubated in the presence or absence of GtAMIg (10 mg/ml) for Daudi cells treated with mouse monoclonal antibodies. Twenty-four hours later, the cells were harvested and stained. The percentage of viable cells in the combined S, $G_2$, and M phases of the cell cycle is shown in FIG. 1A and the percentage of apoptotic cells is shown in FIG. 1B. unshaded, no secondary antibody; shaded, plus secondary antibody.
Figure 1B:
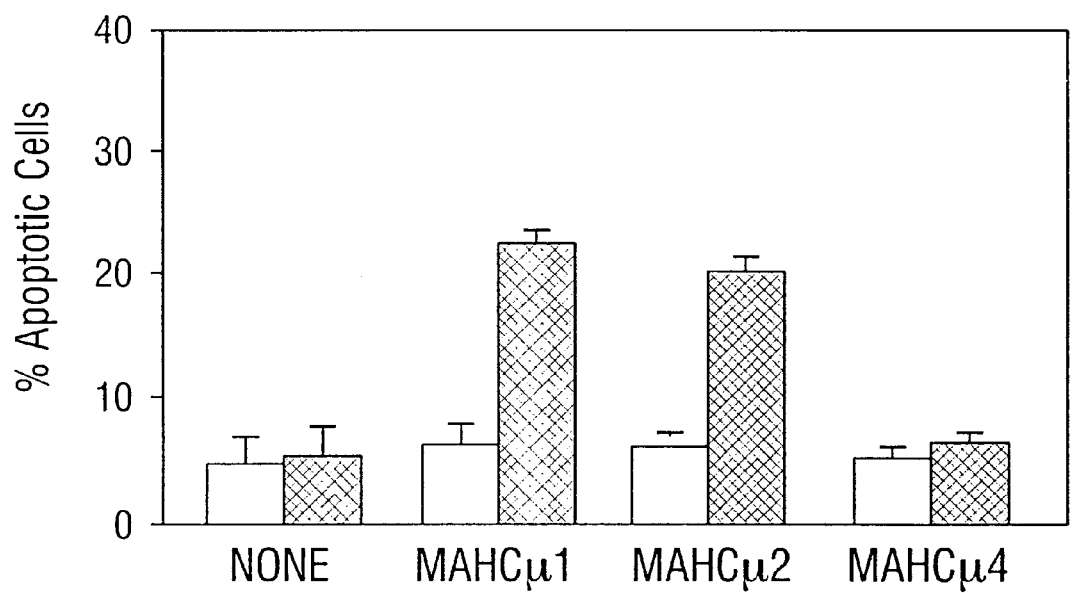
Figure 2A:
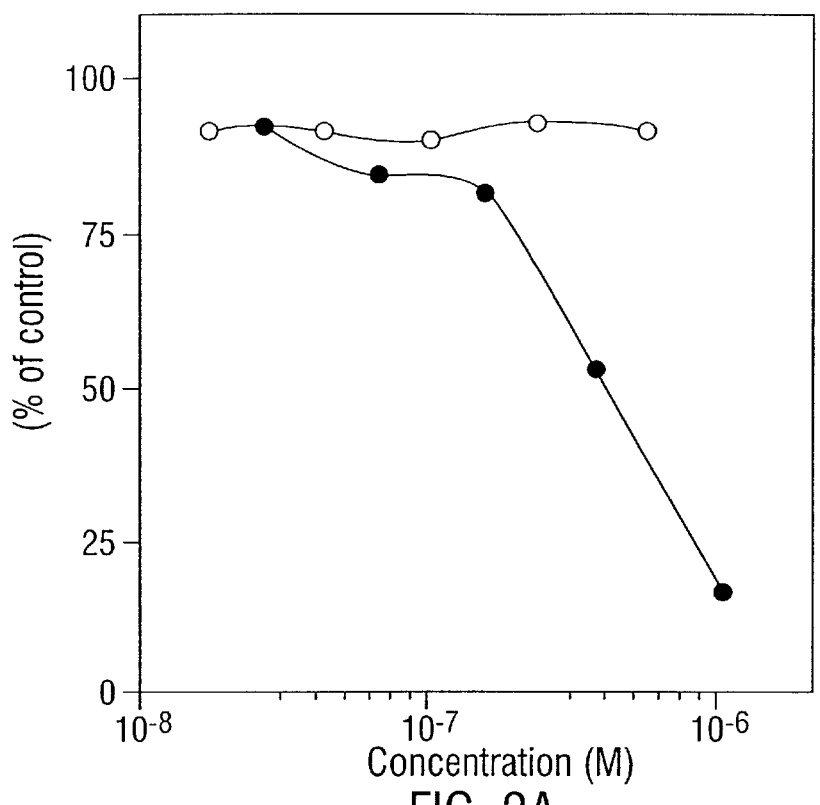
FIG. 2A–FIG. 2G—The anti-proliferative effect of different MAbs monomers (open symbol) or dimers (solid symbol) on Daudi (FIG. 2A–FIG. 3D.
Figure 2B:
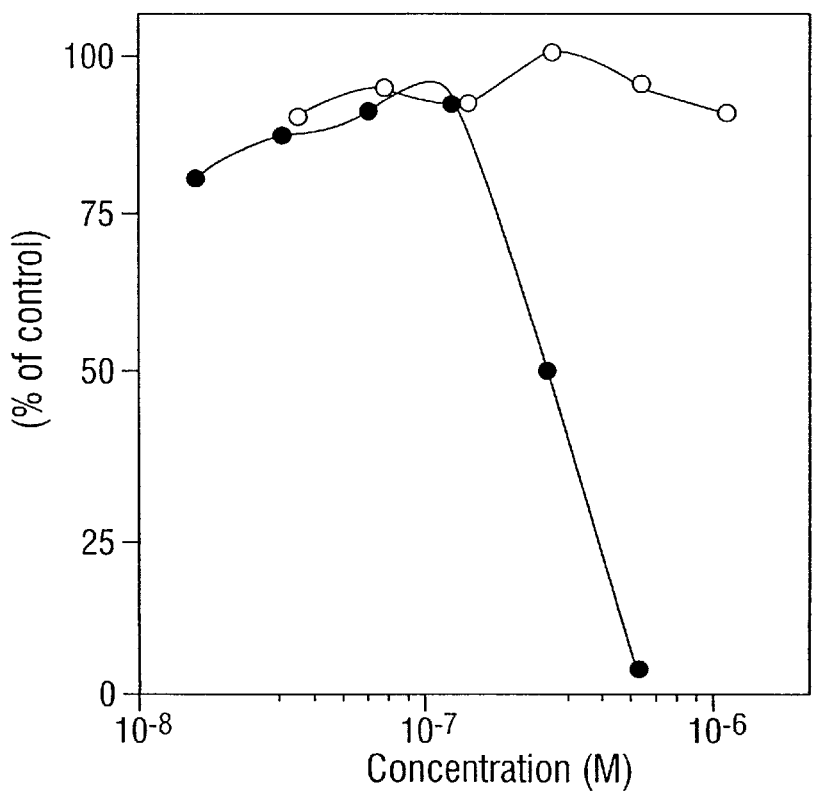
Figure 2C:
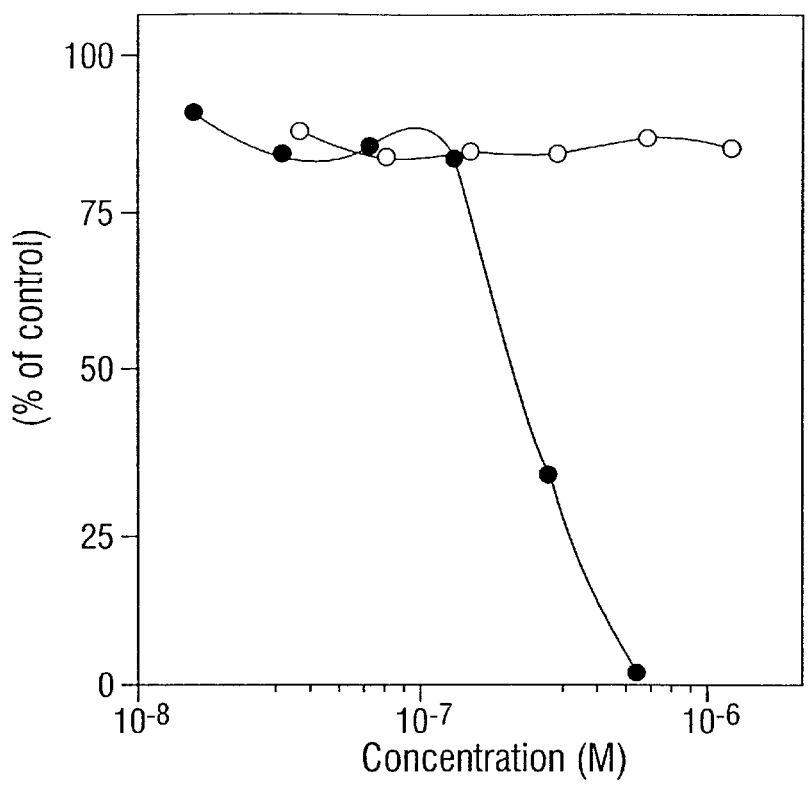
Figure 2D:
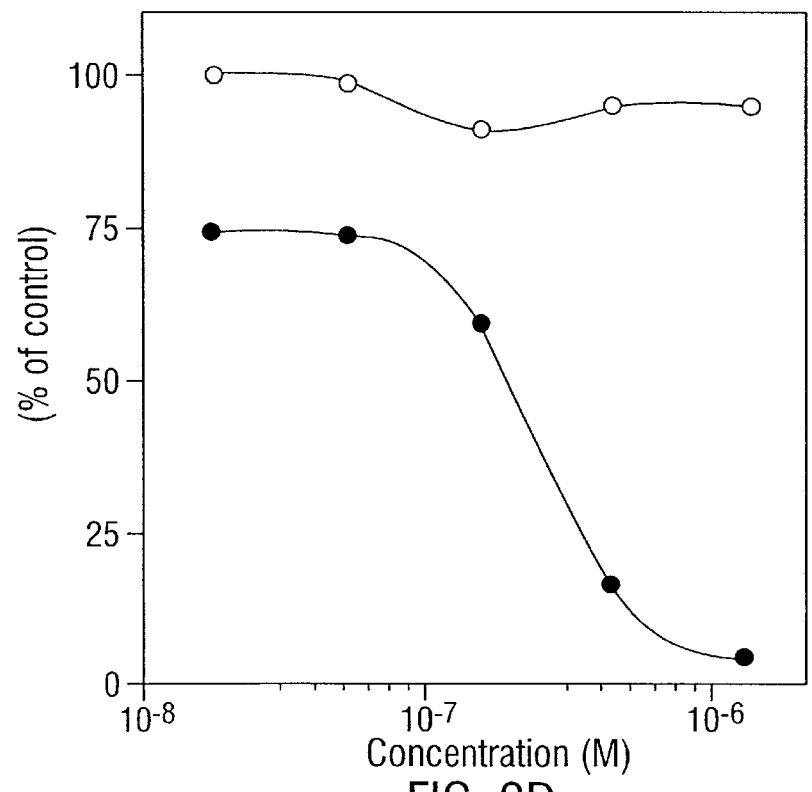
Figure 2E:
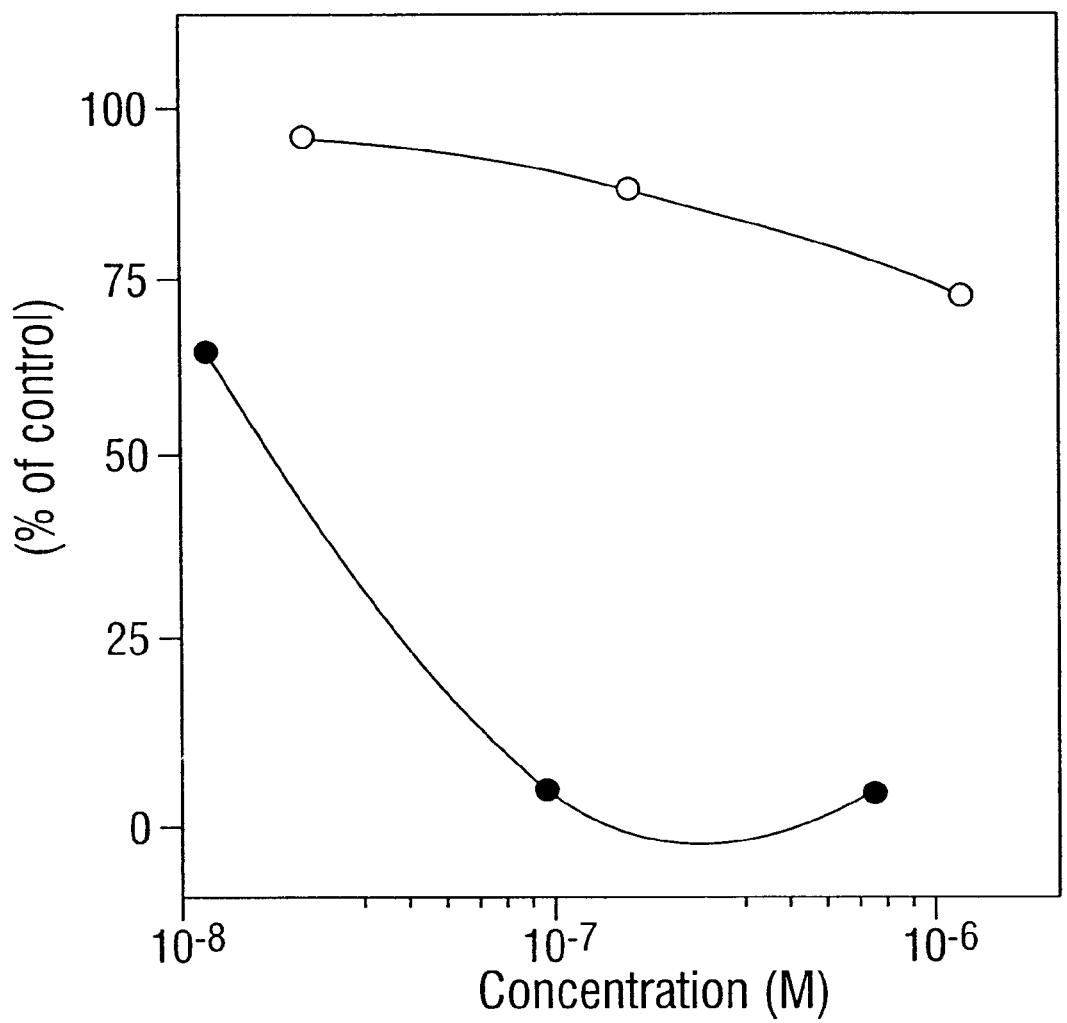
Figure 2F:
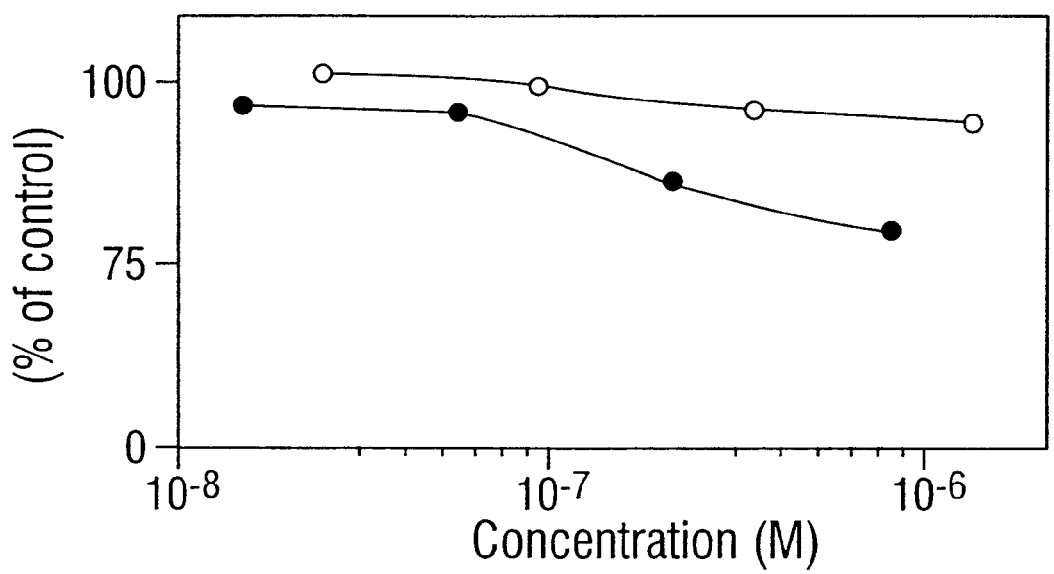
Figure 2G:
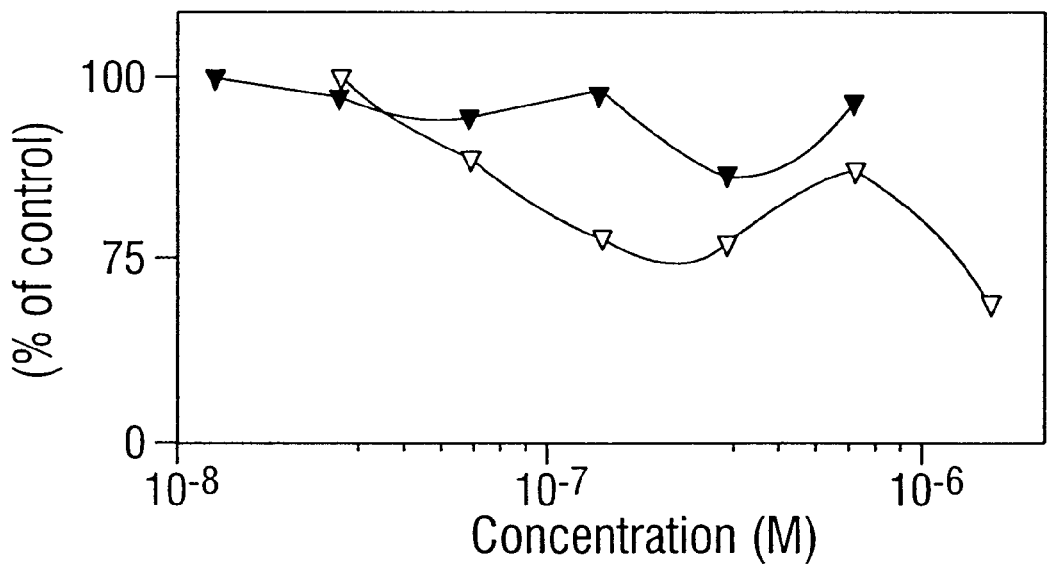
Figure 3A:
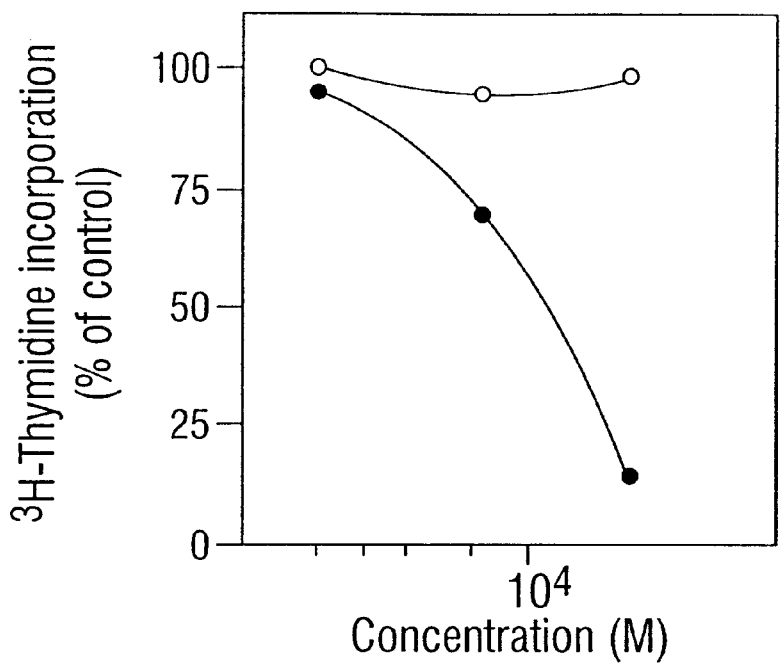
FIG. 3A–FIG. 3F. The cytotoxic effect of HD37 monomers (open) and dimers (closed) on different cell lines. FACS analysis of the cell lines showed that Burkitt's (Jiyoye) cells (FIG. 3A) were 97.6% positive, MFI=202; Diffuse hystiocytic cells (DHL-4) (FIG. 3B) were 99.9% positive, MFI=378; Pre-B CELLS (HPB-Null) (FIG. 3C) were 93.6% positive, MFI=162; Lymphoproliferative cells (LPD 16.10) (FIG. 3d) were 95.5 % positive, MFI=499; and Large cell (RPMI 1788) (FIG. 3E) were 96.6% positive, MFI=213 where Daudi cells AIDS (St486) (FIG. 3F) were 99.7% positive, MFI=680.
Figure 3B:
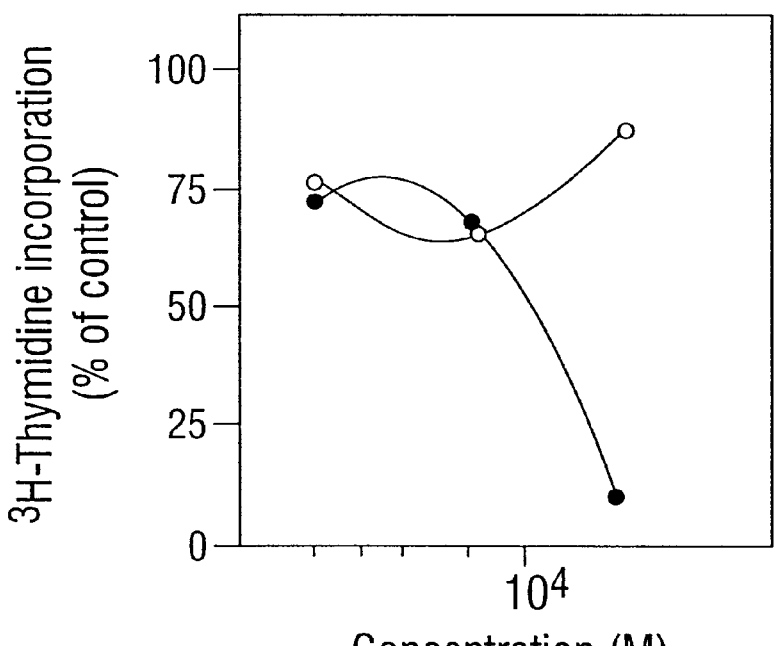
Figure 3C:
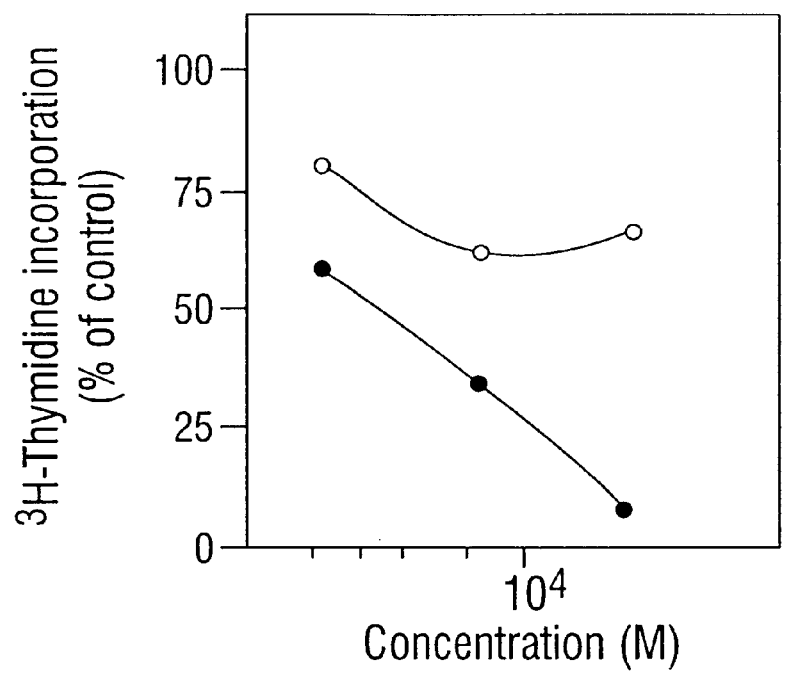
Figure 3D:
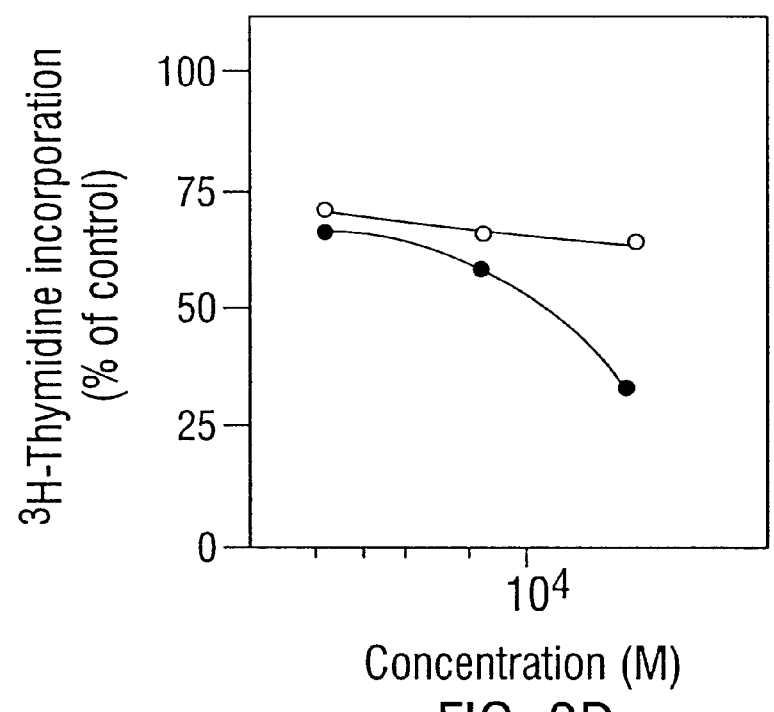
Figure 3E:
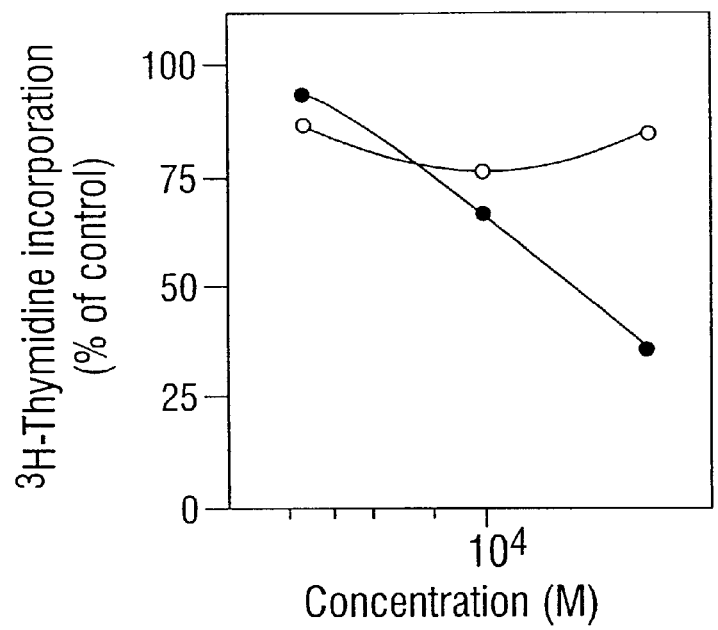
Figure 3F:
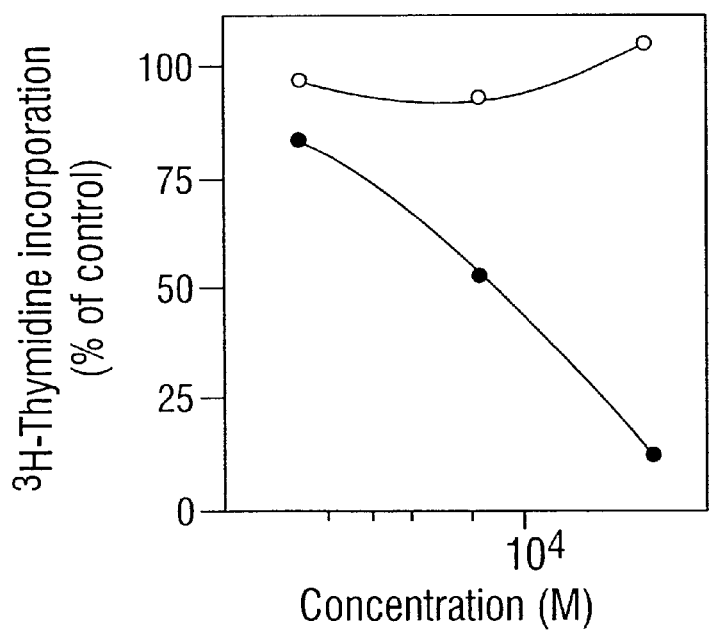

The above results suggested that if an MAb which signaled weakly were further crosslinked by a second layer of antibody, the negative effects (and, in particular, apoptosis) might be further increased. To examine this hypothesis, Daudi cells were incubated with various mouse monoclonal anti-µs, excess antibody was removed, and GAMIg was then added. The effects of this hypercrosslinking on the induction of CCA and apoptosis are shown in FIG. 1A and FIG. 1B. Again, individual anti-human µ MAbs by themselves were not effective at inducing apoptosis or CCA. However, after hypercrosslinking, virtually all the antibodies, except MAHCµ4, induced a significant increase in both CCA and apoptosis.

Hypercrosslinking and Kinase Activity

Although it is not feasible to use multiple layers of MAbs and PAbs to crosslink in vivo, the inventors have found that the affinity-purified anti-CD19 signaling antibody, HD37, usually contains about 80% monomers (IgG)$_1$ and 20% homodimers (IgG)$_2$. When the natural dimers were separated from the monomers, it was found that all the negative signaling in vitro could be attributed to the dimers (Table 2). Dimers were then prepared by chemically crosslinking monomers and these were tested in vitro. As shown in FIG. 2A–FIG. 2G, the "artificially prepared" (crosslinked) dimers of several MAbs were highly effective at decreasing [$^3$H]-thymidine incorporation. These results are important because they suggest that it is possible to improve the negative signaling capacity of MAbs which already display efficacy. In addition, multimers of "non-signaling" antibodies which do not naturally form dimers might also be therapeutically useful. As shown in FIG. 3A–FIG. 3F, when HD37 homodimers were used on representative cell types from a panel of lymphomas, similar effects were observed.

TABLE 2

Cytotoxic Effect of HD37 Antibody on Daudi Cells

| ANTIBODY | $IC_{50}$ (M' $10^{-7}$) | |
|---|---|---|
| HD37$^a$ (80% monomer + 20% homodimers) | 24.0 ± 0.4 | (4)$^c$ |
| HD37 monomer$^b$ | >70.0 | (3) |
| HD37 dimer$^b$ | 5.2 ± 3.6 | (3) |

$^a$This antibody contained 20% natural dimer, which had formed after storage at 4° C.
$^b$The antibody above was purified by HPLC and the two fractions (monomer and dimer) were used for killing assay in Daudi cells.
$^c$Number in parenthesis is the number of studies performed.

Figure 4:
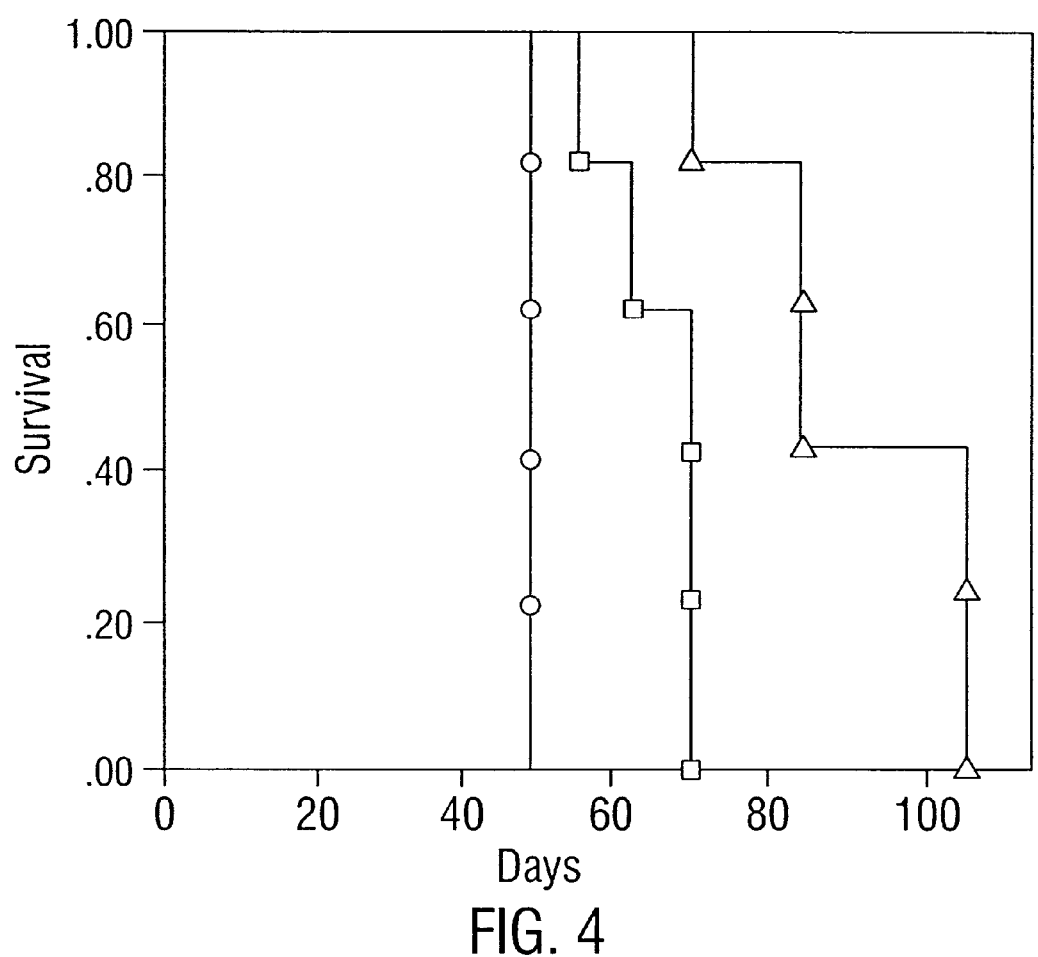
FIG. 4. Survival of SCID/Daudi mice treated with HD37 antibody crosslinked. SCID mice were inoculated intravenously (i.v.) with $5\times10^6$ Daudi cells. One day after tumor cell inoculation, the treatment with 1 mg HD37 monomer or chemically prepared dimers was initiated. The dose was given in four equal parts i.v. on Days 1–4 after tumor injection. Comparison of survival curves was carried out using log-rank and Wilcoxon tests (Kalbfleisch and Prentice, 1980). The median survival time (MST) of mice, shown in the tables, was calculated by the log-rank test at the 5% significance level. Dimer vs. monomer: p=0.026. ○, control; ■; monomer; Δ, dimer.
Figure 6A:
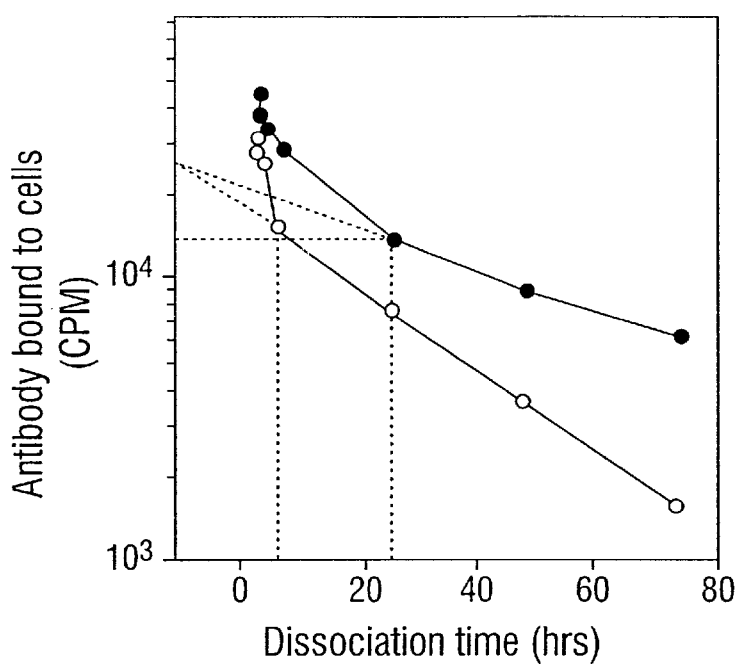
FIG. 6A–FIG. 6C.
Figure 6B:
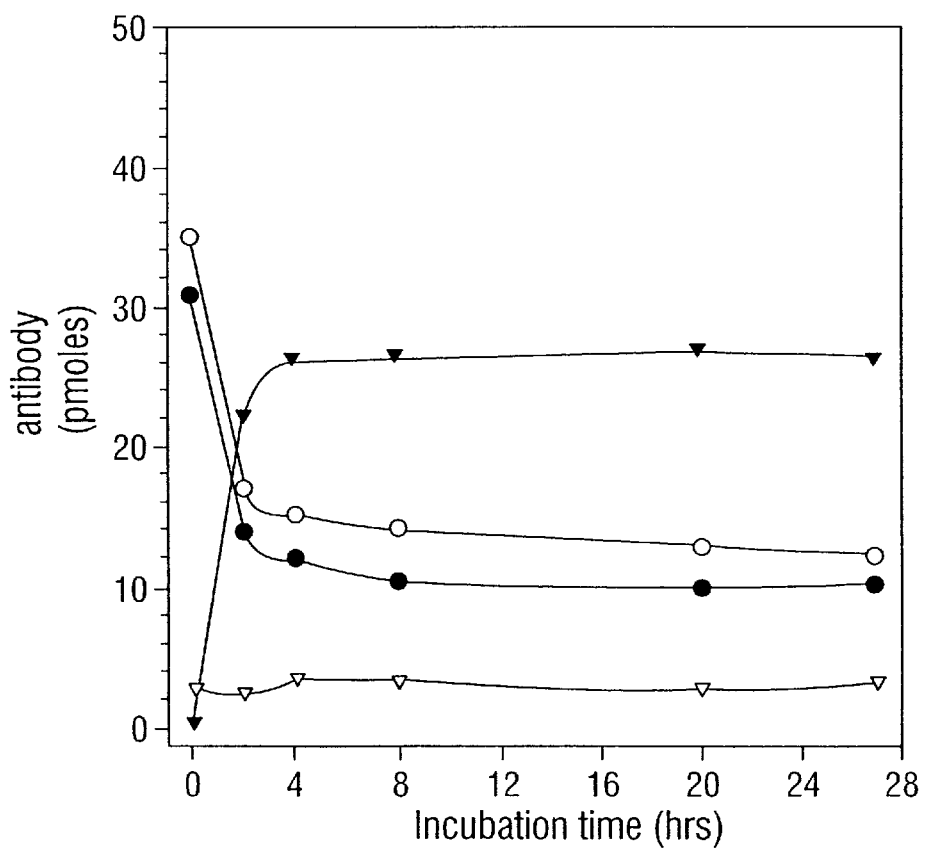
Figure 6C:
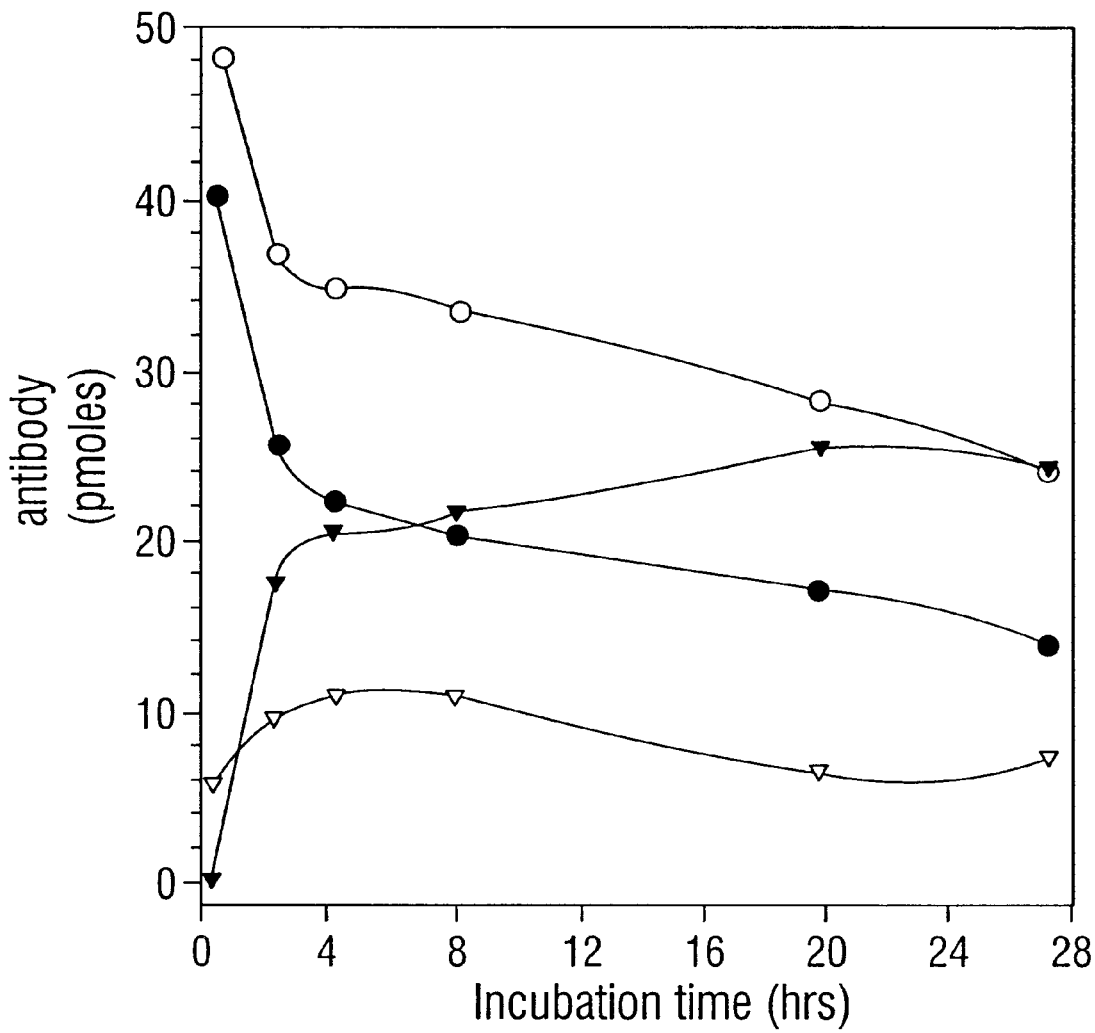

In other studies using HD37, it was found that HD37 (IgG)$_2$ has moderately better antitumor activity in SCID/ Daudi mice than HD37 (IgG)$_1$ (FIG. 4). The nature of the negative signaling by HD37 (IgG)$_2$ in vitro was studied in parallel. It appears that HD37 (IgG)$_2$, as compared to HD37 (IgG)$_1$, arrests more cells in the $G_0/G_1$ stage (FIG. 6). The invention also comprises the possibility of creating heterodimers or tetramers using MAbs of different specificities.

It has already shown that a combination of chemotherapy and ITs can cure SCID/Daudi mice under conditions where neither agent alone works (Ghetie et al., 1994b). It has also been shown that an IT against CD22 and large quantities of HD37 antibody (even as a F(ab')$_2$ fragment) can cure SCID/Daudi mice (Ghetie et al., 1994a). It should be noted that only 20% of HD37 is dimeric, thus accounting for the larger quantities needed. As shown in FIG. 6, the survival of the animals with disseminated human Daudi lymphoma was prolonged to at least one year, at which time they remained tumor-free. As mentioned previously, in its F(ab')$_2$ form, the HD37 antibody induces CCA but not apoptosis (Ghetie et al., 1994a).

Because of this peculiar behavior, the inventors studied the physicochemical properties of one of these MAbs, HD37, in more detail and observed that it spontaneously formed homoconjugates of 300 KDa which constituted 20 to 30 percent of the purified antibody preparations. When these "natural" HD37 dimers were separated from the monomers, all the negative signaling activity could be attributed to the homoconjugates, explaining why such large amounts of the initial MAb were needed.

This finding led the inventors to suspect the possibility that chemically generated homoconjugates of HD37 and other MAbs which did not, as monomers, signal growth arrest very effectively, could be made into highly potent cytotoxic or growth-inhibiting MAbs by homo-conjugation. Homo-conjugation should yield tetravalent antibody molecules which can crosslink their target molecules more efficiently. The inventors therefore prepared homoconjugates of HD37 anti-CD19 and three other lymphoma-reactive MAbs: RFB4 anti-CD22, 3H7 anti-CD20, and B-ly 4 anti-CD21; anti-HER2 breast and prostate tumor reactive MAbs; HER-50 anti-HER-2; and an isotype-matched (control) IgG$_1$ (3F12). All homoconjugates were prepared using two heterobifunctional crosslinkers to introduce a thioether bond between the two IgG molecules. The homoconjugates were purified by preparative HPLC. The typical 300 kDa homoconjugates were ~90% pure as determined by SDS-PAGE and by analytical HPLC.

The activities of the CD19, 20, 21 and 22-reactive homoconjugates were examined on antigen-expressing Daudi and Ramos cells and the anti-Her-2 homoconjugates were studied on human breast carcinoma cells, BT 474. As shown in FIG. 2A–FIG. 2G, the homoconjugates had significant anti-growth activity on their target cells whereas the monomers, showed no effect even at the highest concentrations tested. The specific homoconjugates did not affect antigen-negative T cell tumors. Furthermore, at the same concentrations, the isotype-control homoconjugates did not inhibit the growth of target cells FIG. 2A–FIG. 2G. Thus, the anti-growth activity is specific.

Figures 3, 5A:
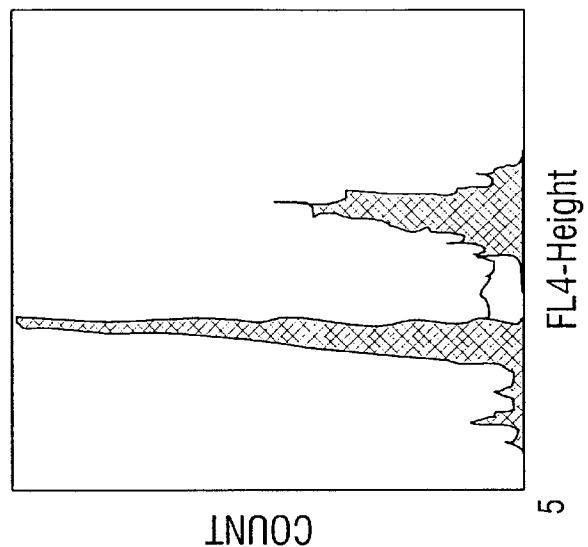
Figures 2, 5A:
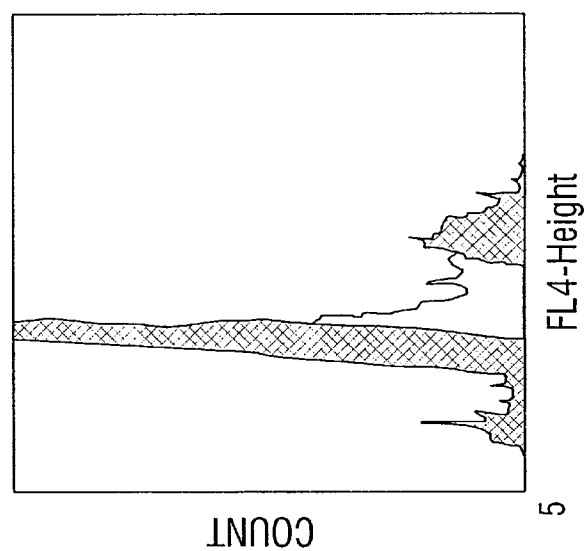
Figures 1, 5A:
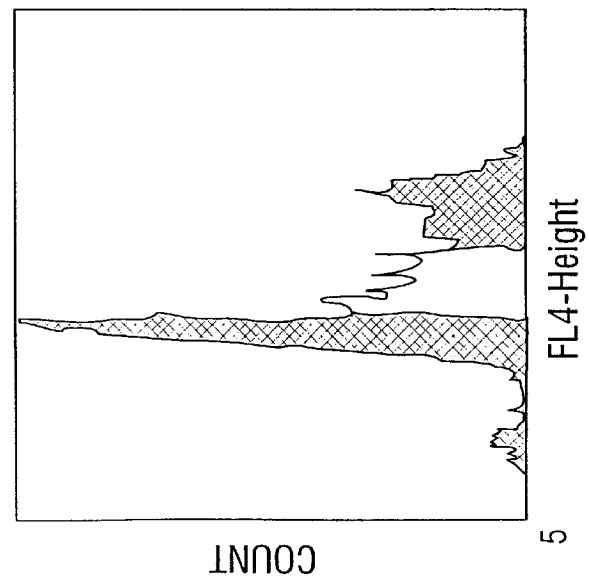

The mechanisms by which the homoconjugates exerted their anti-growth activity were further explored by carrying out cell cycle analyses, as determined by DNA content using the FACS, and apoptosis, as determined by either the Annexin V Assay (Vermes et al., 1995) or by DNA laddering (Ghetie et al., 1994). As shown in FIG. 5A and Table 3, HD37 homoconjugates but not monomers reduced the percentage of cells in S phase and arrested Daudi cells in $G_0/G_1$. As reported previously for HD37 (Ghetie et al., 1994), there was no evidence that dimeric HD37 induced apoptosis. In contrast, the homoconjugates of the anti-Her-2 MAb induced significantly more apoptosis than the monomers (FIG. 5B, Table 4). These results are in accord with a previous report which demonstrated that a dimeric vs. monomeric monoclonal IgA against the anti-Thy-1 antigen could more effectively induce apoptosis in cultured rat glomerular mesangial cells (Sato et al., 1997) supporting the concept that the degree of crosslinking and/or avidity of a MAb influences the extent of apoptosis. Thus, homoconjugates, can induce or increase anti-growth activity in target cells in two ways depending upon which surface molecule they bind.

TABLE 3

| Treatment | % of Cells | | | |
| --- | --- | --- | --- | --- |
| | G0/G1 | S | G2/M | Apoptotic |
| Control | 53.6 | 26.6 | 15.4 | 4.4 |
| HD37 monomer | 59.3 | 21.2 | 12.9 | 6/6 |
| HD37 dimer | 63.0 | 7.1 | 25.6 | 4/2 |

TABLE 4

| Treatment | % Apoptotic | Mean Fluorescence Activity |
| --- | --- | --- |
| Control | 7.64 | 43.74 |
| HER50 Monomer | 9.08 | 77.25 |
| HER50 Dimer | 20.60 | 171.40 |

Figure 7:
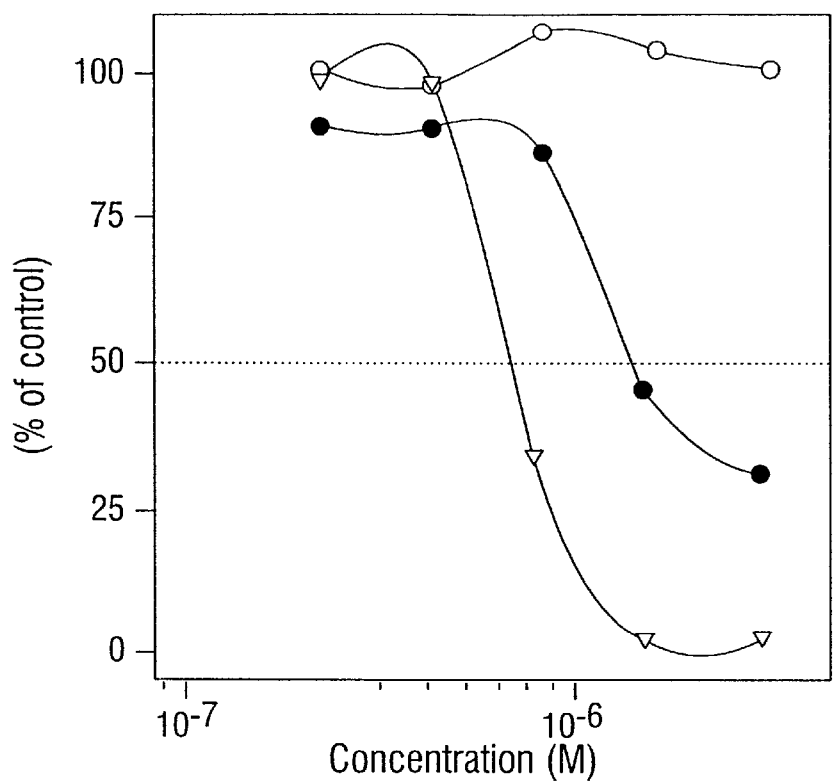
FIG. 7—The cytotoxic effect of HD37 as monomers (○), IgG dimers (●), or F(ab')$_2$ dimers (▽) using a [$^3$H]-thymidine incorporation assay (Ghetie et al., 1994.

It has been reported that homoconjugates of some MAbs have a much slower dissociation rate from cells than monomers (Wolff et al., 1993). The inventors, therefore determined whether the HD37 homoconjugates had a higher association rate ($K_a$), dissociation rate ($K_d$) or both, since these differences might be expected to affect not only their signaling properties but also their in vivo behavior. The results indicated that the $K_a$ of the monomers and dimers were the same but, as shown in FIG. 6A, that the dissociation rate of the dimers was markedly slower, making their avidity much higher. In addition, the amount of dimer bound to the membrane and internalized into the target cells was higher for the dimer than the monomer (FIG. 6B). These results are entirely consistent with those of Wolff et al (1993) who previously reported similar changes in a breast tumor reactive MAb, ChiBR96 after dimerization. In the same report they also demonstrated that dimerization increased the effector function of ChiBR96 in vitro and in vivo (Wolff et al., 1993). In the case of HD37, the inventors excluded the possibility that the marked increase in anti-tumor activity observed following homo-conjugation was due to either an increase in effector function or more avid binding to FcRs on target cells by demonstrating that F(ab')$_2$ fragments of the homoconjugates were as active as the IgG homoconjugates in the cytotoxicity assay (FIG. 7). In addition, the HD37 IgG homoconjugates showed similar anti-growth activity on Ramos cells, which lack FcγRIIs (Vervoordeldonk et al., 1994). These findings do not exclude an additional role for effector functions in vivo, although it was previously found that F(ab')$_2$ fragments of HD37 were highly therapeutic in SCID mice with Daudi tumors (Ghetie et al., 1994).

Based on the improved in vitro activity observed using the dimers, the inventors next determined how the behavior of the homoconjugates and monomers compared in vivo. For this purpose, their half lives were first determined in BALB/c mice. While the $T_{1/2}α$s were the same, the $T_{1/2}β$s were different, i.e., 71.9 hrs. for dimers and 81.4 hrs. for monomers. These results are comparable to those reported using other mouse IgG$_1$s (Kim et al., 1994). The anti-tumor activity of the HD37 monomers and dimers was then determined in SCID mice with the disseminated human Burkitt's lymphoma, Daudi. As shown in FIG. 8 at the single therapeutic dose tested (1 mg/mouse) the dimers had significantly more therapeutic activity than the monomers. Furthermore, the anti-tumor activity of the dimers was further enhanced when the animals were injected with the chemotherapeutic drug, doxorubicin. Importantly, the homoconjugates completely prevented tumor growth in the organs where the majority of the Daudi cells grow [i.e. kidney, lung and ovaries (Ghetie et al., 1990)] but had little effect on spinal lymphoma, which is the site of lethal tumor growth. This suggests that the end point in the inventors' animal model (paralysis due to spinal tumor) may actually give an underestimate of the anti-tumor activity of the dimers.

In summary, the inventors' data suggest that at least some ineffective MAbs can be converted into effective anti-tumor agents by dimerization and that this increased potency can be attributed, in some cases, to increased negative signaling presumably due to hypercrosslinking and/or a slower dissociation rate. In this regard, it has been previously proposed (Vitetta and Uhr, 1994) that MAbs be selected first for their negative signaling capacity and, subsequently, for their effector function. The present results support the use of this strategy and surprisingly show that effector function is not necessary, and in certain cases not desired, for expressing similar amounts of anti-tumor activity. These results led the inventors to realize that many other tumor-reactive MAbs which have little or no anti-growth activity should be reevaluated as homoconjugates. Furthermore, since in the case of HD37 (and perhaps other MAbs), the Fc portion is not necessary for cytotoxicity, some homoconjugates could be made even smaller by enzymatically removing the Fc portion or, alternatively, by generating recombinant Fv multimers. In this regard, recombinant oligomers (Shuford et al., 1991), tail-to-tail covalent dimers Caron et al., 1992; Greenwood et al., 1994; Shopes, 1992), and IgM-like polymers (Smith and Morrison, 1994) have all been generated and these offer the promise of increased therapeutic potential. Finally, the results in lymphoma/SCID mice suggest that multivalent MAbs might be particularly effective when given in combination with cytotoxic agents.

Preparation of Monoclonal Antibody Conjugates

Conjugates comprising mulitimers of Fab or Fv fragments may be prepared by using a variety of approaches. For example, Fabs, single chain Fv regions (scFvs), or fragments thereof, can be tagged (i.e. covalently bonded) with C-terminal peptides. These peptide tags associate to form dimers (Pack and Plückthun, 1992) or tetramers (Pack et al., 1995), depending upon the particular sequence that is used. To tag scFvs, for example, to produce dimers, one may covalently bond a C-terminal cysteine residue which can then be readily used to form a disulphide (—S—S—) bond or "bridge" by using the methodology described by Cumber et al. (1992; incorporated herein by reference).

Alternatively, an Fab, scFv, or fragment thereof, can be tagged with a C-terminal peptide that encodes a recognition sequence for an enzyme such as, but not limited to, BirA which will add a biotin moiety (Altman et al., 1996). In this case, the biotinylated scFvs can then be incubated with streptavidin to form dimers, trimers, or even tetramers. One may even desire to prepare dimers, trimers, tetramers, etc. of streptavidin and then use these conjugates of streptavidin to produce octamers, dodecamers and the like of Fabs or scFvs.

In certain embodiments, the Fab or Fv regions or fragments that are used to prepare the conjugates are prepared by enzymatic digestion of isolated Igs as in Example 1. In alternative embodiments, constructs of Fab or Fv fragments can be prepared using methods known to the skilled artisan. A preferred method of preparing Fv constructs is as follows:

Total cellular RNA is extracted from hybridoma cells and VH and VL genes are isolated as described by Ward (1995) and Popov et al. (1996). VH and VL genes are assembled as scFv genes using splicing by overlap extension (SOEing) and cloned for expression as described by Popov et al. (1996). Several methods have been used to prepare bivalent scFvs. A preferred method is described by Pack and Plückthun (1992). The scFv gene is tagged using the PCR™ and SOEing with codons encoding the following sequence: flexible hinge-amphipathic helix-cys tail as previously described by Pack and Plückthun (1992), or alternatively, as described by Holliger and Winter (1993). Trivalent scFvs can be generated by directly linking the VH and VL regions to each other without using a linker peptide. Tetravalent scFvs can be generated by tagging the scFvs with a flexible linker followed by a tetratzip sequence (Pack et al., 1995) and by SOEing.

Multimers of mulitples of four can be generated by expressing the scFvs as monomers with a C-terminal 15 amino acid biotinylation signal sequence, purifying the tagged scFvs and biotinylating them with BirA (Altman et al., 1996). Streptavidin is crosslinked using pimelidate such that dimers, trimers, tetramers, etc. form. These multimers of streptavidin are separated and incubated with biotinylated scFvs to generate octomers, dodecamers, etc.

A preferred tag is a carboxyterminal polyhistidine peptide which may by purified from periplasmic extracts of recombinant *E. coli* cells using $Ni^{2+}$-NTA-agarose followed by Superdex 75 or 200 columns. Additionally, it should be readily understood that the length of the linker peptide or peptide chain used to covalently bond heavy and light chain variable domains (VH and VL, respectively) or fragments may vary considerably. The desired length of the linker peptide will depend upon the desired use, biodistribution and half life of the final conjugates. For example, to increase the possible biodistribution of a conjugate, a shorter linker will be preferred so that the conjugate is physically smaller. For steric reasons, short linkers often favor the formation of diabodies (i.e. dimers) (Holliger et al., 1993) or tetramers. Alternatively, one may choose to prepare conjugates that comprise linkers which are about equivalent in length to an Fc region. Such linkers will not stimulate effector function in the presence of an Fc receptor. In one preferred embodiment, the linker is a genetically engineered peptide of variable length.

In addition one may choose to include one or more CH2 domains in the construct if a longer in vivo half life is desired.

Preparation of Antibodies

Means for preparing and characterizing antibodies are well known in the art (See, e.g., Antibodies: A Laboratory Manual, Cold Spring Harbor Laboratory, 1988; incorporated herein by reference).

Methods for generating polyclonal antibodies are well known in the art. Briefly, a polyclonal antibody is prepared by immunizing an animal with an antigenic composition and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or in some cases the animal can be used to generate MAbs. For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas). Particularly useful hybridomas are listed in Table 6 (Example 3) by antibody and isotype.

Any one of a number of myeloma cells may be used, as are known to those of skill in the art (Goding, pp. 65–66, 1986). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729–6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG. The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this low frequency does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and thus they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or by expression of full-length gene or of gene fragments in *E. coli*.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, $^{152}Eu$, and $^{99m}Tc$, are other useful labels that can be conjugated to antibodies. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-99 by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

It will be appreciated by those of skill in the art that the homo- and heteroconjugate antibodies of the present invention will have utilities in several types of applications. These applications will include the production of diagnostic kits for use in detecting or diagnosing neoplastic diseases. The skilled practitioner will realize that such uses are within the scope of the present invention.

Immunodetection Assays

The immunodetection methods of the present invention have evident utility in the detecting and diagnosing neoplastic conditions. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

Those of skill in the art are very familiar with differentiating between significant expression of a protein, which represents a positive identification, and low level or background expression of such a protein. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

Immunodetection Methods

In still further embodiments, the present invention concerns immunodetection methods for binding, purifying, removing, quantifying or otherwise generally detecting biological components. The homo- and heteroconjugate MAbs of the present invention may be employed to detect antigens having reactivity therewith, or, alternatively, antibodies prepared in accordance with the present invention, may be employed to detect tumor proteins or peptides. The steps of various useful immunodetection methods have been described in the scientific literature and are well known to those of skill in the art.

In the clinical diagnosis or monitoring of patients with diseases such as cancer, the detection of a neoplastic cell or tumor in comparison to the levels in a corresponding biological sample from a normal subject will be indicative of a patient with the disease or cancer. However, as is known to those of skill in the art, such a clinical diagnosis would not necessarily be made on the basis of this method in isolation. Those of skill in the art are very familiar with differentiating between significant differences in types or amounts of biomarkers, which represent a positive identification, and low level or background changes of biomarkers. Indeed, background expression levels are often used to form a "cut-off" above which increased detection will be scored as significant or positive.

In general, the immunobinding methods include obtaining a sample suspected of containing a protein, peptide or antibody, and contacting the sample with a homo- and/orheteroconjugate MAb in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a tumor cell, tumor protein or tumor-related peptide or a corresponding antibody, and contact the sample with a homo- and/or heteroconjugate MAb, as the case may be, and then detect or quantify the amount of immune complexes formed under the specific conditions.

In terms of antigen detection, the biological sample analyzed may be any sample that is suspected of containing a tumor antigen such as, a homogenized tissue extract, an isolated cell, a cell membrane preparation, separated or purified forms of any of the above protein-containing compositions, or even any biological fluid that comes into contact with neoplastic tissue, including blood.

Contacting the chosen biological sample with the homo-andor heteroconjugate MAb under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The homo- and/or heteroconjugate MAb employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

Immunohistochemistry

The antibodies of the present invention may also be used in conjunction with both fresh-frozen and formalin-fixed, paraffin-embedded tissue blocks prepared for study by immunohistochemistry (IHC). For example, each tissue block consists of 50 mg of residual "pulverized" neoplastic tissue. The method of preparing tissue blocks from these particulate specimens has been successfully used in previous IHC studies of various prognostic factors, and is well known to those of skill in the art.

Briefly, frozen-sections may be prepared by rehydrating 50 ng of frozen "pulverized" neoplastic tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

ELISA

As noted, it is contemplated that the encoded proteins or peptides of the invention will find utility as immunogens, e.g., in connection with vaccine development, in immunohistochemistry and in ELISA assays. One evident utility of the homo- and/or heteroconjugate MAbs is in immunoassays for the detection of tumor proteins and tumor-related peptides, as needed in diagnosis and prognostic monitoring of various diseased states.

Immunoassays, in their most simple and direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the tumor antigen are immobilized onto the well surface and then contacted with the antibodies of the invention. After binding and washing to remove non-specifically bound immune complexes, the bound antigen is detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the tumor protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween™. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween™, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this label will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween™).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

Use of Antibodies for Radioimaging

The homo- and heteroconjugate MAbs of this invention will be used to quantify and localize the expression of tumor proteins. The homo- and heteroconjugate MAb, for example, will be labeled by any one of a variety of methods and used to visualize the localized concentration of the cells producing the encoded protein. Such an assay also will reveal the subcellular localization of the protein, which can have diagnostic and therapeutic applications.

In accordance with this invention, the monoclonal antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration of the labeled antibody may be local or systemic and accomplished intravenously, intraarterially, via the spinal fluid or the like.

Administration may also be intradermal or intracavitary, depending upon the body site under examination. After a sufficient time has lapsed for the monoclonal antibody or fragment thereof to bind with the diseased tissue, for example 30 minutes to 48 hours, the area of the subject under investigation is examined by routine imaging techniques such as MRI, SPECT, planar scintillation imaging or newly emerging imaging techniques. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue can be determined.

It will be apparent to those of skill in the art that a similar approach may be used to radio-image the production of the tumor-related proteins in human patients. The present invention provides methods for the in vivo detection of tumor-related peptide with a view to correlating such detection to diagnosis of cancer in a patient. Such methods generally comprise administering to a patient an effective amount of a homo- or heteroconjugate MAb, to which antibody is conjugated a marker, such as a radioactive isotope or a spin-labeled molecule, that is detectable by non-invasive methods. The antibody-marker conjugate is allowed sufficient time to come into contact with reactive antigens that are present within the tissues of the patient, and the patient is then exposed to a detection device to identify the detectable marker.

Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means a homo- or heteroconjugate MAb and an immunodetection reagent.

In certain embodiments, the homo- and heteroconjugate MAbs, may be bound to a solid support, such as a column matrix or well of a microtiter plate.

The immunodetection reagents of the kit may take any one of a variety of forms, including those detectable labels that are associated with or linked to the given homo- and heteroconjugate MAb, and detectable labels that are associated with or attached to a secondary binding ligand. Exemplary secondary ligands are those secondary antibodies that have binding affinity for the homo- and heteroconjugate MAb, and secondary antibodies that have binding affinity for a human antibody.

Further suitable immunodetection reagents for use in the present kits include the two-component reagent that comprises a secondary antibody that has binding affinity for the homo- and heteroconjugate MAb, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

Pharmaceutical Compositions and Routes of Administration

Aqueous compositions of the present invention comprise an effective amount of the homo- or hetero-conjugate MAb, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains an RNA elongation transcription inhibitor agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters. In all cases the form must be sterile and must be fluid to the extent that easy syringability exists. It must be stable under the conditions of manufacture and storage and must be preserved against the contaminating action of microorganisms, such as bacteria and fingi.

Solutions of the inhibitory compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active inhibitory compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In terms of using peptide inhibitors as active ingredients, the technology of U.S. Pat. Nos. 4,608,251; 4,601,903; 4,599,231; 4,599,230; 4,596,792; and 4,578,770, each incorporated herein by reference, may be used.

The preparation of more, or highly, concentrated solutions for direct injection is also contemplated, where the use of DMSO as solvent is envisioned to result in extremely rapid penetration, delivering high concentrations of the active agents to a small body area.

The therapeutic compositions of the present invention may include classic pharmaceutical preparations. Administration of therapeutic compositions according to the present invention will be via any common route so long as the target tissue is available via that route. This includes oral, nasal, bucal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active inhibitors or agents may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance. For the instant application, it is envisioned that the amount of therapeutic composition comprising a unit dose will range from about 5–30 mg of polynucleotide.

A therapeutically effective amount of a conjugate varies depending upon the host treated and the particular mode of administration. In one embodiment of the invention the dose range of a conjugate is about 0.5 mg/kg body weight to about 500 mg/kg body weight. The term "body weight" is applicable when an animal is being treated. When isolated cells are being treated, "body weight" as used herein should read to mean "total cell weight". The term "total weight" may be used to apply to both isolated cell and animal treatment. All concentrations and treatment levels are expressed as "body weight" or simply "kg" in this application are also considered to cover the analogous "total cell weight" and "total weight" concentrations. However, those of skill will recognize the utility of a variety of dosage range, for example, 1mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5mg/kg body weight to 250 mg/kg body weight, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight.

Further, those of skill will recognize that a variety of different dosage levels will be of use, for example, 1mg/kg, 2 mg/kg, 3 mg/kg, 4 mg/kg, 5 mg/kg, 7.5 mg/kg, 10, mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 1 00 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1 500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for conjugates.

"Therapeutically effective amounts" are those amounts effective to produce beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level conjugates for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will, determine the appropriate dose for the individual subject. Moreover, for human administration, preparations should meet sterility, pyrogenicity, general safety and purity standards as required by FDA Office of Biologics standards.

In many instances, it will be desirable to have multiple administrations of the pharmaceutical preparation of a conjugate, usually not exceeding six administrations, more usually not exceeding four administrations and preferably one or more, usually at least about three administrations. The administrations will normally be at from one to twnty four hours, one to two to three to four or even as long as twelve week intervals, more usually from three to five week intervals. Periodic boosters at intervals of 1–5 years, usually three years, may be desirable in certain instances to maintain protective levels of the antibodies. The course of treatment may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Homodimerization of MAbs Increases Signaling of Growth Arrest or Apoptosis of Tumor Cells Cells. Two human Burkitt's lymphoma cell lines, Daudi and Ramos, were maintained in culture by serial passage in RPMI 1640 medium containing 25 nmol/L HEPES, 10% heat-inactivated fetal bovine serum, 100 U/ml penicillin, 100 mg/ml streptomycin (complete medium), and 100 nmol/L L-glutamine. The cells were grown in a humidified atmosphere of 5% $CO_2$ and air. Cell viability was determined by trypan blue exclusion. Cells from the breast cancer line, BT474 were maintained by serial passage in MEM containing 10% heat-inactivated fetal calf serum, 2 mM L-glutamine, 100 nM non-essential amino acids, I mM sodium pyruvate and 2% vitamins for MEM.

Preparation of the anti-HER-2 MAb. BALB/c mice were immunized with a recombinant form of the 641 amino acid extracellular domain of HER-2. Spleen cells from the immunized mice were harvested and fused with the myeloma cell line, SP2/0. The hybridomas were subcloned and assayed for the ability to produce immunoglobulin by ELISA. Antibody-containing supernatants from positive clones were tested by ELISA for reactivity against the Her-2 extracellular domain and by FACS on a Her-$2^+$ cell line, SKBr3. The antibody chosen for this study was designated HER-50.

MAbs. Mouse $IgG_1$ MAbs specific for CD22 (RFB4), CD19 (HD37), CD20 (3H7), CD21 (B-ly4), Her-2 (HER-50) and the purified isotype matched $IgG_1$ of irrelevant specificity (3F12) were used. RFB4 and HD37 were prepared in the inventors' scale-up laboratory (Ghetie et al., 1991). 3H7 and B-ly4 were purchased from PharMingen. IgGs from 3F12 and HER-70 were prepared in the inventors' laboratory by purification of hybridoma cell supernatant (SNs) on a protein A-Sepharose column.

Preparation of homoconjugates by introducing a thioether bond. Two heterobifunctional cross-linkers were used to dimerize the MAbs without using reducing reagents. SMCC [succinimidyl 4-(maleimidomethyl)cyclohexane-1-carboxylate] and SATA (N-succinimidyl S-acethylthio-acetate) were purchased from Pierce (Rockford, Ill.).

(1) Derivatization with SMCC. 250 mg of MAb at 10 mg/ml in 0.05M phosphate buffer containing 3 mM $Na_2$-EDTA (PBE) pH 7.5 was mixed with 250 ml of SMCC (concentration of 10 mg/ml in DMF) for 1 hr at room temperature. The SMCC/IgG molar ratio was 4.5. After 1 hr, the protein was purified by chromatography on a Sephadex G-25 column (in the same buffer). The purified protein was concentrated to 10 mg/ml by Centriprep concentrators (Amicon, Beverly, Mass.).

(2) Derivatization with SATA. 250 mg MAb at 10 mg/ml was mixed with 250 ml SATA (6.3 mg/ml in DMF) and incubated for 1 hr at room temperature. The SATA/IgG molar ratio was 4.0. The excess SATA was removed by chromatography on a Sephadex G-25 column. The purified protein was concentrated to 10 mg/ml and was deacetylated with 0.15M hygroxylamine-HCl for 5 min. at room temperature. Both derivatized proteins were mixed together and incubated at room temperature for 1–2 hrs. Mixtures were analyzed by SDS-PAGE and 20–25% of the IgG was in dimeric form [300 KDa]). The preparation was dialyzed O/N vs. 0.05M PBE at 4° C., filter sterilized and further purified on a 600×21.5 mm Bio-Sil® Sec.400 HPLC column at flow rate of 2 ml/min. Generally, the dimer had a retention time of about 66 min., while the monomer had a retention time of about 74 min. The protein fractions purified by HPLC were concentrated to 5–10 mg/ml, filter sterilized on a 0.22 mm filter unit (sterile MILLEX®-GV)(Millipore Products Division, Bedford, Mass.) and analyzed by SDS-PAGE and HPLC.

Preparation of F(ab')$_2$ homoconjugates. HPLC-purified HD37 dimers were dialyzed O/N against 0.1M acetate buffer pH 3.5–4.0 and digested with insoluble pepsin (Sigma, St. Louis, Mo.) for 3 hrs. at 37° C. The dimer pepsin-digest was affinity purified on a SpA-Sepharose column. The material not bound to the column was further affinity purified on a protein G-Sepharose column. 60% of this material was bound and eluted with 0.1M acetic acid, then neutralized to pH 7.5, concentrated and analyzed by analytical HPLC and SDS-PAGE gel to determine the molecular weight (200 KDa).

SDS-PAGE. Proteins were analyzed under both reducing and nonreducing conditions by SDS-PAGE on 4–15% gels using a Phast System Separation Unit (Pharmacia). Protein bands were visualized by staining the gel with Coomassie blue in the same Phast System.

High performance liquid chromatography (HPLC) analysis. The molecular weights of the dimers were determined by analytical HPLC using a 600×7.5 mm Bio-Sil SEC-400 (BioRad, Richmond, Calif.) column equilibrated in 0.05 M sodium phosphate buffer, pH 6.8. A standard protein mixture containing IgA (300 KDa) and IgG (150 KDa) was fractionated on the HPLC column to establish the retention time of known molecular weight standards.

3H-Thymidine Assay. The anti-proliferative activity of different MAb monomers and dimers on Daudi cells was determined using a [$^3$H]-thymidine incorporation assay as described by Ghetie et al., (1988) and incorporated herein by reference.

Measurement of the dissociation rate. IgG and F(ab')$_2$ fragments were radioiodinated with Na$^{125}$I to a specific activity of approximately 1 mCi/mg using the IODOGEN reagent (Pierce, Rockville, Ill.) (Fraker and Speck, Jr, 1978) and dissociation rates were determined as described by Coligan et al. (1991) and incorporated herein by reference.

Internalization studies. Daudi cells (1×10$^6$/ml) were treated on ice for one hour with $^{125}$I-labeled MAb (monomer or dimer) at 1 µg/ml (specific activity 0.25 µCi/µg). This concentration of antibody was sufficient to saturate all available binding sites on Daudi cells (about 10$^5$ IgG molecules bound per cell). Then the cells were washed free of excess ligand with complete RPMI media at 4° C., resuspended at the initial concentration and returned to 37° C. for different periods of time (2, 4, 8 and 24 hrs.), and then assayed for the radioactivity in the supernatant, surface membranes, and intracellular compartments as described (Press et al., 1989; incorporated herein by reference).

Cell cycle analysis (CCA. Cells were simultaneously examined for viability and cell cycle status by flow cytometric analysis using the DNA-binding dyes 7-amino actinomycin D (7-ADD) and Hoechst 33342 (both from Molecular Probes, Eugene, Oreg.) (Darzynkiewicz et al., 1992; incorporated herein by reference).

Apoptosis assays. 2 to 5×10$^6$ treated or untreated Daudi cells were collected by centrifugation and lysed in 0.2 to 0.5 ml hypotonic buffer (5 mmol/L Tris-HCl, pH 7.4, 5 mmol/L Na$_2$-EDTA, 0.5% Triton X-100). The lysates were centrifuged and the SNs were deproteinated as described elsewhere (Ghetie et al., 1994; incorporated herein by reference). The DNA extracts were analyzed on a 2% agarose gel, containing 0.0001% ethidium bromide (for apoptosis). 1×10$^5$ BT474 cells in 1 ml MEM containing 10% heat-inactivated fetal calf serum, 2 mM L-glutamine, 100 nM non-essential amino acids, 1 mM sodium pyruvate and 2% vitamins for MEM were plated into duplicate wells of 24-well microtiter plates and allowed to adhere overnight. Cells were treated with 50 μg/ml antibody or 20 ng/ml TNF-α (positive control) for 1, 2, or 4 hours and harvested following trypsinization in 0.5% trypsin-EDTA solution. BT474 cells were treated with Annexin V-FITC and propidium iodide for 15 minutes and analyzed for the presence of phosphatidyl serine on their surface by FACScan (Becton-Dickinson). Cells permeable to propidium iodide were excluded from the analysis. Annexin V positive cells were taken as apoptotic cells.

Pharmacokinetic studies. Pharmacokinetic analyses were carried out in BALB/c mice using a method described elsewhere (Kim et al., 1994). Data analysis was carried out using a non-compartnental model (Kaetzel et al., 1991; Song et al., 1994) and a PKCAL program (Schumaker, 1986). The half lives were calculated using 0–24 hr (a-phase) and 24–96 hr (β-phase) intervals of time following injection.

SCID/Daudi mice. Female C.B-17 Scid/Scid mice used. Six-to 10 week-old female mice were inoculated iv. with 5×10$^6$ Daudi cells in 0.1 ml RPMI medium. Mice were monitored daily and sacrificed at the onset of hind leg paralysis, a clinical symptom which precedes death (Ghetie et al., 1990).

EXAMPLE 2

Homo- and Heterodimers of MAbs

In order to determine what "combinations of epitopes" generate the most potent negative signal when bound to or crosslinked by antibodies a series of studies were done. First, different pairs of monomeric (IgG) signaling antibodies directed against CD 19, –20, –21, –23, and –24 are used to determine if there are additive anti-growth effects. These MAbs are available commercially. [$^3$H]-thymidine incorporation, CCA and apoptosis are measured to determine a) what pathways are involved and b) whether enhancement occurs in one or both pathways. Initial survey is limited to mixtures of two MAbs; however, it is envisioned that three or even four MAbs may be used. Initially target cells are cultured with an IC$_{50}$ concentration of one MAb and a range of concentrations (10$^{-10}$–10$^{-1}$ M) of the other. CCA and apoptosis are analyzed at different time points (from 6–36 hours). These assays (Darzynkiewicz et al., 1992) are routine in the laboratory. Based on the results of these combinations, homodimers (IgG)$_2$ of all the MAbs are prepared and used alone or in similar combinations. These are tested on 10 different B-lymphoma cell lines (including Burkitt's, AIDS, pre-B, LPD and diffuse histiocytic). Next, heterodimers of the most active MAbs are prepared. Again, these are tested on the cell panel. These analyses provide an excellent idea of which MAbs or combination of MAbs used as homo- or heterodimers should make the best therapeutic reagents. The potential sensitization of cells by potent MAbs to chemotherapy (Ghetie et al., 1 996a) is also examined.

EXAMPLE 3

New Apoptosis-inducing MAbs

Thus far, anti-IgM is the only antibody which induces apoptosis in B lymphoma cells (Racila et al., 1995). Since anti-IgM cannot be used clinically, anti-CD79 antibodies are prepared. The available anti-CD79 MAbs are of low affinity and do not signal. Since CD79 molecules are responsible for mig-mediated signals and are associated with mIg on the cell surface (Wienands et al., 1996; Gold and DeFranco, 1994; Blum et al., 1993), should also signal apoptosis following hypercrosslinking. This signaling is verified by immunizing rabbits with immune complexes prepared with a MAb anti-CD79b and a detergent lysate of 10$^9$ Daudi cells. The complexes were isolated on a sucrose gradient and the rabbits were injected five times in Freund's adjuvant. At one month intervals after each boost, serum was obtained and tested by immunoprecipitating lysates of $^{125}$I-labeled Daudi cells. When bands corresponding to the molecular weights of CD79 were observed on autoradiographs, the sere were pooled, the IgG was purified on a protein G-Sepharose column, and the IgG antibody was absorbed with a series of cell lines of human origin (lacking CD79), with mouse IgG and human IgG and then affinity-purified on 3% paraformaldehyde fixed Daudi cells. To determine whether this relatively pure antibody can negatively signal Daudi cells and other Ig$^+$ human lymphomas, is initially done using [$^3$H]-thymidine incorporation (Ghetie et al., 1994a) and $^{32}$P-Syk and Lyn kinase assays (Law et al., 1992; Richards et al., 1996; Gold et al., 1992) where cells are cultured with different concentrations of the antibody for 1 min. –6 hrs. and then pulsed for 6 hr with tritiated thymidine or lysed and incubated with $^{32}$P. If there is a reduction in [$^3$H]-thymidine incorporation, or a change in Syk or Lyn phosphorylation (Ren et al., 1994; Faris et al., 1994), CCA and apoptosis assays are done as outlined below. If the purified antibody induces apoptosis, a large batch of PAb are prepared for use in SCID/Daudi mice. PAb anti-CD79 does induce phosphorylation of Syk, but the signal is weak (FIG. 7). 2) The antibody is also used to immunoprecipitate large amounts of antigen from Daudi cell lysates. The eluted antigen is used to raise MAbs in mice via_standard procedures. These MAbs have been screened on Daudi cells, Jurkat cells and HIg by ELISA. The 10 hybridoma MAbs which are Daudi$^+$, Ig$^-$, Jurka$^-$ are subcloned and rescreened by western blotting on Daudi cell lysates. Affinities of CD79 MAbs are determined by standard Scatchard assays and those antibodies with the highest affinities will be grown up, purified, pooled, and tested in signaling assays in the same way that the rabbit sera were evaluated.

Methods.

a. Cell lines

TABLE 5

The following exemplary human B lymphomas are used:

| Type | Cell Line | Reference |
| --- | --- | --- |
| Burkitt's | Daudi | (Klein et al., 1989) |
|  | Raji | (Pulvertaft, 1964) |
|  | Namalwa | (Hurwitz et al., 1979; Campana et al., 1985) |
|  | Ramos | (Dorken et al., 1983; Clark and Ledbetter, 1986) |
|  | Jiyoye | (Ghetie et al., 1991) |
| Pre-B | NALM-6 | (Lukic and Mitchison, 1984) |
|  | HPB-Null |  |

TABLE 5-continued

The following exemplary human B lymphomas are used:

| Type | Cell Line | Reference |
|---|---|---|
| | NALL-1 | (Lukic and Mitchison, 1984) |
| | SMS-SB | |
| Primary LPD (from PBL ® SCID) | LPD-10.16 | |
| | LPD-13.11 | |
| Diffuse histiocytic | DHL-4 | |
| AIDS lymphoma (HIV-) | ST486 | |
| | JD-38 | |
| | KK124 | |
| Immunoblastoma, lymphoma | CESS | |
| NHL | RMPI 1788 | |

Cells are maintained by serial passage in RPMI-1640 medium containing 10% heat-inactivated fetal bovine serum, 100 units/ml penicillin, 100 mg/ml streptomycin, and 100 mM L-glutamine (complete medium). The cells are grown in a humidified atmosphere of 5% $CO_2$ and air. Cells are washed and the cell suspension is adjusted to an appropriate concentration for inoculation. Viability of the cells is determined by Trypan blue exclusion.

b. Antibodies

The hybridomas secreting anti-CD 19 (Chen et al., 1995), anti-CD20 (Knapp et al., 1989) and anti-CD22 (Goding, 1983) (Table 6) were maintained as both frozen stock and seed cultures. Five gram quantities of mycoplasma-free crude antibody have been grown in hollow fiber, purified tested, aliquoted and stored. Briefly, MAbs were purified from supernatants on Sepharose-Protein G using routine buffer systems under sterile, endotoxin-free conditions in a GLP scale-up laboratory (Li et al., 1989). Purified Ig is concentrated to 5 mg/ml on Amicon concentrators and assayed by SDS-PAGE, HPLC, IF/FACS and Scatchard binding. Purified preparations are sterilized and maintained at −70° C. until used.

The anti-CD21 (B-ly4), anti-CD23 (ML233) and anti-CD24 (MLS) purified antibodies were purchased from PharMingen (San Diego, Calif.). To prepare MAbs inhouse, BALB/c mice were injected five times with immune complexes formed between the mouse Ig (MAb) and $10^9$ lysed Daudi cells plus GAMIg. The final tests included immunoprecipitation, determination of binding affinity and secretion rate. Positive clones were subcloned and retested. The best five lines were chosen and frozen stocks are prepared. Five gram lots of purified MAbs were then prepared. Eight candidate anti-CD20 hybridomas, 7 anti-CD21 hybridomas and 10 anti-CD79 hybridomas were further evaluated by western blotting, Scatchard, and SDS-PAGE.

TABLE 6

Exemplary Hybridomas

| NAME OF ANTIBODY | CLONE | ISOTYPE | REFERENCE |
|---|---|---|---|
| Anti-CD19 | HD37 | $IgG_1K$ | (Chen et al., 1995) |
| Anti-CD20 | 3H7 | $IgG_1K$ | (Krolick et al., 1980) |
| Anti-CD22 | RFB4 | $IgG_1K$ | (Kohler et al., 1990) |
| RPC-5 (Control) | RPC5 | $IgG_{2A}$ | (Gorczyca et al., 1993) |
| MOPC-21 (Control) | MOPC-21 | $IgG_1$ | (Gorczyca et al., 1993) |
| 3F12 (Control) | 3F12 | $IgG_1$ | |

(i) Production of MAbs

BALB/c mice were immunized twice at monthly intervals (×5 months) with immune complexes from $10^8$ Daudi cells. Three days before fusion, the mice were boosted intravenously (i.v.). Splenocytes from immunized mice were fused with mouse myeloma cells SP2/O using 40% polyethylene glycol (PEG) and grown in hypoxanthine/aminopterin/thymidine (HAT) medium (Terstappen et al., 1990). Supernatants from growing clones were screened by a cellular ELISA for antibody against Daudi cells. MAbs must react with Daudi but not Jurkat cells or human Ig. The specific MAbs were further screened by flow cytometry, immunoprecipitation (vs. the standard MAb) and Scatchard analysis. The MAbs were purified from culture supernatants by affinity chromatography with Gamma-binding G-agarose column (Gene Corporation, Gaithersburg, Md.). Cross-blocking experiments were then done to select MAbs with different epitope reactivities.

(ii) Cellular ELISA

The 96-well ELISA plates were coated for 30 minutes with 50 ml poly-L-lysine (0.01% in PBS, Sigma, St. Louis, Mo.). After removing the poly-L-lysine, $1\times10^5$ Daudi cells per well are centrifuged onto the plates at 2,000 RPM for 10 minutes. The cells were fixed for 15 minutes with 0.5% glutaraldehyde and the plates were washed three times with PBS. Fifty microliters of 1% BSA in PBS containing 100 mM glycine were added and incubated for 45 minutes. The plates were then blocked with 150 ml per well of 2% BSA in PBS containing 0.05% sodium azide and stored at 4° C. for use. After three washes with PBS, 50 ml hybridoma supernatants were added to each well and the plates were incubated for 1 hour at room temperature. The plates were washed again and incubated with 50 ml of a diluted goat anti-mouse Ig (GAMIg)-alkaline phosphatase conjugate (Tago, Burlingame, Calif.) for an additional hour. The plates are washed and developed for 30 minutes with phosphatase substrate paranitro-phenylphosphate (Sigma, St. Louis, Mo.). Fifty microliters per well of 3 M NaOH were then added to stop the reaction. The absorbance of each well was determined at 405 nm in a ELISA reader (Nippon Intermed K.K., Tokyo, Japan).

(iii) Antibody isotyping

An ELISA isotyping kit is used to determine the isotype of antibody secreted following manufacturer's protocols (Boeringer Mannheim Biochemicals, Indianapolis, Ind.).

(iv) Immunoprecipitation

Daudi cells ($10^8$ log phase) were centrifuged and washed in PBS. In some studies, Daudi cells were radioiodinated according to standard procedures (Laemmli, 1970). Cells were lysed in 2.0 ml 0.5% $NP_4O$. Lysates were centrifuged and the supernatants were treated with saturating amounts of the MAb-GAMIg immunocomplexes (Isakson et al., 1981). The immunocomplexes were purified on sucrose gradients, washed and injected subcutaneously (s.c.) in Freund's adjuvant.

(v) Scatchard Analysis

IgG and F(ab')$_2$ fragments were radioiodinated with $Na^{125}I$ to a specific activity of approximately 1 mCi/mg using the IODOGEN reagent (Pierce, Rockville, Ill.) (Trucco and De Petris, 1981). Daudi cells were incubated for 3 hr at 4° C. with various concentrations of radiolabeled MAbs (0.02–10 mg/ml/$10^7$ cells) in RPMI 1640 medium containing 10% fetal calf serum (FCS) and 0.1% sodium azide. The cells were then separated from the medium by centrifugation through a mixture of dibutylphthalate and bisethylhexylphthalate (1.1:1.0 v/v). The supernatants were discarded, the tips of the tubes containing the cell pellets were cut off and the radioactivity was measured in a gamma counter. The amount of radiolabeled ligand specifically bound was calculated by subtracting the radioactivity bound in the presence of an excess of unlabeled ligand from the total radioactivity bound. In all cases, 95% or more of the binding of the radiolabeled ligand should be inhibited by addition of a 100-fold molar excess of unlabeled ligand, showing that the vast majority of binding of the radiolabeled ligand is specific. The affinity constant (K) and the number of ligand molecules per cell (n) under equilibrium conditions was calculated by using the Scatchard form of the equilibrium equation (Trucco and De Petris, 1981).

(vi) SDS-PAGE

Proteins were analyzed under both reducing and nonreducing conditions by SDS-PAGE on 10% gels according to Laemmli (Ward, 1995). Protein bands were visualized by staining the gel with Coomassie blue. Alternatively, routine autoradiography was carried out. The following proteins were used as standards for the estimation of molecular weight (BioRad, Richmond, Calif.): ovalbumin, 45 Kd; bovine serum albumin, 66 Kd; phosphorylase B, 92.5 Kd; b-galactosidase, 116 Kd; and IgG1, 150 Kd.

c. Preparation of MAb Homodimers and Heterodimers using SMCC and SATA as Crosslinkers SMCC=succinimidyl 4-(N-maleimidomethyl) cyclohexane-1-carboxylate and SATA=N-succinimidyl S-acethylthio-acetate (both from Pierce, Rockford, Ill.).

(i) Derivatization of MAb with SMCC

Fifty milligrams of MAb at 10 mg/ml in 0.05 M PBE pH 7.5 was treated with 65 ml of SMCC (conc.=10 mg/ml in DMF) for 1 hr at RT. The molar ratio SMCC/IgG=5.8. After 1 hr, the protein was purified from excess of SMCC by a Sephadex G-25 column (in the same buffer). The purified protein was concentrated to 10 mg/ml.

(ii) Derivatization of MAb with SATA

Fifty milligrams MAb at 10 mg/ml was mixed with 65 ml SATA (at 6 mg/ml in DMF) and incubated for 1 hr at room temperature (molar ratio SATA/IgG=5.1). The excess SATA was excluded by gel-filtration through Sephadex G-25. The purified protein was concentrated to 10 mg/ml and was then deacetylated with 0.15 M hydroxylamine-HCl (5 min. at room temperature (RT)). Both derivatized proteins were mixed together and incubated at 25° C. for 1–2 hrs. SDS-PAGE analysis was carried out (20% of IgG is usually in a dimeric form [300 KD]). The preparation was dialyzed O/N vs. 0.05 M PBE at 4° C., filter sterilized and further purified on a Bio-Sil 600' 21.5 cm HPLC column (flow rate 1 ml/min.). Generally, the dimer had a retention time £28 min., while the monomer retention time was 31 min. In the case of heterodimers, these were affinity purified by sequential passage over Seph-anti-Id$_1$ plus Seph-anti-id$_2$. All anti-Ids were raised by injecting rabbits with a single MAb in adjuvant. Sera were affinity purified and then adsorbed with a pool of the other antibodies on Sepharose. Final purity was determined by RIA against each MAb. Antibodies were stored in sterile 1 M glucose at 4° C. to prevent further aggregation. HPLC analysis was carried out monthly.

d. [$^3$H]-thymidine Assay

The activity of different Abs was determined using [$^3$H]-thymidine incorporation (Hoagland, 1992). F(ab')$_2$ fragments gave similar results to IgG antibody in the in vitro assays; F(ab') fragments had no effect on the cells.

e. Apoptosis and CCA

Two very sensitive and complementary flow cytometric techniques were used to simultaneously evaluate apoptosis and cell cycle status of the tumor cells. Apoptosis is characterized by the occurrence of endonucleolytic digestion of DNA which results initially in DNA strand breaks that are soon followed by characteristic fragmentation of all chromosomes (Ling et al., 1996). Using the first technique, cells were permeabilized and the early DNA strand breaks were labeled with biotinylated nucleotides via the action of the enzyme terminal deoxynucleotidyl transferase (Chen et al., 1993). These strand breaks were then visualized with a streptavidin-RED$^{613}$ conjugate. Cells were also stained with the DNA-binding dye Hoechst 33342 (as well as two different antibodies when conjugated to FITC and phycoerythrin, respectively), allowing the simultaneous analysis of our dual laser FACStar$^{Plus}$ flow cytometer (Racila et al., 1995; Pittman et al., 1994) of DNA strand breaks, overall DNA content, and CD19/IGM expression. Thus, in a single analysis, cell cycle status, early apoptosis (strand breaks but no DNA fragmentation), and late apoptosis (DNA fragmentation present, as indicated by loss of overall DNA content in permeabilized cells) on a gated population of tumor cells were evaluated. In the second technique, the Hoechst dye, CD19, and IgM are simultaneously evaluated in conjunction with the vital fluorescent dye 7 amino actinomycine D (Molecular Probes, Inc.). This combination allowed determination of cell cycle status, DNA fragmentation, and membrane permeability (the latter two parameters allowing delineation of later stages of apoptosis) on the same population.

f. Cytotoxicity assay $10^5$ cells/100 ml in RPMI medium 1640 containing 10% FCS, glutamine, and antibiotics were distributed into triplicate wells (96-well microtiter plates) containing 100 ml of medium and concentrations of antibodies (monomer or dimer) ranging from $10^{-8}$ to $10^{-6}$ M and incubated for 24–48 h at 37° C. Cells were pulsed for 1 h at 37° C. in 5% $CO_2$ with 5 mCi [$^3$H]-thymidine (Amersham, Arlington, Va.). Wells were harvested on a Titertek cell harvester (Flow Labs, Rockville, Md.) and the radioactivity on the filters was counted in a liquid scintillation spectrometer. The percentage of reduction in [$^3$H]-thymidine incorporation, as compared with untreated controls, was used as the assessment of killing (Kung et al., 1990). Nine wells of untreated cells were included in each group.

g. $^{32}$P-Syk/Lyn kinase assays

Human B lymphoma cells (5' $10^6$) were stimulated with anti-human IgM or anti-CD79 antibodies for various amounts of time at 37° C. The cells were then washed and lysed in 0.5 ml lysis buffer (10 mM Tris-CI, pH 7.5, 150 mM NaCl, 1% NP-40, 1 mM $Na_3VO_4$, 1 ug/ml leupeptin and 10 ug/ml aprotinin and 20 mM sodium fluoride). The cell lysates were cleared by centrifugation at 12,000 g, and lysates were incubated with protein A-Sepharose beads (Sigma, St. Louis, Mo.) precoated with anti-Syk or anti-Lyn MAbs (Santa Cruz Biotechnology Inc., Santa Cruz, Calif.) for 2 hours at 4° C. The immunoprecipitates were washed five times in 0.1% Tween-20 PBS once with kinase reaction buffer (20 mM Tris-CI, pH 7.5, 100 mM NaCl, 5 mM $MgCl_2$ and 5 mM $MnCl_2$), and then resuspended in 50 ul kinase reaction buffer with 10 uCi r-[$^{32}$P]ATP (Amersham). After incubation for 15 minutes at room temperature, the immunoprecipitates were washed five times with 0.1% Tween-20 PBS and analyzed by SDS-PAGE. Phosphorylated proteins were visualized by autoradiography.

Alternative Strategy.

Virtually all polyclonal anti-Ig antibodies induce apoptosis and since it is known that membrane Ig signals via its association with CD79 molecules (Pleiman et al., 1994; Nakamura et al., 1993; Kuwahara et al., 1993), it is highly likely that the appropriate anti-CD79 PAbs or MAbs should also induce apoptosis. Regardless of the antitumor effect of these antibodies, they would still be very valuable for targeting B cells and B lymphoma cells with toxins or isotopes. Regardless, whether or not the PAb works, it is conceivable that a combination of dimers of MAbs with the right affinities will signal apoptosis even if the PAb is negative. With regard to any new anti-CD79 MAbs, these might recognize epitopes on life-sustaining human tissues. This is not expected to be the case, but it could occur. If it does happen, hybridomas will be screened more rigorously on normal tissues to select a MAb which does not recognize a crossreactive epitope.

EXAMPLE 4

Signaling MAbs Increase the Sensitivity of Lymphoma Cells to Chemotherapeutic Agents±ITs.

Objectives and Approach

One attractive use for MAbs in cancer therapy is as "sensitizers" for chemotherapy. Hence, MAbs which signal CCA, apoptosis or inhibition of protein synthesis in cells might render them more sensitive to lower doses of chemotherapy. If so, toxic side effects of chemotherapeutic agents should be decreased and the therapeutic window preserved. This would be of major importance for patients. It is hypothesized that those drugs which negatively signal cells via pathways which are different from those signaled by MAbs or which arrest cells in a different phase of the cell cycle might act synergistically or additively with MAbs to increase the sensitivity of treated cells to chemotherapeutic agents. There are, of course, other possibilities. For example, 1) MAbs and chemotherapeutic agents may work on different tumor cell subpopulations, 2) chemotherapeutic drugs may sensitize cells to MAbs or vice versa, 3) the two agents may trigger common pathways resulting in more profound signaling and 4) MAbs might alter or reverse MDR.

Several chemotherapeutic drugs commonly used in the treatment orb lineage lymphomas were examined for their ability to induce CCA in Daudi cells in vitro. These include Doxorubicin (DOX), Vincristine (VIN), Solumedrol (SOL), Methotrexate (METH), Cytoxan (CYT) and Camptothecin (CPT). VIN is a G2/M phase specific agent, METH is a S phase specific agent and CPT is a topoisomerase-1 inhibitor (Minderman et al., 1991). Data indicate that these drugs are capable of suppressing S phase and that DOX and VIN arrest cells at G2/M 24 hours after their addition to culture. In contrast, SOL and METH cause cells to accumulate at the G1 phase of the cell cycle at 24 hrs. These results are consistent with reports in the literature using other cell lines (Tsurusawa et al., 1990; Petru et al., 1995; Sevin et al., 1986; Ghetie et al., 1990; Vial and Descotes, 1992; Shah et al., 1992; Senderowicz et al., 1997).

It has been reported that cells are more vulnerable to chemotherapeutic agents based on the phase of the cell cycle in which they are arrested and that cell cycle perturbations can correlate with responses to chemotherapy in vitro (Messinger et al., 1996) and in vivo (Ahsmann et al., 1995). There are no reports of non-conjugated MAbs potentiating chemotherapy in the treatment of lymphoma. Although there are a limited number of studies comparing cytotoxicity with cell kinetic effects using drugs with different modes of action, the combination of agents with overlapping and nonoverlapping effects has not been examined to determine their additive or synergistic potential. The endpoint is the measurement of cell death at particular time intervals. Initially, the HD37 MAb are used since it can increase the cytotoxic efficacy of at least one chemotherapeutic agent, VIN by 10-fold (FIG. 8). This effect is a highly reproducible result.

Synergy with other drug combinations is examined using the anti-CD19 MAb and with signaling antibodies (monomers or dimers) previously generated. Studies focus on the best way in which to most effectively use these agents in vivo. In brief, titrations of each chemotherapeutic drug (or combination of drugs) are carried out in the absence and presence of $IC_{20}$, $IC_{50}$ and $IC_{90}$ concentrations of one or more signaling MAbs. MAbs are added to cells prior to drugs in some experiments, at the same time in others and after in others. Based on this information, regimens for in vivo use are designed as described in Example 3.

Methods a. Chemotherapy

A panel of chemotherapeutic agents which inhibit the growth of Daudi and DHL cells in SCID mice and which are used in patients with NHL are chosen. The antibiotic DOX is purchased from Pharmacia Inc. (Columbus, Ohio) and the alkylating agent CYT is obtained from Bristol-Myers Squibb (Princeton, N.J.). The topoisomerase 1 -inhibitor CPT is prepared at the Stehlin Foundation (Houston, Tex.). VIN is obtained from Eli Lilly and Company (Indianapolis, Ind.). The glucocorticoid SOL is obtained from the Upjohn Company (Kalamazoo, Minn.). The antimetabolite METH is obtained from the Immunex Corp. (Seattle, Wash.).

Alternative Strategy

Even if the hypotheses of additivity/synergy based on cell cycle effects of each agent are incorrect, empirical observations should determine which combinations to pursue. In addition, there are four other hypotheses to explore. Whether this strategy will work in vivo remains to be determined. It should also be noted that MAbs and chemotherapy might also have additive effects in vivo but not in vitro if they target different anatomical compartments or have different biodistributions. This is testable in SCID/Daudi mice. By the same token, if MAbs change the biodistribution or pharmacokinetics of drugs in vivo, they might increase toxicity.

EXAMPLE 5

Assessing Strong Signaling Antibodies (mixtures or dimers) for Effects on SCID/lymphoma Mice of Advanced Disease when Combined with Chemotherapy or ITs.

Objectives and Approach

These agents are examined in combination in an in vivo SCID/Daudi model. Although several lymphoma cell lines grow in SCID mice, the SCID/Daudi model initially used and is well-characterized. The best regimens are also studied in SCID/DHL mice. The clinical endpoints previously established are used. It has already been shown that mice can be cured of minimal Daudi disease by a combination of a) the anti-CD19 MAb and an anti-CD22 IT (Ghetie et al., 1994a), b) chemotherapy and ITs (Ghetie et al., 1994b), and c) probably by chemotherapy and anti-CD19.

"Cure" is defined as 150 days disease-free survival and failure to adaptively transfer tumors (which takes 10 cells) to naive mice. In advanced disease, similar regimens induce prolonged remission but are not curative (Ghetie et al., 1996a). Indeed, no single therapeutic modality can cure advanced disseminated Daudi lymphoma. The ongoing strategy has been to use reagents which have different mechanisms of killing and which have different side effects and, therefore, can be given without significantly reducing the safe dose. Importantly, in the treatment of advanced lymphoma, the order in which the agents are given can determine their therapeutic benefit (Ghetie et al., 1996a).

Hence, Example 3 determines whether different agents sensitize cells to other agents. For this reason, not only are several different mixtures of agents examined but also administered in different temporal orders. In each case, it is determined whether MAbs change the $LD_{50}$, biodistribution and pharmacokinetics of the drugs. The agents tested include chemotherapy, IT and MAb (homo- and heterodimers). The chemotherapy±the IT are used concomitantly as indicated from previous studies (Ghetie et al., 1996a). MAbs are administered in the setting of minimal disease (post-chemotherapy) as well as pre-chemotherapy. MAbs and PAbs are also administered at the same time as chemotherapy as well as before based on the outcome of in vitro studies in Example 3 (Ghetie et al., 1992; Ghetie et al., 1994a; Ghetie et al., 1994b).

Methods a. SCID/Daudi and SCID/DHL mice

Female C.B-17 SCID/SCID mice are used. Six- to 10-week-old SCID mice are inoculated i.v. with 5' $10^6$ Daudi or DHL cells in 0.1 ml RPMI media. Mice are monitored daily and sacrificed at the onset of hind leg paralysis, a clinical symptom which precedes death (Uckun, 1996). However, in some instances, following therapy, death occurred prior to paralysis. In these instances, death is the end-point.

b. Therapeutic Protocols (i) Minimal Disease

SCID mice are inoculated with 5' $10^6$ Daudi or DHL cells 24 hours before treatrnent. In each study, four groups of 5 to 10 mice with an average weight of 20 g are used and treatment is administered on Days 1 through 4 after tumor injection as follows: 1) control mice are injected retroorbitally (RO) with PBS or saline; 2) mice are injected RO with an IT cocktail (RFB4-dgA [60 mg]+HD37-dgA [60 mg]); 3) mice receive either one of the following chemotherapeutic drugs: METH (112 mg), DOX (80 mg), CYT (1.6 mg) or CPT (640 mg), SOL (concentration to be determined), VIN (concentration to be determined) (all chemotherapeutics but CPT are administered i.v. on Days 1 through 4 divided into four equal amounts; CPT is injected intramuscular [i.m.] in an emulsion in intralipid two times per week for 4 weeks); 4) mice are given a combination of treatments 2) and 3) as described above. When therapy is initiated, the SCID mice have 1' $10^7$ disseminated tumor cells as described elsewhere (Uckun, 1996).

(ii) Advanced disease

Mice are treated 15 days after tumor cell inoculation with one of three therapeutic rotocols. (Death occurs at 30–40 days.) In Regimen #1, chemotherapy (DOX, CYT, OL, VIN or CPT) is commenced 15 days after tumor cell inoculation in doses described reviously (Ghetie et al., 1992; Ghetie et al., 1994a; Ghetie et al., 1994b). After the last injection of DOX or CYT and after the second injection of CPT, mice are rested for one week. The one week interval is based on results of other studies with ITs and on initial studies with MAbs. ITs or MAbs are then administered (Ghetie et al., 1996a). In Regimen #2, the IT or MAb is given first, mice are rested for 1 week and chemotherapy is then administered (Charley et al., 1990). In Regimen #3, the ITs or MAbs and chemotherapy are administered together. In this case, DOX or CYT are mixed with the IT or MAbs and injected i.v. in four equal doses. CPT is injected i.m. as previously described (Ghetie et al., 1994b). In some experiments, one of three chemotherapeutic drugs is given alone starting 7 days after tumor cell inoculation. Combination therapy is then used as in Regimen #1.

c. Survival

The comparison of survival curves are carried out using log-rank and Wilcoxon tests (Kalbfleisch and Prentice, 1980; Kapp et al., 1993). The median survival time (MST) is calculated by log-rank test at the 5% significance level.

d. Adoptive Transfer

Mice surviving for 150 days are sacrificed and $10^2$–$10^6$ cells from ovaries and spinal cords (Ghetie et al., 1994b) are injected i.v. into groups of healthy SCID mice. Adoptive recipients are followed for 150 days. At this time, the transfer of 100 tumor cells should cause death in the recipients (Ghetie et al., 1994b).

e. Biodistribution, Pharmacokinetics and $LD_{50}$'s

These will be done according to standard procedures (Ghetie et al., 1994b; Ghetie et al., 1996a; Itoh et al., 1993; Waller et al., 1991). Thus, primary lymphomas are also examined as described in Example 4.

Results

The results of these studies are already described in the Description of the Illustrative Embodiments

EXAMPLE 6

Direct Comparison of antiHER/2 Dimers With and Without Fc Regions

Cells. Cells from the breast cancer line, BT474, were maintained by serial passage in MEM containing 10% heat-inactivated fetal calf serum, 2 mM L-glutamine, 100 nM non-essential amino acids, 1 mM sodium pyruvate and 2% vitamins for MEM.

Preparation of anti-HER2 Mabs. Three different anti-Her2 Mabs were prepared as previously described in Example 1. These antibodies were designated as HER-50, HER-66, and HER-70.

MAbs. Mouse MAbs were used and prepared as described earlier in Example 1, following the protocol described by Ghetie et al. (1991).

Preparation of IgG homodimers. Each different monoclonal anti-HER/2 was dimerized to produce a homoconjugate following the protocols previously described in Example 1. The resulting IgG homodimers were then mixed together in a 1:1:1 ratio to yield the IgG homoconjugate mixture.

Preparation of F(ab')$_2$ homoconjugate mixture. The F(ab')$_2$ antibody preparations were prepared from the preceding IgG homodimer mixture by with pepsin to remove the Fc portions of the molecules. The resulting F(ab')2 homodimer preparation was then absorbed with protein A to remove any undigested IgG antibodies.

$^3$H-Thymidine Assay. The anti-proliferative activity of different MAb monomers and dimers on Daudi cells was determined using a [$^3$H]-thymidine incorporation assay (Ghetie et al., 1988).

Measurement of cytotoxic effects. One hundred microliters of BT474 cells in media were placed in a 96 well microtiter plate at a concentration of $10^5$ cells/ml. Cells were allowed to adhere overnight and then treated with either the IgG homoconjugate mixture or with the F(ab')$_2$ homoconjugate mixture for 72 hours (FIG. 9) or (FIG. 10) followed by a pulse with $^3$H-thymidine for 4 hours (FIG. 10) or 6 hours (FIG. 10). Cytotoxic effects were measured as the percent of $^3$H-thymidine incorporation compared to a standard control. The results clearly indicate that the F(ab')$_2$ homoconjugate mixture was as active as, or possibly even more active, than the IgG homoconjugate mixture. Thus demonstrating that no Fc regions are required in the conjugates for cytotoxic activity to be expressed.

EXAMPLE 7

Comparison of antiHER/2 Monomers and Dimers Killing Activity

Prostate carcinoma cell lines PC3, LNCap and DU145 were cultured in RPMI and 10% FBS at 37° C. in a 5% $CO_2$ incubator. Media were removed and cells were washed twice with PBS. Cell monolayers were trypsinized for about 5 minutes, resuspended in complete media and spun down. Supernatants were removed and the pellets were resuspended in complete media.

Cells were aliquoted into 1.5 ml microcentrifuge tubes at $1 \times 10^6$/tube and spun. Supernatants were removed and pellets were briefly vortexed. One µg of each antibody was added, and the cells were incubated for 15 minutes on ice. Cells were washed with 1 ml Hanks balanced salt solution, spun, the supernatants removed and the resulting pellets were vortexed. The secondary, FITC-GAMIg antibody was added at 0.25 µg/tube and incubated for 15 minutes on ice in the dark. Cells were washed as before and resuspended in 1 ml of 1% paraformaldehyde. The control is secondary antibody alone.

The results with PC3 (FIG. 10A), LNCap (FIG. 10B) and DU145 (FIG. 10C) show that all three cell lines stain with the 3 anti-HER-2 MAbs used thus showing that all 3 cell lines express HER2 antigen.

Having shown that the cell lines express the HER antigen, the ability of anti-ER2 dimers to kill the carcinoma cells was next examined.

Cells were prepared in the same manner and then were dispensed into a 96-well flat bottom plate at $1 \times 10^4$/well in a volume of 100 µl and incubated overnight to allow the cells to attach to the plate. The next morning cells were treated with antibodies (in triplicate) using 100 µl/well. At 48 hours, 1 µCi of $^3$H-Thymidine was added. After 6 hours, plates were harvested and samples counted for $^3$H-Thymidine incorporation. The control was untreated cells.

The results clearly show that the anti-HER2 Mab HER-66 dimer (FIG. 11A) and HER-50 dimer (FIG. 11B) inhibit and even kill the carcinoma cells whereas the monomeric gorms of the Mabs have no effect on the growth of the cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adair, "Engineering antibodies for therapy," *Immunol. Rev.*, 192; 130:5–40, 1992.

Ahsmann, Vantol, Oudemangruber, Lokhorst, Uytdehaag, Schuurman, Bloem, "The SCID mouse as a model for multiple myeloma," *Br. J. Haematol.*, 89:319–327, 1995.

Akiyama, Olden, Yamada, "Fibronectin and integrins in invasion and metastasis," *Cancer Metastasis Rev.*, 14:173–189, 1995.

Altman, Moss, Goulder, Barouch, McHeyzer-williams, Bell, McMichael, Davis, "Phenotypic analysis of antigen-specific T lymphocytes," *Science*, 274:94–96.

Baiocchi, Ross, Tan, Chou, Sullivan, Haldar, Monne, Seiden, Narula, Sklar, Croce, Caligiuri, "Lymphomagenesis in the SCID-hu mouse involves abundant production of human interleukin-10," *Blood*, 85:1063 –1074, 1995.

Beckwith et al., "Anti-IgM mediated growth inhibition of a human B-lymphoma cell line is independent of phosphatidylinositol turnover and protein kinase C activation and involves tyrosine phosphorylation," *J. Immunol.*, 147:2411–2418, 1991.

Blum, Stevens, DeFranco, "Role of the mu immunoglobulin heavy chain transmembrane and cytoplasmic domains in B cell antigen receptor expression and signal transduction," *J. Biol. Chem.*, 268:27236–27245, 1993.

Bosma, Fried, Custer, Carroll, Gibson, Bosma, "Evidence of finctional lymphocytes in some (leaky) SCID mice," *J. Exp. Med.*, 167:1016–1033, 1988.

Boyle, Tamburini, Berend, Kizilbash, Borowitz, Lyerly, "Human B-cell lymphoma in severe combined immuno-deficient mice after active infection with Epstein-Barr virus," *Surgery*, 112:378–386, 1992.

Bridges et al., "Selective in vivo antitumor effect of monoclonal anti-I-A antibody on B cell lymphoma," *J. Immunol.*, 139:4242–4249, 1987.

Brown, Miller, Levy, "Antiidiotype antibody therapy of B-cell lymphoma," *Semin. Oncol.*, 16:199–210, 1989.

Brunner, Mogil, LeFace, Yoo, Mahboubi, Echeverri, Martin, Force, Lynch, Ware, Green, "Cell-autonomous Fas (CD95)/Fas-ligand interaction mediates activation-induced apoptosis in T-cell hybridomas," *Nature*, 373:441–444, 1995.

Buchsbaum, Wahl, Normolle, Kaminski, "Therapy with unlabeled and 131I-labeled pan-B-cell monoclonal antibodies in nude mice bearing Raji Burkitt's lymphoma xenografts," *Cancer Res.*,52:6476–6481, 1992.

Campana, Janossy, Bofill, Trejdosiewicz, Ma, Hoffbrand, Mason, LeBacq, Forster, "Human B cell development. I. Phenotypic differences of B lymphocytes in the bone marrow and peripheral lymphoid tissue," *J. Immunol.*, 134:1524–1529, 1985.

Caron et al., "Engineered humanized dimeric forms of IgG are more effective antibodies", *J. Exp. Med.*, 176:1191–1195, 1992.

Carter, Tuveson, Park, Rhee, Fearon, "The CD19 complex of lymphocytes-B-activation of phospholipase-C by a protein tyrosine kinase-dependent pathway that can be enhanced by the membrane IgM complex," *J. Immunol.*, 147:3663–3671, 1991.

Charley, Tharp, Locker, Deng, Goslen, Mauro, McCoy, Abell, Jegasothy, "Establishment. of a human cutaneous T-cell lymphoma in C.B-17 SCID mice," *J. Invest. Dermatol.*, 94:381–384, 1990.

Chen, Feng, Schilder, "Effect of vincristine, adriamycin and glucocorticoids on myeloma cells in vitro," *Acta Haematol.*, 89:61–69, 1993.

Chen, Williams, Fanslow, Bankert, "Human antibody response in human peripheral blood leukocyte/severe combined immunodeficient chimeric model is dependent on B and T cell costimulation via CD40/CD40 ligand," *J. Immunol.*, 155:2833–2840, 1995.

Choi, Boise, Gottschalk, Quintans, Thompson, Klaus, "The role of bcl-XL in CD40-mediated rescue from anti-mu-induced apoptosis in WEHI-231 B lymphom.a cells," *Eur. J. Immunol.*, 25:1352–1357, 1995.

Chokri, Girard, Borrelly, Oleron, Rometlemonne, Bartholeyns, "Adoptive immunotherapy with bispecific antibodies—targeting through macrophages," *Res. Immunol.*, 143:95–99, 1992.

Clark and Ledbetter, "Activation of human B cells mediated through two distinct cell surface differentiation antigens," *Proc. Natl. Acad. Sci., USA*, 83:4494–4498, 1986.

Clark and Shu, "Activation of human B cell proliferation through surface Bp35 (CD20) polypeptides or immunoglobulin receptors," *J. Immunol.*, 138:720–725, 1987.

Coligan et al., eds., *Current protocols in immunology*, New York, John Wiley and Sons, 6.1.1, 1991.

Crawford and Catovsky, "In vitro activation of leukaemic B cells by interleukin-4 and antibodies to CD40," *Immunology*, 80:40–44, 1993.

Darzynkiewicz, Bruno, Del Bino, Gorczyca, Hotz, Lassota, Traganos, "Features of apoptotic cells measured by flow cytometry," *Cytometry*, 13:795–808, 1992.

Denkers et al., "Influence of antibody isotype of passive serotherapy of lymphoma," *J. Immunol.*, 135:2183–2186, 1995.

Dhein, Walczak, Baumler, Debatin, Krammer, "Autocrine T-cell suicide mediated by APO-1/(Fas/CD95)," *Nature*, 373:438–441, 1995.

Dillman, "Antibodies a cytotoxic therapy," *J. Clin. Oncol.*, 12(7):1497–1515, 1994.

Dorken, Schwarz, Feller, Hammerling, Hunstein, "Production of monoclonal antibodies for the diagnosis of minimal infiltration of leukemic cells into the bone marrow," *Verh. Dtsch. Ges. Path.*, 67:65–69, 1983.

Dyer, Hale, Hayhoe, Waldmann, "Effects of CAMPATH-1 antibodies in vivo in patients with lymphoid malignancies: Influence of antibody isotype," *Blood*, 73:1431–1439, 1989.

Edward, "Integrins and other adhesion molecules involved in melanocytic tumor progression," *Curr. Opin. Oncol.*, 7:185–191, 1995.

Faris, Gaskin, Parsons, Fu, "CD40 signaling pathway: Anti-CD40 monoclonal antibody induces rapid dephosphorylation and phosphorylation of tyrosine-phosphorylated proteins including protein tyrosine kinase Lyn, Fyn and Syk and the appearance of a 28-kD tyrosine phosphorylated protein," *J. Exp. Med.*, 179:1923–1931, 1994.

Fischer, Blanche, Le Bidois, Bordigoni, Garnier, Niaudet, Morinet, Le Deist, Fischer, Griscelli, Hirn, "Anti-B-cell monoclonal antibodies in the treatment of severe B-cell lymphoproliferative syndrome following bone marrow and organ transplantation," *N. Engl. J. Med.*, 324:1451–1456, 1991.

Fluckiger, Rossi, Bussel, Byron, Banchereau, DeFrance, "Responsiveness of chronic lymphocytic leukemia B cells activated via surface Igs or CD40 to B-cell tropic factors," *Blood*, 80:3173–3181, 1992.

Fraker and Speck, Jr, "Protein and cell membrane iodinations with a sparingly soluble chlorarnide, 1,3,4,6-tetrachloro-3a,6a-diphenylglycoluril", *Biochem. Biophys. Res. Commun.*, 80:849–857, 1978.

Funakoshi, Longo, Beckwith, Conley, Tsarfaty, Tsarfaty, Armitage, Fanslow, Spriggs, Murphy, "Inhibition of human B-cell lymphoma growth by CD40 stimulation," *Blood*, 83:2787–2794, 1994.

Ghetie et al., "The use of immunoconjugates in cancer therapy," *Exp. Opin. Invest. Drugs.*, 5(3):309–321, 1996b.

Ghetie, May, Till, Uhr, Ghetie, Knowles, Relf, Brown, Wallace, Janossy, Amlot, Vitetta Thorpe, "Evaluation of ricin A chain-containing immunotoxins directed against CD19 and CD22 antigens on normal and malignant human B-cells as potential reagents for in vivo therapy," *Cancer Res.*, 48:2610–2617, 1988.

Ghetie, Picker, Richardson, Tucker, Uhr, Vitetta, "Anti-CD19 inhibits the growth of human B-cell tumor lines in vitro and of Daudi cells in SCID mice by inducing reversible cell cycle arrest," *Blood*, 83:1329–1336, 1994a.

Ghetie, Podar, Gordon, Pantazis, Uhr, Vitetta, "Combination immunotoxin treatment and chemotherapy in SCID mice with advanced, disseminated Daudi lymphoma," *Int. J. Cancer*, 68:93–96, 1996a.

Ghetie, Richardson, Tucker, Jones, Uhr, Vitetta, "Disseminated or localized growth of a human B-cell tumor (Daudi) in SCID mice," *Int. J. Cancer*, 45:481–485, 1990.

Ghetie, Thorpe, Ghetie, Knowles, Uhr, Vitetta, "The GLP large scale preparation of immunotoxins containing deglycosylated ricin A chain and a hindered disulfide bond," *J. Immunol. Methods*, 142:223–230, 1991.

Ghetie, Tucker, Richardson, Uhr, Vitetta, "Eradication of minimal disease in severe combined immunodeficient mice with disseminated Daudi lymphoma using chemotherapy and an immunotoxin cocktail," *Blood*, 84:702–707, 1994b.

Ghetie, Tucker, Richardson, Uhr, Vitetta, "The anti-tumor activity of an anti-CD22-immunotoxin in SCID mice with disseminated Daudi lymphoma is enhanced by either an anti-CD19 antibody or an anti-CD19 immunotoxin," *Blood*, 80:2315–2320, 1992.

Goding, In: *Monoclonal Antibodies: Principles and Practices*, New York, Academic Press, 1983.

Gold and DeFranco, "Biochemistry of B lymphocyte activation," *Adv. Immunol.*, 55:221–295, 1994.

Gold, Chan, Turck, DeFranco, "Membrane Ig cross-linking regulates phosphatidylinositol 3-kinase in B lymphocytes," *J. Immunol.*, 148:2012–2022, 1992.

Gold, Law, DeFranco, "Stimulation of protein tyrosine phosphorylation by the B-lymphocyte antigen receptor," *Nature*, 345:810–813, 1990.

Goldstein and Watts, "Identification of distinct domains in CD40 involved in B7-1 induction or growth inhibition," *J. Immunol.*, 157:2837–2843, 1996.

Gorczyca, Gong, Darzynkiewicz, "Detection of DNA strand breaks in individual apoptotic cells by the in situ terminal deoxynucleotidyl transferase and nick translation assays," *Cancer Res.*, 53:1945–1951, 1993.

Gottschalk, Boise, Thompson, Quintans, "Identification of immunosuppressant-induced apoptosis in a murine B-cell line and its prevention by bcl-x but not bcl-2," *Proc. Natl. Acad. Sci., USA*, 91:7350–7354, 1994.

Greenwood et al., "Engineering multiple-domain forms of the therapeutic antibody CAMPATH-IH: Effects on complement lysis", *Therap. Immunol.*, 1:247–255, 1994.

Guo et al., "Inhibition of human melanoma growth and metastasis in vivo by anti-CD44 monoclonal antibody," *Cancer Res.*, 54:1561–1565, 1994.

Hale, Clark, Waldmann, "Therapeutic potential of rat monoclonal antibodies: Isotype specificity of antibody-dependent cell-mediated cytotoxicity with human lymphocytes," *J. Immunol.*, 134:3056–3061, 1985.

Hale, Clarke, Marcus, Winter, Dyer, Phillips, Riechmann, Waldman, "Remission induction in non-Hodgkin lymphoma with reshaped human monoclonal antibody," *Lancet*, 2:1394–1399, 1988.

Hamblin et al., "Preliminary experience in treating lymphocytic leukaemia with antibody to immunoglobulin idiotypes on the cell surfaces," *Br. J. Cancer*, 42:495–502, 1980.

Hamblin, Cattan, Glennie, Mackenzie, Stevenson, Watts, Stevenson, "Initial experience in treating human lymphoma with a chimeric univalent derivative of monoclonal anti-idiotype antibody," *Blood*, 69:790–797, 1987.

Hansen, Martin, Beatty, G., Clark, Ledbetter, "Human T lymphocyte cell surface molecules defined by the workshop monoclonal antibodies ('T cell protocol')," *In: Leukocyte Typing: Human Leukocyte Markers Detected By Monoclonal Antibodies* (Bernard et al., eds.), New York: Springer-Verlag, 195, 1984.

Hekman, Honselaar, Vuist, Sein, Rodenhuis, Huininik, Somers, Rumke, Melief, "Initial experience with treatment of human B cell lymphoma with anti-CD19 monoclonal antibody," *Cancer Immunol., Immunother.*, 32:364–372, 1991.

Hellström et al., "Immunoconjugates and Immunotoxins for Therapy of Carcinomas," *Adv. Pharmacol.*, 33:349–388, 1995.

Herlyn and Koprowski, "IgG2a monoclonal antibodies inhibit human tumor growth through interaction with effector cells," *Proc. Natl. Acad. Sci. USA*, 79:4761–4765, 1982.

Hoagland, "Hematologic complications of cancer chemotherapy," *In: Chemotherapy Source Book*, Perry, Ed., Baltimore, Williams and Wilkins, 498–507, 1992.

Holder, Wang, Milner, Casamayor, Armitage, Spriggs, Fanslow, Maclennan, Gregory, Gordon, "Suppression of apoptosis in normal and neoplastic human B lymphocytes by D\CD40 ligand is independent of Bcl-2 induction," *Eur. J. Immunol.*, 23:2368–2371, 1993.

Holliger, Prospero, Winter, "Diabodies: Small bivalent and bispecific antibody fragments," *Proc. Natl. Acad. Sci. USA* 90:6444–6448.

Hooijberg et al., "Enhanced antitumor effects of CD20 over CD19 monoclonal antibodies in a nude mouse xenograft model," *Cancer Res.*, 55(4):840–846, 1995a.

Hooijberg et al., "Eradication of large human B cell tumors in nude mice with unconjugated CD20 monoclonal antibodies and interleukin 2," *Cancer Res.*, 55(12):2627–2634, 1995b.

Huang and Vitetta, "A monoclonal anti-human IL-6 receptor antibody inhibits the proliferation of human myeloma cells," *Hybridoma*, 12:621–630, 1993.

Huang, Richardson, Vitetta, "Anti-CD54 (ICAM-1) has antitumor activity in SCID mice with human myeloma cells," *Cancer Res.*, 55:610–616, 1995.

Hurwitz, Hozier, LeBien, Minowada, Gaji-Peczalska, Kubonishi, Kersey, "Characterization of a leukemic cell line of the pre-B phenotype," *Int. J. Cancer*, 23:174–18C, 1979.

Huschtscha, Bartier, Ross, Tattersall, "Characteristics of cancer cell death after exposure to cytotoxic drugs in vitro," *Br. J. Cancer*, 73:54–60, 1996.

Hutchcroft, Harrison, Geahlen, "B lymphocyte activation is accompanied by phosphorylation of a 72-kDa protein-tyrosine kinase," *J. Biol. Chem.*, 266:14846–14849, 1991.

Inui, Kaisho, Kikutani, Stamenkovic, Seed, Clark, Kishimoto, "Identification of the intracytoplasmic region essential for signal transduction through a B cell activation molecule, CD40," *Eur. J. Immunol.*, 20:1747–1753, 1990.

Isakson, Pure, Uhr, Vitetta, "Induction of proliferation and differentiation of neoplastic B cells by anti-immunoglobulin and T-cell factors," *Proc. Natl. Acad. Sci., USA*, 78:2507–2511, 1981.

Itoh, Shiota, Takanashi, Hojo, Satoh, Matsuzawa, Moriyama, Watanabe, Hirai, Mori, "Engraftment of human non-Hodgkin lymphomas in mice with severe combined immunodeficiency," *Cancer*, 72:2686–2694, 1993.

Johnson, Watt, Betts, Davies, Jordan, Norton, Lister, "Isolated follicular lymphoma cells are resistant to apoptosis and can be grown in vitro in the CD40/stromal cell system," *Blood*, 82:1848–1857, 1993.

Ju, Panka, Cul, Ettinger, El-Khatib, Sherr, Stanger, Marshak-Rothstein, "Fas(CD95)/FasL interactions required for programmed cell death after T-cell activation," *Nature*, 373:444–448, 1995.

Kaetzel et al., "The polymeric immunoglobulin receptor (secretory component) mediates transport of immune complexes across epithelial cells: a local defense function for IgA", *Proc. Natl. Acad. Sci. USA*, 88:8796–8800, 1991.

Kalbfleisch and Prentice, In: *The Statistical Analysis of Failure Time Data* (Anonymous), New York, Wiley, 1–321, 1980.

Kaminski et al., "Importance of antibody isotype in monoclonal anti-idiotype therapy of a murine B-cell lymphoma," *J. Immunol.*, 136:1123–1130, 1986.

Kaminski, Zasadny, Francis, Milik, Ross, Moon, Crawford, Burgess, Petry, Butchko, Glenn, Wahl, "Radioimmunotherapy of B-cell lymphoma with [131I]anti-B1 (anti-CD20) antibody," *N. Engl. J. Med.*, 329:459–465, 1993.

Kapp, Wolf, Hummel, Pawlita, von Kalle, Dallenbach, Schwonzen, Krueger, Müller-Lantzsch, Fonatsch, Stein, Diehi, "Hodgkin's lymphoma-derived tissue serially transplanted into severe combined immunodeficient mice," *Blood*, 82:1247–1256, 1993.

Kim et al., "Identifying amino acid residues that influence plasma clearance of murine IgG1 fragments by site-directed mutagenesis", *Eur. J. Immunol.*, 24:542–548, 1994.

Klein, Klein, Nadkarni, Nadkarni, Wigzell, Clifford, "Surface IgM-kappa specificity on a Burkitt lymphoma cell in vivo and in derived culture lines," *Cancer Res.*, 28:1300–1310, 1989.

Kluin-Nelemans, Beverstock, Mollevanger, Wessels, Hoogendoom, Willemze, Falkenburg, "Proliferation and cytogenetic analysis of hairy cell leukemia upon stimulation via the CD40 antigen," *Blood*, 84:3134–3141, 1994.

Knapp, Dorken, Gilks, Rieber, Schmidt, Stein, Von dem Borne, eds. *Leukocyte Typing IV. White Cell Differentiation Antigens*, New York, Oxford University Press, 1989.

Kohler, Dhein, Alberti, Krammer, "Ultrastructural analysis of apoptosis induced by the monoclonal antibody anti-APO-1 on a lymphoblastoid B cell line," *Ultrastruct. Pathol.*, 14:513–518, 1990.

Krolick, Villemez, Isakson, Uhr, Vitetta, "Selective killing of normal or neoplastic B cells by antibodies coupled to the A chain of ricin," *Proc. Natl. Acad. Sci., USA*, 77:5419–5423, 1980.

Kung, Zetterberg, Sherwood, Schimke, "Cytotoxic effects of cell cycle phase specific agents: Result of cell cycle perturbation," *Cancer Res.*, 50:7307–7317, 1990.

Kuwahara, Igarashi, Kawai et al., "Induction of tyrosine phosphorylationin human B lineage cells by crosslinking mb-I molecule of B cell receptor-related heterodimer complex. *Biochem. Ciophys. Res. Commun.*, 197:1563–1569, 1993.

Laemmli, "Cleavage of structural proteins during the assembly of the head of bacteriophage," *Nature*, 227:680–685, 1970.

Law, Gold, DeFranco, "Examination of B lymphoid cell lines for membrane immunoglobulin-stimulated tyrosine phosphorylation and src-family tyrosine kinase and mRNA expression," *Mol. Immunol.*, 29:917–926, 1992.

Leblond, Sutton, Dorent, Davi, Bitker, Gabarre, Charlotte, Ghoussoub, Fourcade, Fischer, Gandjbakhch, Binet, Raphael, "Lymphoproliferative disorders after organ transplantation: A report of 24 cases observed in a single center," *J. Clin. Oncol.*, 13:961–968, 1995.

Levy and Miller, "Therapy of lymphoma directed at idiotypes", *J. Natl. Cancer Inst. Monographs*, 10:61–68, 1990.

Li, Shen, Ghetie, May, Till, Ghetie, Uhr, Janossy, Thorpe, Arelot, Vitetta, "The epitope specificity and tissue reactivity of four murine monoclonal anti-CD22 antibodies," *Cell. Immunol.*, 118:85–99, 1989.

Ling, El-Naggar, Priebe, Perez-Soler, "Cell cycle-dependent cytotoxicity, g2/m phase arrest and disruption of p34cdc2/cyclin b1 activity induced by doxorubicin in synchronized p388 cells," *Mol. Pharmocol.*, 49:832–841, 1996.

Lukic and Mitchison, "Self- and allo-specific suppressor T cells evoked by intravenous injection ofF protein," *Eur. J. Immunol.*, 14:766–768, 1984.

Marches, Racila, Tucker, Picker, Mongini, Hsueh, Vitetta, Scheuermann, Uhr, "Tumor dormancy and cell signaling III: Role of hypercrosslinking of IgM and CD40 on the induction of cell cycle arrest and apoptosis in B lymphoma cells," *Therap. Immunol.*, 2:125–136, 1996.

Martin, Hansen, Vitetta, "A ricin A chain-containing immunotoxin that kills human T lymphocytes in vitro," *Blood*, 66:908–912, 1985.

Meeker, Lowder, Maloney, Miller, Thielemans, Warnke, Levy, "A clinical trial of anti-idiotype therapy for B cell malignancy," *Blood*, 65:1349–1363, 1985.

Meggetto, Muller, Henry, Selves, Mariame, Brousset, Saati, Delsol, "Epstein-Barr virus (EBV)-associated lymphoproliferations in severe combined immunodeficient mice transplanted with Hodgkin's disease lymph nodes: Implication of EBV-positive bystander B lymphocytes rather than EBV-infected reed-stemberg cells," *Blood*, 87:2435–2442, 1996.

Merino, Grillot, Simonian, Muthukkumar, Fanslow, Bondada, Núñez, "Modulation of anti-IgM-induced B cell apoptosis by Bcl-$x_L$ and CD40 in WEHI-231 cells," *J. Immunol.*, 155:3830–3838, 1995.

Messinger, Yanishevski, Avramis, Ek, Chelstrom, Gunther, Myers, Irvin, Evans, Uckun, "Treatment of human B-cell precursor leukemia in SCID mice using a combination of the investigational biotherapeutic agent B43-PAP with cytosine arabinoside," *Clin. Cancer Res.*, 2:1533–1542, 1996.

Minderman, Brons, Linssen, Pennings, Wessels, Boezeman, Haanen, "Effect of doxorubicin exposure on cell-cycle kinetics of human leukemia cells studied by bivariate flow cytometric measurement of 5-lodo-2-deoxyuridine incorporation and DNA content," *Exp. Hematol.*, 19:1008–1012, 1991.

Morrison and Oi, "Genetically engineered antibody molecules," *Adv. Immunol.*, 44:65–91, 1989.

Murphy, Funakoshi, Beckwith, Rushing, Conley, Armitage, Fanslow, Rager, Taub, Ruscetti, Longo, "Antibodies to CD40 prevent Epstein-Barr Virus-mediated human B-cell lymphomagenesis in severe combined immune deficient mice given human peripheral blood lymphocytes," *Blood*, 86:1946–1953, 1995.

Nakamura, Sekar, Kubagawa, Cooper, Signal transduction in human B cells initiated via Igγ ligation", *International Immunology*, 5:1309–1315, 1993.

National Institutes of Health, "Radioiodination of cells," In: *Current Protocols in Immunology* (Coligan et al., Eds.), New York, John Wiley and Sons, 1992.

Newton, Reeves, Gralnick, Mohla, Yamada, Olden, Akiyama, "Inhibition of experimental metastasis of human breast carcinoma cells in athymic nude mice by anti-alpha(5)beta(1) fibronectin receptor integrin antibodies," Int,"*J. Oncol.*, 6:1063–1070, 1995.

Pack, Müller, Zahn, Plückthun, "Tetravalent miniantibodies with high avidity assembing in *Escherichia coli*, " *J. Mol. Biol.* 246:28–34.

Pack and Plückthun, "Miniantibodies: Use of amphipathic helices to produce functional, flexibly linked dimeric Fv fragments with high avidity in *Escherichia coli*," *Biochemistry* 31:1579–1584.

Page and Defranco, "Role of phosphoinositide-derived second messengers in mediated anti-IgM-induced growth arrest of WEHI-231 B lymphoma cells," *J. Immunol.*, 140:3717–26, 1988.

PCT application WO 92/04053.

Petru, Sevin, Haas, Ramos, Perras, "A correlation of cell cycle perturbations with chemosensitivity in human ovarian cancer cells exposed to cytotoxic drugs in vitro," *Gynecol. Oncol.*, 58:48–57, 1995.

Pittman, Strickland, Ireland, "Polymerization of tubulin in apoptotic cells is not cell cycle dependent," *Exp. Cell Res.*, 215:263–272, 1994.

Pleiman, D'Ambrosio, Cambier, "The B-cell antigen receptor complex: structure and signal transduction, *Immunol Today*, 15:393–399, 1994.

Popov, Hubbard, Ward, "A novel and efficient route for the isolation of antibodies that recognise T cell receptor Vαs," *Mol. Immunol.* 33:493–502.

Press et al., "Endocytosis and degradation of monoclonal antibodies targeting human B cell malignancies", *Cancer Res.*, 49:4906–4912, 1989.

Press, Appelbaum, Ledbetter, Martin, Zarling, Kidd, Thomas, "Monoclonal antibody 1 F5 (anti-CD20) serotherapy of human B cell lymphomas," *Blood*, 69:584–591, 1987.

Press, Eary, Appelbaum, Martin, Badger, Nelp, Glenn, Butchko, Fisher, Porter, Matthews, Fisher, Bernstein, "Radiolabeled-antibody therapy of B-cell lymphoma with autologous bone marrow support," *N. Engl. J. Med.*, 329:1 219–1224, 1993.

Pulvertaft, "Cytology of Burkitt's tumour (African lymphoma)," *Lancet*, 1:238–240, 1964.

Qi et al., "Antibody-targeted lymphokine-activated killer cells inhibit liver micrometastases in severe combined immunodeficient mice," *Gastroenterology* 109(6):1950–1957, 1995.

Racila, Hsueh, Marches, Tucker, Krammer, Scheuermann, Uhr, "Tumor dormancy and cell signaling: Anti-μ-induced apoptosis in human B-lymphoma cells is not caused by an APO-1—APO-1 ligand interaction," *Proc. Natl. Acad. Sci., USA*, 93:2165–2168, 1996.

Racila, Scheuermann, Picker, Yefenof, Tucker, Chang, Marches, Street, Vitetta, Uhr, "Tumor dormancy and cell signaling. II. Antibody as an agonist in inducing dormancy of a B cell lymphoma in SCID mice," *J. Exp. Med.*, 181:1539–1550, 1995.

Rankin, Hekmann, Sommers, van Bokkel Huinink, "Treatment of two patients with B-cell lymphoma with monoclonal anti-idiotype antibodies," *Blood*, 65:1373–1381, 1985.

Ren, Morio, Fu, Geha, "Signal transduction via CD40 involves activation of lyn kinase and phosphatidylinositol-3-kinase and phosphorylation of phospholipase CT2, " *J. Exp. Med.*, 179:673–680,1994.

Richards, Golds, Hurihane, DeFranco, Matsuuchi, "Reconstitution of B cell antigen receptor-induced signaling events in a nonlymphoid cell line by expressing the Syk protein-tyrosine kinase," *J. Biol. Chem.*, 271:6458–6466, 1996.

Riethmüller et al., "Randomised trial of monoclonal antibody for adjuvant therapy of resected Dukes'Colorectal carcinoma," *Lancet* 343:1174–1177, 1994.

Rowe, Young, Corcker, Stokes, Henderson, Rickinson, "Epstein-Barr virus (EBV)-associated lymphoproliferative disease in the SCID mouse model: Implications for the pathogenesis of EBV-positive lymphomas in man," *J. Exp. Med.*, 173:147–158, 1991.

Ruiz, Dunon, Sonnerberg, Imhof, "Suppression of mouse melanoma metastasis by EA-1, a monoclonal antibody specific for $\alpha_6$ integrins," *Cell Adhes. Commun.*, 1:67–81, 1993.

Sato et al., "Efficient induction of apoptosis in cultured rat glomerular mesangial cells by dimeric monoclonal IgA anti-Thy-1 antibodies," *Kidney Int.*, 51:173–181, 1997.

Scheuermann, Racila, Tucker, Yefenof, Street, Vitetta, Picker, Uhr, "Lyn tyrosine kinase signals cell cycle arrest but not apoptosis in B-lineage lymphoma cells," *Proc. Natl. Acad. Sci., USA*, 91:4048–4052, 1994.

Schreiber et al., "An unmodified anticarcinoma antibody, BR96, localizes to and inhibits the outgrowth of human tumors in nude mice", *Cancer Res.*, 52:3262–3266, 1992.

Schumaker, "PKALC: A basic interactive program for statistic and pharmacokinetic analysis of data", *Drug Metab. Rev.*, 17:331–348, 1986.

Scott et al., "Lymphoma models for B-cell activation and tolerance. II. Growth inhibition by anti-m of WEHI-231 and the selection and properties of resistant mutants", *Cell Immunol.*, 93:124–131, 1985.

Scott et al., "p185HER2 signal transduction in breast cancer cells," *J. Biol. Chem.*, 266(August 5):14300–14305, 1991.

Scott, Grdina, Shi, "T cells commit suicide, but B cells are murdered," *J. Immunol.*, 156:2352–2356, 1996.

Senderowicz, Vitetta, Headlee, Ghetie, Uhr, Figg, Lush, Stetler-Stevenson, Kershaw, Kingma, Jaffe, Sausville, "Complete sustained response of a refractory, posttransplantation, large B-Cell lymphoma to an anti-CD22 immunotoxin," *Ann. Intern. Med.*, 126:882–885, 1997.

Sevin, Pollack, Averette, Ramos, Greening, Evans, "In vivo chemosensitivity testing in patients with gynecologic malignancies and nude mouse xenografts by monitoring cell kinetic parameters and DNA distribution patterns: A preliminary report," *Gynecol. Oncol.*, 24:27–40, 1986.

Shah, Halloran, Ferris, Levine, Bourret, Goldmacher, Blattler, "Anti-B4-blocked ricin immunotoxin shows therapeutic efficacy in four different SCID mouse tumor models," *Cancer Res.*, 53:1360–1367, 1993.

Shopes, "A genetically engineered human IgG mutant with enhanced cytolytic activity," *J. Immunol.*, 148(9):2918–2922, 1992.

Shuford et al., "Effect of light chain V region duplication on IgG oligomerization and in vivo efficacy", *Science* 252:724–727, 1991.

Smith and Morrison, "Recombinant polymeric IgG: An approach to engineering more potent antibodies", *Bio/Technol.*, 12:683–688, 1994.

Song et al., "Stimulation of transcytosis of the polymeric immunoglobulin receptor by dimeric IgA", *Proc. Natl. Acad. Sci. USA*, 91:163–166, 1994.

Terstappen, Mickaels, Dost, Loken, "Increased light scattering resolution facilitates multidimensional flow cytometric analysis," *Cytometry*, 11:506–512, 1990.

Torbett, Picchio, Mosher, "hu-PBL-SCID mice: A model for human immune function, AIDS and lymphomagenesis. *Immunol. Rev.*, 124:139–151, 1991.

Trauth et al., "Monoclonal antibody-mediated tumor regression by induction of apoptosis," *Science*, 245:301–305, 1989.

Trauth, Klas, Peters, Matzku, Moller, Falk, Debatin, Krammer, "Monoclonal antibody-mediated tumor regression by induction of apoptosis," *Science*, 245:301–305, 1989.

Trucco and De Petris, "Determination of equilibrium binding parameters of monoclonal antibodies specific for cell surface antigens," In: *Immunological Methods. Vol. II*, (Lefkovits and Pernis, Eds.), New York, Academic Press, 1–26, 1981.

Tsurusawa, Niwa, Katano, Fujimoto, "Methotrexate cytotoxicity as related to irreversible S phase arrest in mouse L1210 leukemia cells," *Jpn. J. Cancer Res.*, 81:85–90, 1990.

Uckun, "Severe combined immunodeficient mouse models of human leukemia," *Blood*, 88:1135–1146, 1996.

Vermes et al., "A novel assay for apoptosis. Flow cytometric detection of phosphatidylserine expression on early apoptotic cells using fluorescein labeled Annexin V.", *J. Immunol. Methods*, 184(1):39–51, 1995.

Veronese, Veronesi, D'Andrea, Del Mistro, Indraccolo, Mazza, Mion, Zamarchi, Menin, Panozzo, Amadori, Chieco-Bianchi, "Lymphoproliferative disease in human peripheral blood mononuclear cell-injected SCID mice. I. T lymphocyte requirement for B-cell tumor generation," *J. Exp. Med.*, 176:1763–1767, 1992.

Vervoordeldonk et al., "Fc-gamma receptor II (CD32) on malignant B cells influences modulation induced by anti-CD19 monoclonal antibody", *Blood*, 83(6):1632–1639, 1994.

Vial and Descotes, "Clinical toxicity of interleukin-2," *Drug Safety*, 7:417–433, 1992.

Vitetta and Uhr, "Monoclonal antibodies as agonists: an expanded role for their use in cancer therapy," *Cancer Res.*, 54:5301–5309, 1994.

Waldmann, "Immune receptors: Targets for therapy of leukemia/lymphoma, autoimmune diseases and for the prevention of allograft rejection," *Annu. Rev. Immunol.*, 10:675–704, 1992.

Waller, Kamel, Cleary, Majumdar, Schick, Lieberman, Weissman, "Growth of primary T-cell non-Hodgkin's lymphomata in SCID-hu mice: Requirement for a human lymphoid microenvironment," *Blood*, 78:2650–2665, 1991.

Ward, "VH shuffling can be used to convert an Fv fragment of anti-hen egg lysozyme specificity to one that recognizes a T cell receptor V alpha," *Mol. Immunol.*, 32:147–156, 1995.

Wienands, Larbolette, Reth, "Evidence for a preformed transducer complex organized by the B cell antigen receptor," *Proc. Natl. Acad. Sci., USA*, 93:7865–7870, 1996.

Wolff et al., "Human monoclonal antibody homodimers", *J. Immunol.*, 148:2469–2474, 1992.

Wolff et al., "Monoclonal antibody homoconjugates: Enhanced antitumor activity in nude mice", *Cancer Res.*, 53:2560–2565, 1993.

Yamanashi, Fukui, Wongsasant, Kinoshita, Ichimori, Toyoshima, Yamamoto, "Activation of Src-like proteintyrosine kinase Lyn and its association with phosphatidylinositol 3-kinase upon B-cell antigen receptor-mediated signaling," *Proc. Natl. Acad. Sci., USA*, 89:1118–1122, 1992.

Yefenof, Picker, Scheuermann, Tucker, Vitetta, Uhr, "Cancer dormancy: Isolation and characterization of dormant lymphoma cells," *Proc. Natl. Acad. Sci., USA*, 90:1829–1833, 1993.

Zahalka, Okon, Gosslar, Holzmann, Naor, "Lymph node (but not spleen) invasion by murine lymphoma is both CD44-and hyaluronate-dependent," *J. Immunol.*, 154:5345–5355, 1995.

Zahalka, Okon, Naor, "Blocking lymphomas invasiveness with a monoclonal antibody directed against the β-chain of the leukocyte adhesion molecule (CD18)," *J. Immunol.*, 150:4466–4477, 1993.

What is claimed is:

1. A homoconjugate of two or more monoclonal antibodies, wherein the homoconjugate comprises a monoclonal antibody that does not comprise an Fc region, wherein the homoconjugate comprises an anti-CD19, anti-CD20, anti-CD21, anti-CD22, anti-breast tumor, anti-ovarian tumor, anti-prostate tumor, anti-lung tumor, or anti-αHer2 monoclonal antibody, wherein the homoconjugate has anti-neoplastic activity and wherein said monoclonal antibody has substantially no anti-neoplastic activity in an unconjugated form.

2. The homoconjugate of claim 1, further defined as a homodimer.

3. The homoconjugate of claim 1, wherein the homoconjugate comprises a monoclonal antibody that is an IgG monomer.

4. The homoconjugate of claim 3, wherein the IgG is a mammalian IgG.

5. A method of making a homoconjugate of two or more monoclonal antibodies, wherein the homoconjugate comprises a monoclonal antibody that does not comprise an Fc region and wherein the monoclonal antibody is an anti-CD19, anti-CD20, anti-CD21, anti-CD22, anti-breast tumor, anti-ovarian tumor, anti-prostate tumor, anti-lung tumor, or anti-αHer2 monoclonal antibody, comprising:

obtaining a first monoclonal antibody that does not comprise an Fc region;

obtaining a second monoclonal antibody that does not comprise an Fc region; and conjugating the first monoclonal antibody to the second monoclonal antibody, wherein the first and second monoclonal antibodies have anti-neoplastic activity in a conjugated form and have substantially no anti-neoplastic activity in an unconjugated form.

6. The method of claim 5, wherein the homoconjugate is further defined as a homodimer.

7. The method of claim 5, wherein the homoconjugate comprises a monoclonal antibody that is an IgG monomer.

8. The method of claim 5, wherein the homo conjugate comprises a mammalian monoclonal antibody.

9. The method of claim 5, further consisting of:

obtaining a third monoclonal antibody; and conjugating the third monoclonal antibody to the homoconjugate.

10. A pharmaceutical composition comprising a homoconjugate comprising a monoclonal antibody and a pharmaceutically acceptable carrier, wherein the monoclonal antibody does not comprise an Fc region and wherein the monoclonal antibody is an anti-CD19, anti-CD20, anti-CD21, anti-CD22, anti-breast tumor, anti-ovarian tumor, anti-prostate tumor, anti-lung tumor, or anti-αHer2 monoclonal antibody and wherein the monoclonal antibody has anti-neoplastic activity in a conjugated form and has substantially no anti-neoplastic activity in an unconjugated form.

11. The pharmaceutical composition of claim 10, wherein the homoconjugate is further defined as a homodimer.

12. The pharmaceutical composition of claim 10, wherein the homoconjugate comprises a monoclonal antibody that is an IgG monomer.

13. The pharmaceutical composition of claim 10, wherein the homoconjugate comprises a mammalian monoclonal antibody.

* * * * *

UNITED STATES PATENT AND TRADEMARK OFFICE
CERTIFICATE OF CORRECTION

PATENT NO. : 6,368,596 B1 Page 1 of 1
DATED : April 9, 2002
INVENTOR(S) : Ghetie et al.

It is certified that error appears in the above-identified patent and that said Letters Patent is hereby corrected as shown below:

Column 52,
Line 7, please delete "homo conjugate" and insert -- homoconjugate -- therefor.

Signed and Sealed this

Sixteenth Day of July, 2002

Attest:

Attesting Officer

JAMES E. ROGAN
Director of the United States Patent and Trademark Office